(12) United States Patent
Inoue et al.

(10) Patent No.: US 9,309,458 B2
(45) Date of Patent: Apr. 12, 2016

(54) PHOSPHORESCENT ORGANOMETALLIC IRIDIUM COMPLEX, LIGHT-EMITTING ELEMENT, LIGHT-EMITTING DEVICE, ELECTRONIC DEVICE, AND LIGHTING DEVICE

(71) Applicant: Semiconductor Energy Laboratory Co., Ltd., Atsugi-shi, Kanagawa-ken (JP)

(72) Inventors: Hideko Inoue, Atsugi (JP); Takahiro Ishisone, Atsugi (JP); Nobuharu Ohsawa, Tochigi (JP); Satoshi Seo, Sagamihara (JP); Takao Hamada, Atsugi (JP)

(73) Assignee: SEMICONDUCTOR ENERGY LABORATORY CO., LTD., Kanagawa-ken (JP)

( * ) Notice: Subject to any disclaimer, the term of this patent is extended or adjusted under 35 U.S.C. 154(b) by 432 days.

(21) Appl. No.: 13/770,188

(22) Filed: Feb. 19, 2013

(65) Prior Publication Data
US 2013/0221278 A1    Aug. 29, 2013

(30) Foreign Application Priority Data

Feb. 24, 2012   (JP) ................................ 2012-038535

(51) Int. Cl.
| | |
|---|---|
| H01L 51/54 | (2006.01) |
| C09K 11/06 | (2006.01) |
| H01L 51/00 | (2006.01) |
| C07F 15/00 | (2006.01) |
| H05B 33/14 | (2006.01) |
| H01L 51/50 | (2006.01) |

(52) U.S. Cl.
CPC ............. *C09K 11/06* (2013.01); *C07F 15/0033* (2013.01); *H01L 51/0085* (2013.01); *H05B 33/14* (2013.01); *C09K 2211/1059* (2013.01); *C09K 2211/185* (2013.01); *H01L 51/5016* (2013.01)

(58) Field of Classification Search
None
See application file for complete search history.

(56) References Cited

U.S. PATENT DOCUMENTS

| 6,821,645 | B2 | 11/2004 | Igarashi et al. |
|---|---|---|---|
| 7,566,505 | B2 | 7/2009 | Ise et al. |
| 7,807,839 | B2 | 10/2010 | Inoue et al. |
| 2004/0026663 | A1 | 2/2004 | Heuer et al. |
| 2006/0008670 | A1 | 1/2006 | Lin et al. |
| 2006/0036097 | A1 | 2/2006 | Qiu et al. |
| 2006/0134461 | A1 | 6/2006 | Huo et al. |
| 2006/0154106 | A1 | 7/2006 | Walters et al. |
| 2007/0085073 | A1 | 4/2007 | Inoue et al. |
| 2011/0057560 | A1 | 3/2011 | Inoue et al. |
| 2011/0101854 | A1 | 5/2011 | Inoue et al. |
| 2011/0198988 | A1 | 8/2011 | Inoue et al. |
| 2011/0220882 | A1 | 9/2011 | Inoue et al. |
| 2013/0161598 | A1 | 6/2013 | Inoue et al. |

FOREIGN PATENT DOCUMENTS

| JP | 2007-137872 | 6/2007 |
|---|---|---|
| KR | 2004-0014346 A | 2/2004 |
| WO | WO 2004/101707 | 11/2004 |
| WO | WO-2006/000544 | 1/2006 |
| WO | WO 2014/085296 A1 * | 6/2014 |

OTHER PUBLICATIONS

U.S. Appl. No. 61/731,110, filed Nov. 29, 2012.*

(Continued)

*Primary Examiner* — Marie R. Yamnitzky
(74) *Attorney, Agent, or Firm* — Robinson Intellectual Property Law Office; Eric J. Robinson

(57) ABSTRACT

A novel phosphorescent organometallic iridium complex is provided in which a coordination position of a ligand with respect to a metal can be controlled in synthesis. A novel phosphorescent organometallic iridium complex is provided which can keep high quantum efficiency and can emit phosphorescence in the blue to green wavelength region. A phosphorescent organometallic iridium complex which includes a structure represented by General Formula (G1) and whose ligand is a 4H-1,2,4-triazole compound which has an unsubstituted phenyl group at the 3-position, a substituted or unsubstituted phenyl group at the 4-position, and a phenyl group at the 5-position. In the phenyl group at the 5-position, an alkyl group is bonded to at least one of the ortho-positions, and the other of the ortho-positions, the meta-positions, and the para-position are substituted or unsubstituted.

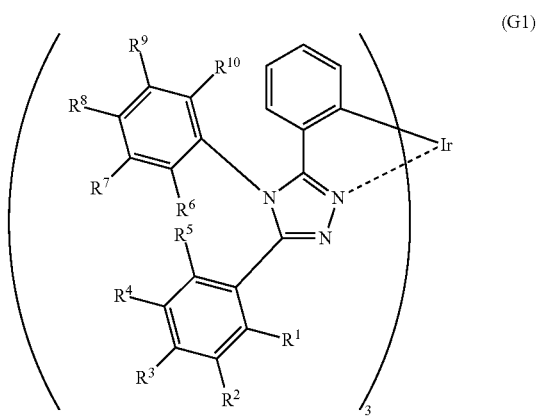

(G1)

24 Claims, 39 Drawing Sheets

(56) References Cited

OTHER PUBLICATIONS

Baldo et al., "Very High-Efficiency Green Organic Light-Emitting Devices Based on Electrophosphorescence," Appl. Phys. Lett. (Applied Physics Letters), Jul. 5, 1999, vol. 75, No. 1, pp. 4-6.

Chen et al., "Synthesis, structure, electrochemistry, photophysics and electroluminescence of 1,3,4-oxadiazole-based *ortho*-metalated iridium (III) complexes," Journal of Organometallic Chemistry, Aug. 1, 2006, vol. 691, No. 16, pp. 3519-3530.

Zamora et al., "Synthesis of Several Palladium Complexes Derived from 2,5-diphenyl-1,3,4-Oxadiazole. Reactivity against Nucleobase Models," Journal of Inorganic Biochemistry, Dec. 1, 1997, vol. 68, No. 4, pp. 257-263.

Liu et al., "Green-Yellow Electrophosphorescence from di [2,5-diphenyl-1,3,4-oxadiazole $C^{2'}$, $N^3$] Platinum (II) Doped PVK Devices," Chin. Phys. Lett. (Chinese Physics Letters), 2005, vol. 22, No. 3, pp. 723-726.

Wu et al., "Synthesis and photoluminescence of a novel iridium complex (BuPhOXD)2Ir(acac) with unit of 1,3,4-oxadiazole," Chinese Chemical Letters, 2005, vol. 16, No. 2, pp. 241-244 (Abstract Only).

European Search Report (Application No. 06021150.5) dated Jan. 29, 2007.

van Diemen et al., "Synthesis and Characterization of Orthometalated Rhodium (III) Complexes Containing Substituted Triazoles," Inorganic Chemistry, 1991, vol. 30, No. 21, pp. 4038-4043, American Chemical Society.

Holder.E et al., "New Trends in the Use of Transition Metal-Ligand Complexes for Applications in Electroluminescent Devices,", Adv. Mater. (Advanced Materials), May 1, 2005, vol. 17, No. 9, pp. 1109-1121.

\* cited by examiner

PHOSPHORESCENT ORGANOMETALLIC IRIDIUM COMPLEX, LIGHT-EMITTING ELEMENT, LIGHT-EMITTING DEVICE, ELECTRONIC DEVICE, AND LIGHTING DEVICE

BACKGROUND OF THE INVENTION

1. Field of the Invention

One embodiment of the present invention relates to a phosphorescent organometallic iridium complex that is capable of converting triplet excited energy into luminescence. In addition, one embodiment of the present invention relates to a light-emitting element, a light-emitting device, an electronic device, and a lighting device each using the phosphorescent organometallic iridium complex.

2. Description of the Related Art

A light-emitting element having a structure in which a light-emitting layer including an organic compound that is a light-emitting substance is provided between a pair of electrodes has attracted attention as a next-generation flat panel display element in terms of characteristics such as being thin and light in weight, high speed response, and direct current low voltage driving. Further, a display device including this light-emitting element is superior in contrast, image quality, and has wide viewing angle.

Some of organic compounds which can be used for a light-emitting layer are capable of emitting phosphorescence from an excited state. Phosphorescence refers to luminescence generated by transition between different energies in multiplicity. In an ordinary organic compound, phosphorescence refers to luminescence generated in returning from the triplet excited state to the singlet ground state (in contrast, fluorescence refers to luminescence in returning from the singlet excited state to the singlet ground state). When such a compound capable of emitting phosphorescence, i.e., converting triplet excited energy into luminescence (hereinafter referred to as phosphorescent compound), is used as a light-emitting substance in a light-emitting layer, internal quantum efficiency can be increased to allow a light-emitting element to be highly efficient.

As a phosphorescent compound, an organometallic complex in which iridium or the like is a central metal has attracted attention and a variety of novel organometallic complexes have been synthesized (for example, see Patent Document 1), but control of a coordination position of a ligand with respect to a central metal is becoming necessary for efficient synthesis of an organometallic complex with a desired structure.

REFERENCE

Patent Document

[Patent Document 1] Japanese Published Patent Application No. 2007-137872

SUMMARY OF THE INVENTION

In view of the above, according to one embodiment of the present invention, a novel phosphorescent organometallic iridium complex is provided in which a coordination position of a ligand with respect to metallic iridium can be controlled in synthesis. A novel organometallic complex is provided which can keep high quantum efficiency and can emit phosphorescence in the blue to green wavelength region. Further, according to one embodiment of the present invention, a highly reliable light-emitting element can be provided by using such a phosphorescent organometallic iridium complex. In addition, according to one embodiment of the present invention, a light-emitting element, a light-emitting device, an electronic device, or a lighting device which has high emission efficiency can be provided by using such a phosphorescent organometallic iridium complex.

One embodiment of the present invention is a phosphorescent organometallic iridium complex whose ligand is a 4H-1,2,4-triazole compound which has an unsubstituted phenyl group at the 3-position, a substituted or unsubstituted phenyl group at the 4-position, and a phenyl group at the 5-position. In the phenyl group at the 5-position, an alkyl group is bonded to at least one of the ortho-positions, and the other of the ortho-positions, the meta-positions, and the para-position are substituted or unsubstituted. Accordingly, one embodiment of the present invention is a phosphorescent organometallic iridium complex having a structure represented by General Formula (G1).

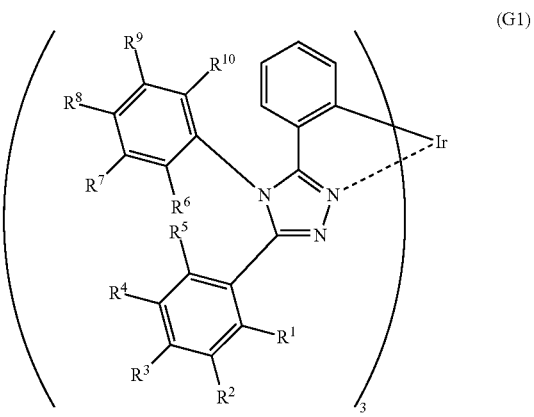

In the formula, $R^1$ represents an alkyl group having 1 to 6 carbon atoms. Further, $R^2$ to $R^{10}$ separately represent hydrogen or an alkyl group having 1 to 6 carbon atoms.

Further, another embodiment of the present invention is a phosphorescent organometallic iridium complex represented by General Formula (G2).

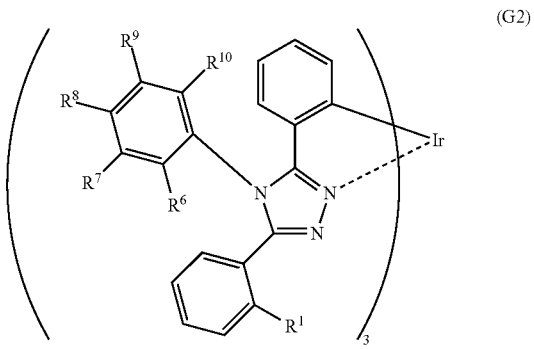

In the formula, $R^1$ represents an alkyl group having 1 to 6 carbon atoms. Further, $R^6$ to $R^{10}$ separately represent hydrogen or an alkyl group having 1 to 6 carbon atoms.

Further, another embodiment of the present invention is a phosphorescent organometallic iridium complex represented by Structural Formula (100).

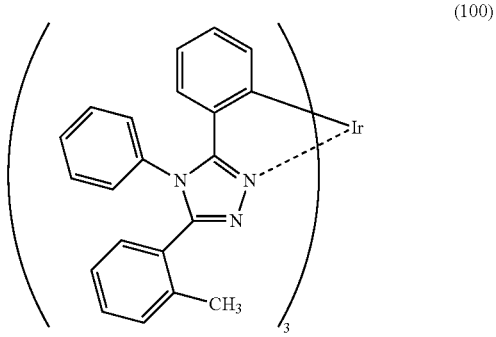

(100)

Further, another embodiment of the present invention is a phosphorescent organometallic iridium complex represented by Structural Formula (101).

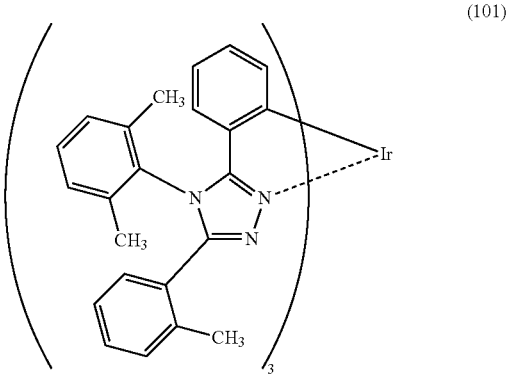

(101)

In each of the above-described phosphorescent organometallic iridium complexes which are embodiments of the present invention, the phenyl groups bonded to the 3-position and the 5-position of the triazole skeleton are different from each other in structure due to a substituent or substituents substituted for any hydrogen of the phenyl groups (specifically, the phenyl group at the 3-position is unsubstituted and the phenyl group at the 5-position has a substituent at least at one of the ortho-positions ($R^1$ in General Formulae (G1) and (G2))). Thus, since the phenyl group at the 5-position has a substituent and is steric, the phenyl group at the 3-position having less steric hindrance can be selectively bonded to iridium as the central metal to form an orthometalated structure. Moreover, since the phenyl group at the 5-position has a substituent so that the structure is no longer planar, the wavelength of light to be emitted can be shifted to the shorter wavelength side. Further, since the phenyl group at the 5-position has a substituent, the ligand has higher thermal stability than one with a substituent such as an alkyl group or an alkoxy group. Accordingly, thermal stability of the complex is improved, which allows a light-emitting element to have a long lifetime.

Furthermore, when the phenyl group bonded to the 4-position of the triazole skeleton has a substituent at the ortho-position in the phosphorescent organometallic iridium complex that is one embodiment of the present invention, the structure is no longer planar, so that the wavelength of light to be emitted can be shifted to the shorter wavelength side. Further, when the phenyl group bonded to the 4-position of the triazole skeleton has a substituent at the ortho-position, the sublimation temperature is reduced and thus, decomposition of the complex by vacuum evaporation can be suppressed, which results in higher stability. Accordingly, a long-life light-emitting element with favorable characteristics and high color purity can be obtained.

A light-emitting element can be highly efficient by including the phosphorescent organometallic iridium complex that is one embodiment of the present invention. Thus, the scope of one embodiment of the present invention includes a light-emitting element which includes the phosphorescent organometallic iridium complex that is one embodiment of the present invention.

Further, the present invention includes, in its category, electronic devices and lighting devices including light-emitting devices as well as light-emitting devices including light-emitting elements. The light-emitting device in this specification refers to an image display device, a light-emitting device, and a light source (e.g., a lighting device). In addition, the light-emitting device includes, in its category, all of a module in which a light-emitting device is connected to a connector such as a flexible printed circuit (FPC), a tape carrier package (TCP), a module in which a printed wiring board is provided on the tip of a TCP, and a module in which an integrated circuit (IC) is directly mounted on a light-emitting element by a chip on glass (COG) method.

According to one embodiment of the present invention, a novel phosphorescent organometallic iridium complex can be provided in which a coordination position of a ligand with respect to metallic iridium is controlled in synthesis. According to one embodiment of the present invention, a phosphorescent organometallic iridium complex can be obtained which can keep high quantum efficiency and emit phosphorescence in the blue to green wavelength region. Further, according to one embodiment of the present invention, a highly reliable light-emitting element which includes such a phosphorescent organometallic iridium complex can be provided. In addition, according to one embodiment of the present invention, a light-emitting element, a light-emitting device, an electronic device, or a lighting device which includes such a phosphorescent organometallic iridium complex and has high emission efficiency can be provided.

DETAILED DESCRIPTION OF THE INVENTION

Figure 1:
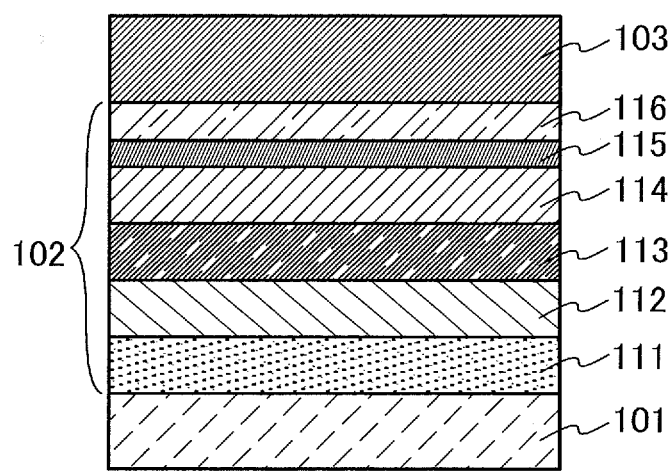
FIG. 1 illustrates a structure of a light-emitting element.

Hereinafter, embodiments of the present invention will be described in detail with reference to the accompanying drawings. Note that the present invention is not limited to the description below, and modes and details of the present invention can be modified in various ways without departing from the spirit and the scope thereof. Therefore, the present invention should not be construed as being limited to the description of the following embodiments.

(Embodiment 1)

In this embodiment, phosphorescent organometallic iridium complexes which are embodiments of the present invention are described.

A phosphorescent organometallic iridium complex that is one embodiment of the present invention is a phosphorescent organometallic iridium complex whose ligand is a 4H-1,2,4-triazole compound which has an unsubstituted phenyl group at the 3-position, a substituted or unsubstituted phenyl group at the 4-position, and a phenyl group at the 5-position. In the phenyl group at the 5-position, an alkyl group is bonded to at least one of the ortho-positions, and the other of the ortho-positions, the meta-positions, and the para-position are substituted or unsubstituted.

Conventionally, it has been difficult to know whether a phenyl group at the 3-position of a triazole skeleton or a phenyl group at the 5-position thereof is to be coordinated to iridium, in which case the phenyl groups at the 3-position and the 5-position of the triazole skeleton have needed to have the same structure. In contrast, in the phosphorescent organometallic iridium complex that is one embodiment of the present invention, since an alkyl group is bonded to one of the ortho-positions (R' in General Formula (G1)) of the phenyl group at the 5-position of the triazole skeleton, orthometalation does not occur at the other of the ortho-positions ($R^5$ in General Formula (G1)) even when $R^5$ in General Formula (G1) represents hydrogen as well as when $R^5$ in General Formula (G1) has a substituent, and the phenyl group which has no substituent and is bonded to the 3-position of the triazole skeleton can be selectively coordinated to iridium, i.e., can be bonded to iridium to form an orthometalated structure.

Note that it is preferable that the phenyl group bonded to iridium to form an orthometalated structure be unsubstituted, which contributes to improvement in reliability.

The phosphorescent organometallic iridium complex that is one embodiment of the present invention can have improved reliability since the 3-position of the triazole skeleton has the unsubstituted phenyl group, and can have a wide variety of structures since, in the phenyl group at the 5-position of the triazole skeleton, except that one of the ortho-positions ($R^1$ in General Formula (G1)) has the alkyl group, the other of the ortho-positions ($R^5$ in General Formula (G1)), the meta-positions ($R^2$ and $R^4$ in General Formula (G1)), and the para-position ($R^3$ in General Formula (G1)) can be substituted or unsubstituted. Moreover, since the phenyl group at the 5-position of the triazole skeleton has a substituent so that the structure is no longer planar, the wavelength of light to be emitted can be shifted to the shorter wavelength side.

Note that an organometallic complex including a structure represented by General Formula (G1) is one mode of the phosphorescent organometallic iridium complex in this embodiment whose ligand is a triazole compound which has a phenyl group at the 4-position and has, at the 5-position, a phenyl group having an alkyl group at the ortho-position.

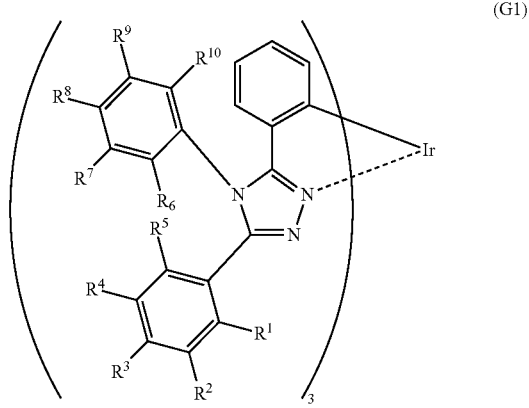

(G1)

In General Formula (G1), $R^1$ represents an alkyl group having 1 to 6 carbon atoms. Further, $R^2$ to $R^{10}$ separately represent hydrogen or an alkyl group having 1 to 6 carbon atoms.

Here, specific examples of the alkyl group having 1 to 6 carbon atoms in $R^1$ to $R^{10}$ include a methyl group, an ethyl group, a propyl group, an isopropyl group, a butyl group, a sec-butyl group, an isobutyl group, a tert-butyl group, a pentyl group, an isopentyl group, a sec-pentyl group, a tert-pentyl group, a neopentyl group, a hexyl group, an isohexyl group, a sec-hexyl group, a tert-hexyl group, a neohexyl group, a 3-methylpentyl group, a 2-methylpentyl group, a 2-ethylbutyl group, a 1,2-dimethylbutyl group, and a 2,3-dimethylbutyl group. In light of the steric structure and the synthesis yield of the complex, a methyl group, an ethyl group, and an isopropyl group are preferable; a methyl group is particularly preferable.

One embodiment of the present invention is a phosphorescent organometallic iridium complex represented by General Formula (G2).

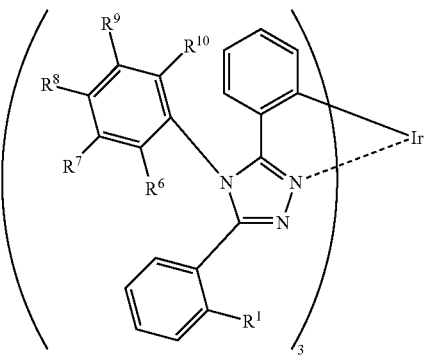

(G2)

In General Formula (G2), $R^1$ represents an alkyl group having 1 to 6 carbon atoms. Further, $R^6$ to $R^{10}$ separately represent hydrogen or an alkyl group having 1 to 6 carbon atoms. Note that specific examples of the alkyl group having 1 to 6 carbon atoms in $R^1$ and $R^6$ to $R^{10}$ are the same as those of the alkyl group having 1 to 6 carbon atoms in General Formula (G1).

Here, in any of the above-described phosphorescent organometallic iridium complexes, the phenyl group bonded to the 4-position of the triazole skeleton preferably has a substituent at the ortho-position(s) ($R^6$ and/or $R^{10}$ in General Formula (G1) or (G2)). In that case, the structure is no longer planar, so that the wavelength of light to be emitted can be shifted to the shorter wavelength side. Further, the sublimation temperature is reduced, so that decomposition of the complex by vacuum evaporation can be suppressed, which results in higher stability. Accordingly, a long-life light-emitting element with favorable characteristics and high color purity can be obtained. In light of the steric structure and the synthesis yield of the complex, the substituent is preferably a methyl group, an ethyl group, or an isopropyl group, and a methyl group is particularly preferable.

Next, specific structural formulae of the above-described phosphorescent organometallic iridium complexes each of which is one embodiment of the present invention will be shown (Structural Formulae (100) to (121)). Note that the present invention is not limited thereto.

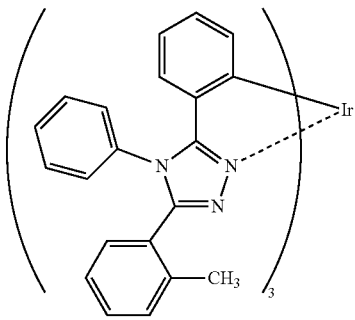

(100)

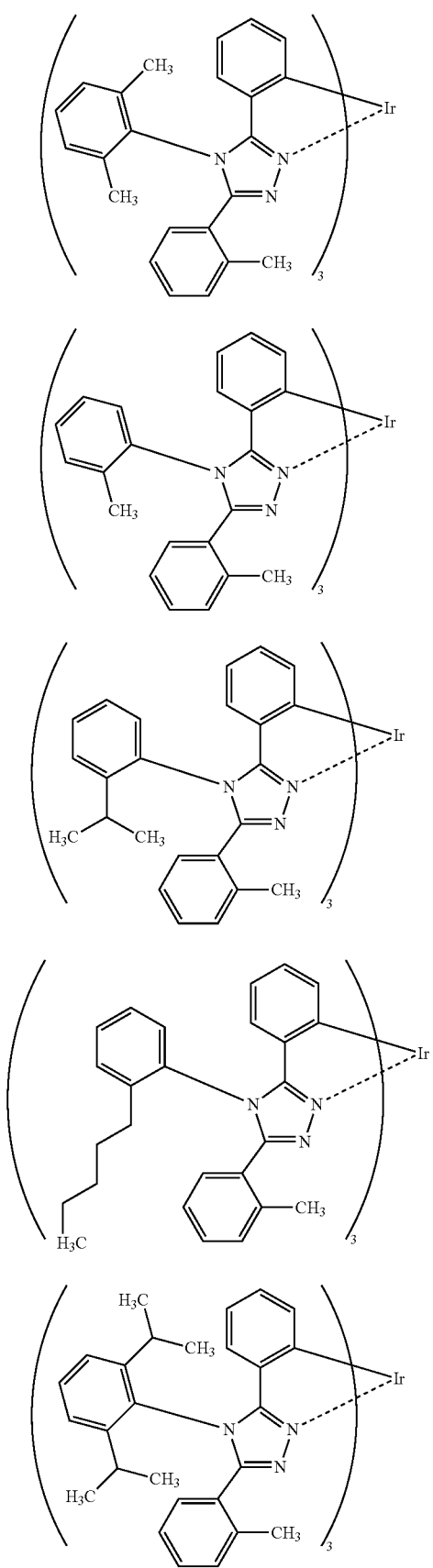

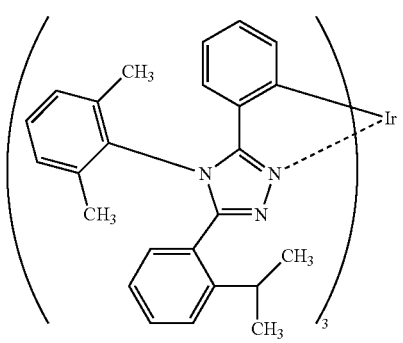
(111)
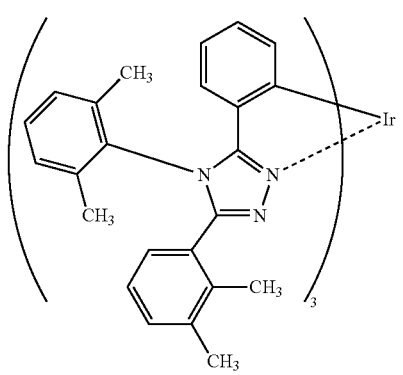
(112)
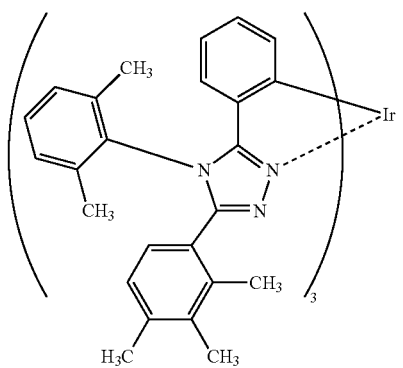
(113)
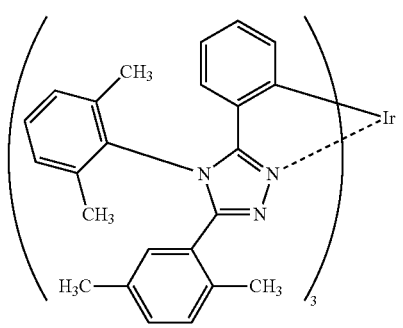
(114)
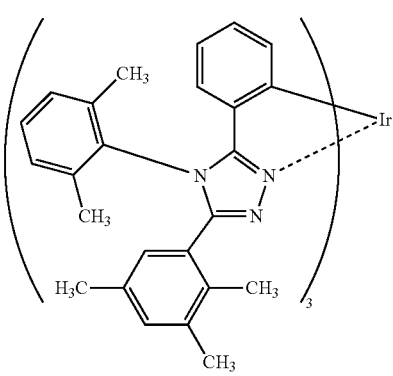
(115)
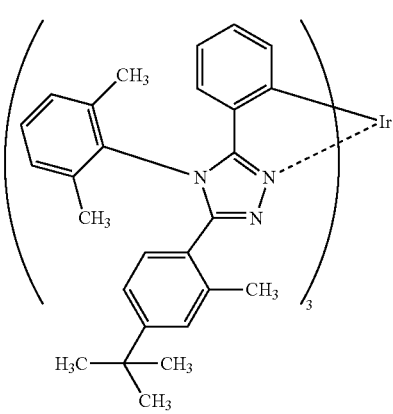
(116)
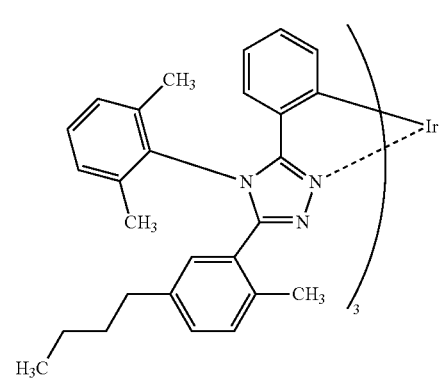
(117)
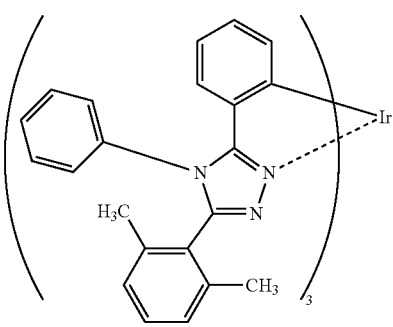
(118)

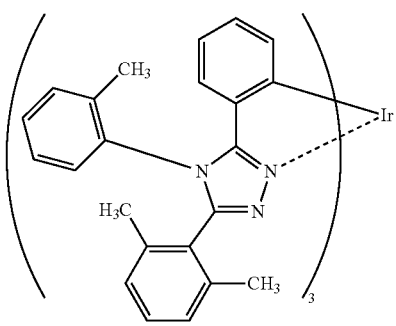

(119)

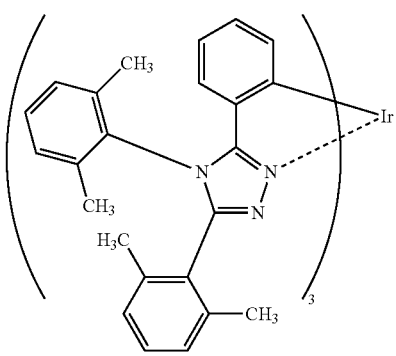

(120)

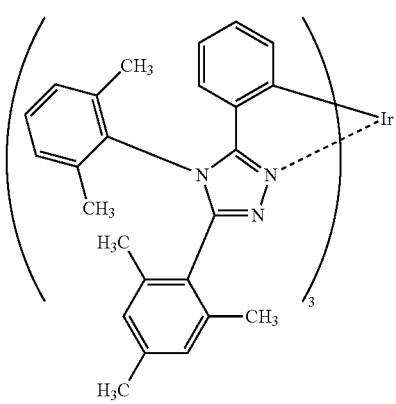

(121)

Note that phosphorescent organometallic iridium complexes represented by Structural Formulae (100) to (121) are novel substances capable of emitting phosphorescence. Note that there can be geometrical isomers and stereoisomers of these substances depending on the type of the ligand. The phosphorescent organometallic iridium complex that is one embodiment of the present invention includes all of these isomers.

Next, an example of a method of synthesizing a phosphorescent organometallic iridium complex represented by General Formula (G1) is described.

<<Method of Synthesizing Phosphorescent Organometallic Iridium Complex Represented by General Formula (G1)>>

Step 1: Method of Synthesizing 4H-1,2,4-Triazole Derivative

First, an example of a method of synthesizing a 4H-1,2,4-triazole derivative represented by General Formula (G0) is described.

(G0)

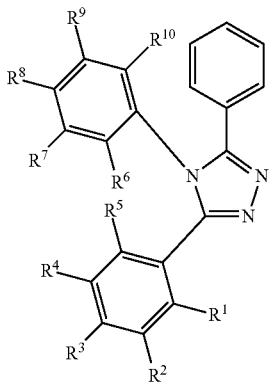

In General Formula (G0), $R^1$ represents an alkyl group having 1 to 6 carbon atoms, and $R^2$ to $R^{10}$ separately represent hydrogen or an alkyl group having 1 to 6 carbon atoms.

As shown in Synthesis Scheme (A-1), benzoylhydrazine (A1) and a thioether compound or an N-substituted thioamide compound (A2) are reacted with each other, so that a 4H-1,2,4-triazole derivative can be obtained.

(A-1)

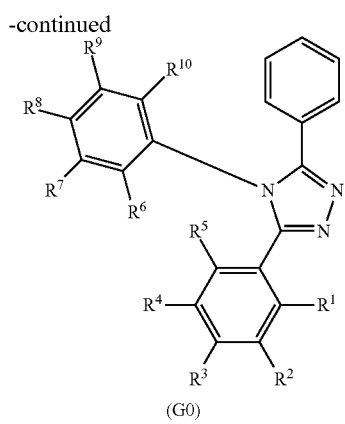

(G0)

In Synthesis Scheme (A-1), $R^1$ represents an alkyl group having 1 to 6 carbon atoms, and $R^2$ to $R^{10}$ separately represent hydrogen or an alkyl group having 1 to 6 carbon atoms.

Note that the method of synthesizing a 4H-1,2,4-triazole derivative is not limited to Synthesis Scheme (A-1). As an example of the other synthesis methods, there is a method in which a hydrazide compound including $R^1$ and a thioether compound or an N-substituted thioamide compound are reacted with each other. As shown in Synthesis Scheme (A'-1), there is also a method in which a dihydrazide compound (A1') and a primary amine compound (A2') are reacted with each other.

As described above, a 4H-1,2,4-triazole derivative represented by General Formula (G0) can be synthesized by a simple synthesis scheme.

Step 2: Method of Synthesizing Orthometalated Complex Including 4H-1,2,4-Triazole Derivative as Ligand As shown in Synthesis Scheme (A-2), the 4H-1,2,4-triazole derivative obtained by Synthesis Scheme (A-1) in Step 1 is mixed with an iridium compound which contains a halogen (e.g., iridium chloride hydrate or ammonium hexachloroiridate) or with an iridium organometallic complex compound (e.g., an acetylacetonato complex, a diethylsulfide complex, a μ-halogen bridged dinuclear complex in which a 4H-1,2,4-triazole derivative is a ligand, or a μ-oxo bridged dinuclear complex in which a 4H-1,2,4-triazole derivative is a ligand) and the mixture is then heated, so that a phosphorescent organometallic iridium complex having the structure represented by General Formula (G1) can be obtained.

There is no particular limitation on a heating means, and an oil bath, a sand bath, or an aluminum block may be used as a heating means. Alternatively, microwaves can be used as a heating means. Further, this heating process may be performed after the 4H-1,2,4-triazole derivative obtained in Step 1 and the iridium compound which contains a halogen or the iridium organometallic complex compound are dissolved in an alcohol-based solvent (e.g., glycerol, ethylene glycol, 2-methoxyethanol, or 2-ethoxyethanol).

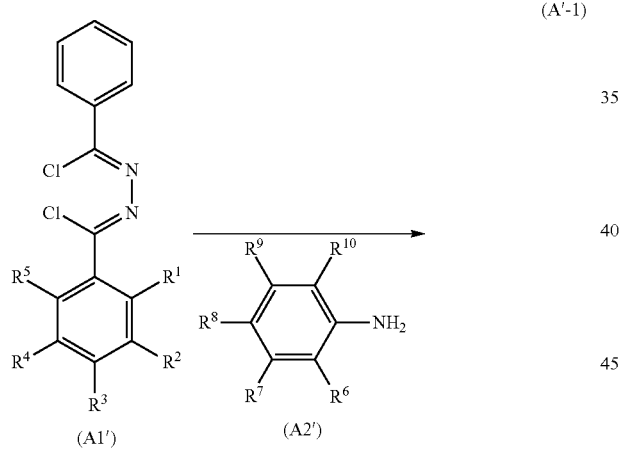

(A'-1)

(A1')   (A2')

(G0)

In Synthesis Scheme (A'-1), $R^1$ represents an alkyl group having 1 to 6 carbon atoms, and $R^2$ to $R^{10}$ separately represent hydrogen or an alkyl group having 1 to 6 carbon atoms.

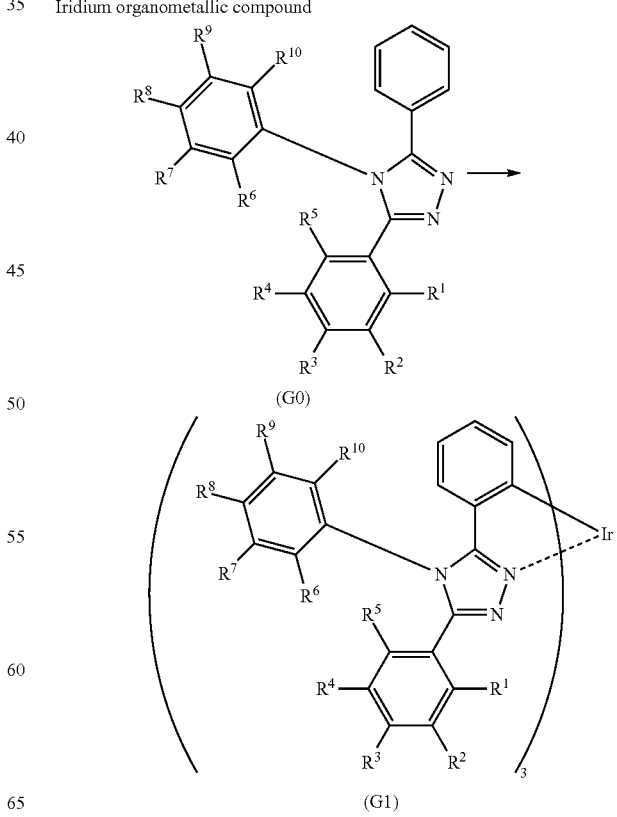

(A-2)

Iridium compound containing halogen
or
Iridium organometallic compound
+

(G0)

(G1)

In Synthesis Scheme (A-2), $R^1$ represents an alkyl group having 1 to 6 carbon atoms, and $R^2$ to $R^{10}$ separately represent hydrogen or an alkyl group having 1 to 6 carbon atoms.

As the above compounds (A1), (A2), (A1'), and (A2'), many varieties of compounds are commercially available or can be synthesized; accordingly, a great variety of derivatives can be synthesized as the 4H-1,2,4-triazole derivative represented by General Formula (G0). Thus, a feature of the phosphorescent organometallic iridium complex which is one embodiment of the present invention is the abundance of ligand variations. By using such an organometallic complex having wide variations of a ligand in manufacture of a light-emitting element, fine adjustment of element characteristics required for the light-emitting element can be performed easily.

The above is the description of the example of a method of synthesizing a phosphorescent organometallic iridium complex that is one embodiment of the present invention; however, the present invention is not limited thereto and any other synthesis method may be employed.

The above-described phosphorescent organometallic iridium complex that is one embodiment of the present invention can emit phosphorescence and thus can be used as a light-emitting material or a light-emitting substance of a light-emitting element.

With the use of the phosphorescent organometallic iridium complex that is one embodiment of the present invention, a light-emitting element, a light-emitting device, an electronic device, or a lighting device with high emission efficiency can be obtained. It is also possible to obtain a light-emitting element, a light-emitting device, an electronic device, or a lighting device with low power consumption.

The structure described in this embodiment can be combined as appropriate with any of the structures described in the other embodiments.

(Embodiment 2)

In this embodiment, a light-emitting element in which the organometallic complex described in Embodiment 1 as one embodiment of the present invention is used for a light-emitting layer is described with reference to FIG. 1.

In a light-emitting element described in this embodiment, as illustrated in FIG. 1, an EL layer 102 including a light-emitting layer 113 is provided between a pair of electrodes (a first electrode (anode) 101 and a second electrode (cathode) 103), and the EL layer 102 includes a hole-injection layer 111, a hole-transport layer 112, an electron-transport layer 114, an electron-injection layer 115, a charge generation layer (E) 116, and the like in addition to the light-emitting layer 113.

By application of a voltage to such a light-emitting element, holes injected from the first electrode 101 side and electrons injected from the second electrode 103 side recombine in the light-emitting layer 113 to raise the organometallic complex to an excited state. Then, light is emitted when the organometallic complex in the excited state returns to the ground state. Thus, the organometallic complex of one embodiment of the present invention functions as a light-emitting substance in the light-emitting element.

The hole-injection layer 111 included in the EL layer 102 is a layer containing a substance having a high hole-transport property and an acceptor substance. When electrons are extracted from the substance having a high hole-transport property owing to the acceptor substance, holes are generated. Thus, holes are injected from the hole-injection layer 111 into the light-emitting layer 113 through the hole-transport layer 112.

The charge generation layer (E) 116 is a layer containing a substance having a high hole-transport property and an acceptor substance. Owing to the acceptor substance, electrons are extracted from the substance having a high hole-transport property and the extracted electrons are injected from the electron-injection layer 115 having an electron-injection property into the light-emitting layer 113 through the electron-transport layer 114.

A specific example in which the light-emitting element described in this embodiment is manufactured is described.

For the first electrode (anode) 101 and the second electrode (cathode) 103, a metal, an alloy, an electrically conductive compound, a mixture thereof, and the like can be used. Specifically, indium oxide-tin oxide (indium tin oxide), indium oxide-tin oxide containing silicon or silicon oxide, indium oxide-zinc oxide (indium zinc oxide), indium oxide containing tungsten oxide and zinc oxide, gold (Au), platinum (Pt), nickel (Ni), tungsten (W), chromium (Cr), molybdenum (Mo), iron (Fe), cobalt (Co), copper (Cu), palladium (Pd), and titanium (Ti) can be used. In addition, an element belonging to Group 1 or Group 2 of the periodic table, for example, an alkali metal such as lithium (Li) or cesium (Cs), an alkaline earth metal such as calcium (Ca) or strontium (Sr), magnesium (Mg), an alloy containing such an element (MgAg, AlLi), a rare earth metal such as europium (Eu) or ytterbium (Yb), an alloy containing such an element, graphene, and the like can be used. The first electrode (anode) 101 and the second electrode (cathode) 103 can be formed by, for example, a sputtering method, an evaporation method (including a vacuum evaporation method), or the like.

As the substance having a high hole-transport property which is used for the hole-injection layer 111, the hole-transport layer 112, and the charge generation layer (E) 116, the following can be given, for example: aromatic amines such as 4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), 4,4',4"-tris(carbazol-9-yl)triphenylamine (abbreviation: TCTA), 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), and 4,4'-bis[N-(spiro-9,9'-bifluoren-2-yl)-N-phenylamino]biphenyl (abbreviation: BSPB); 3-[N-(9-phenylcarbazol-3-yl)-N-phenylamino]-9-phenylcarbazole (abbreviation: PCzPCA1); 3,6-bis[N-(9-phenylcarbazol-3-yl)-N-phenylamino]-9-phenylcarbazole (abbreviation: PCzPCA2); 3-[N-(1-naphthyl)-N-(9-phenylcarbazol-3-yl)-amino]-9-phenylcarbazole (abbreviation: PCzPCN1); and the like. In addition, the following carbazole derivatives and the like can be used: 4,4'-di(N-carbazolyl)biphenyl (abbreviation: CBP), 1,3,5-tris[4-(N-carbazolyl)-phenyl]benzene (abbreviation: TCPB), and 9-[4-(10-phenyl-9-anthracenyl)phenyl]-9H-carbazole (abbreviation: CzPA). The substances mentioned here are mainly ones that have a hole mobility of $10^{-6}$ cm$^2$/Vs or higher. Note that any substance other than the above substances may be used as long as the hole-transport property is higher than the electron-transport property.

Further, a high molecular compound such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), or poly[N,N'-bis(4-butylphenyl)-N,N'-bis(phenyl)benzidine] (abbreviation: Poly-TPD) can be used.

As examples of the acceptor substance that is used for the hole-injection layer 111 and the charge generation layer (E) 116, a transition metal oxide or an oxide of a metal belonging to any of Group 4 to Group 8 of the periodic table can be given. Specifically, molybdenum oxide is particularly preferable.

The light-emitting layer 113 contains the organometallic complex described in Embodiment 1 as a guest material serving as a light-emitting substance and a substance that has higher triplet excitation energy than this organometallic complex as a host material.

Preferable examples of the substance (i.e., host material) used for dispersing any of the above-described organometallic complexes include an aromatic amine such as 4,4',4"-tris[N-(3-methylphenyl)-N-phenylamino]triphenylamine (abbreviation: MTDATA); a carbazole derivative such as CBP, 1,3-bis(N-carbazolyl)benzene (abbreviation: mCP), 4,4'-bis(carbazol-9-yl)-2,2'-dimethylbiphenyl (abbreviation: CDBP), and 4,4',4"-tris(carbazol-9-yl)triphenylamine (abbreviation: TCTA); a nitrogen-containing heterocyclic compound; a thiophene derivative; a furan derivative; and a metal complex of zinc, aluminum, or the like. It is also possible to use a high molecular compound such as PVK, a polyparaphenylenevinylene derivative, a polyparaphenylene derivative, a polyfluorene derivative, or a poly(spirofluorene) derivative, or a dendrimer.

Note that in the case where the light-emitting layer 113 contains the above-described organometallic complex (guest material) and the host material, phosphorescence with high emission efficiency can be obtained from the light-emitting layer 113.

The electron-transport layer 114 is a layer containing a substance having a high electron-transport property. For the electron-transport layer 114, metal complexes such as $Alq_3$, tris(4-methyl-8-quinolinolato)aluminum (abbreviation: $Almq_3$), bis(10-hydroxybenzo[h]quinolinato)beryllium (abbreviation: $BeBq_2$), BAlq, $Zn(BOX)_2$, or bis[2-(2-hydroxyphenyl)benzothiazolato]zinc (abbreviation: $Zn(BTZ)_2$) can be used. Alternatively, a heteroaromatic compound such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: Bphen), bathocuproine (abbreviation: BCP), or 4,4'-bis(5-methylbenzoxazol-2-yl)stilbene (abbreviation: BzOs) can be used. Further alternatively, a high molecular compound such as poly(2,5-pyridinediyl) (abbreviation: PPy), poly[(9,9-dihexylfluorene-2,7-diyl)-co-(pyridine-3,5-diyl)] (abbreviation: PF-Py), or poly[(9,9-dioctylfluorene-2,7-diyl)-co-(2,2'-bipyridine-6,6'-diyl)] (abbreviation: PF-BPy) can be used. The substances mentioned here are mainly ones that have an electron mobility of $10^{-6}$ $cm^2/Vs$ or higher. Note that any substance other than the above substances may be used for the electron-transport layer 114 as long as the electron-transport property is higher than the hole-transport property.

Further, the electron-transport layer 114 is not limited to a single layer, and a stacked layer in which two or more layers containing any of the above-described substances are stacked may be used.

The electron-injection layer 115 is a layer containing a substance having a high electron-injection property. For the electron-injection layer 115, an alkali metal, an alkaline earth metal, magnesium (Mg), or a compound of any of the above metals such as lithium fluoride (LiF), cesium fluoride (CsF), calcium fluoride ($CaF_2$), or lithium oxide ($LiO_x$) can be used. Alternatively, a rare earth metal compound such as erbium fluoride ($ErF_3$) can be used. Further alternatively, the substances for forming the electron-transport layer 114, which are described above, can be used.

Alternatively, a composite material in which an organic compound and an electron donor (donor) are mixed may be used for the electron-injection layer 115. Such a composite material is excellent in an electron-injection property and an electron-transport property because electrons are generated in the organic compound by the electron donor. In this case, the organic compound is preferably a material excellent in transporting the generated electrons. Specifically, the substances for forming the electron-transport layer 114 (e.g., a metal complex and a heteroaromatic compound), which are described above, or the like can be used. As the electron donor, a substance showing an electron-donating property with respect to the organic compound may be used. Preferable examples are an alkali metal, an alkaline earth metal, and a rare earth metal. Specifically, magnesium and the like can be used as well as lithium, cesium, calcium, erbium, and ytterbium. In addition, alkali metal oxide or alkaline earth metal oxide such as lithium oxide, calcium oxide, barium oxide, and the like can be given. A Lewis base such as magnesium oxide can alternatively be used. An organic compound such as tetrathiafulvalene (abbreviation: TTF) can alternatively be used.

Note that each of the above-described hole-injection layer 111, hole-transport layer 112, light-emitting layer 113, electron-transport layer 114, electron-injection layer 115, and charge generation layer (E) 116 can be formed by a method such as an evaporation method (e.g., a vacuum evaporation method), an ink-jet method, or a coating method.

In the above-described light-emitting element, current flows due to a potential difference generated between the first electrode 101 and the second electrode 103 and holes and electrons recombine in the EL layer 102, whereby light is emitted. Then, the emitted light is extracted outside through one or both of the first electrode 101 and the second electrode 103. Therefore, one or both of the first electrode 101 and the second electrode 103 are electrodes having a light-transmitting property.

The above-described light-emitting element can emit phosphorescence originating from the organometallic complex and thus can have higher efficiency than a light-emitting element using a fluorescent compound.

Note that the light-emitting element described in this embodiment is an example of a light-emitting element manufactured using the organometallic complex that is one embodiment of the present invention. Further, as a light-emitting device including the above light-emitting element, a passive matrix light-emitting device and an active matrix light-emitting device can be manufactured. It is also possible to manufacture a light-emitting device with a microcavity structure including a light-emitting element which is a different light-emitting element from the above light-emitting elements as described in another embodiment. Each of the above light-emitting devices is included in the present invention.

Note that there is no particular limitation on the structure of the TFT in the case of manufacturing the active matrix light-emitting device. For example, a staggered TFT or an inverted staggered TFT can be used as appropriate. Further, a driver circuit formed over a TFT substrate may be formed of both an N-type TFT and a P-type TFT or only either an N-type TFT or a P-type TFT. Furthermore, there is also no particular limitation on crystallinity of a semiconductor film used for the TFT. For example, an amorphous semiconductor film, a crystalline semiconductor film, an oxide semiconductor film, or the like can be used.

Note that the structure described in this embodiment can be combined as appropriate with any of the structures described in the other embodiments.

(Embodiment 3)

In this embodiment, as one embodiment of the present invention, a light-emitting element in which two or more kinds of organic compounds as well as a phosphorescent organometallic iridium complex are used for a light-emitting layer is described.

Figure 2:
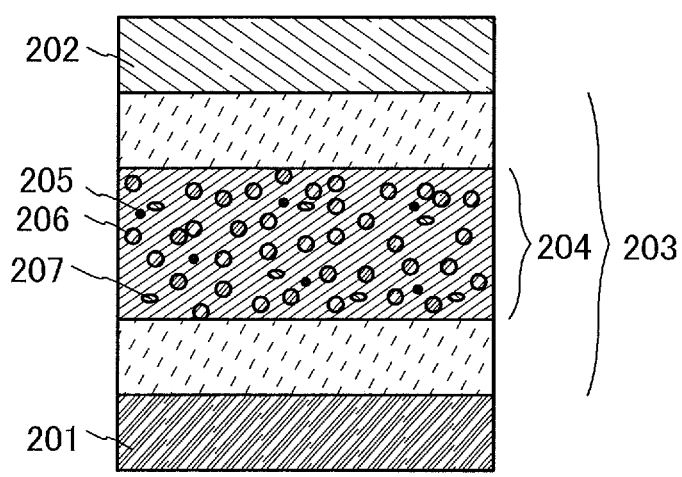
FIG. 2 illustrates a structure of a light-emitting element.

A light-emitting element described in this embodiment includes an EL layer 203 between a pair of electrodes (an anode 201 and a cathode 202) as illustrated in FIG. 2. Note that the EL layer 203 includes at least a light-emitting layer 204 and may include a hole-injection layer, a hole-transport layer, an electron-transport layer, an electron-injection layer, a charge generation layer (E), and the like. Note that for the hole-injection layer, the hole-transport layer, the electron-transport layer, the electron-injection layer, and the charge generation layer (E), the substances described in Embodiment 2 can be used.

The light-emitting layer 204 described in this embodiment contains a phosphorescent compound 205 using the phosphorescent organometallic iridium complex described in Embodiment 1, a first organic compound 206, and a second organic compound 207. Note that the phosphorescent compound 205 is a guest material in the light-emitting layer 204. Moreover, one of the first organic compound 206 and the second organic compound 207, the content of which is higher than that of the other in the light-emitting layer 204, is a host material in the light-emitting layer 204.

When the light-emitting layer 204 has the structure in which the guest material is dispersed in the host material, crystallization of the light-emitting layer can be suppressed. Further, it is possible to suppress concentration quenching due to high concentration of the guest material, and thus the light-emitting element can have higher emission efficiency.

Note that it is preferable that a triplet excitation energy level ($T_1$ level) of each of the first organic compound 206 and the second organic compound 207 be higher than that of the phosphorescent compound 205. The reason for this is that, when the $T_1$ level of the first organic compound 206 (or the second organic compound 207) is lower than that of the phosphorescent compound 205, the triplet excitation energy of the phosphorescent compound 205, which is to contribute to light emission, is quenched by the first organic compound 206 (or the second organic compound 207) and accordingly the emission efficiency decreases.

Here, for improvement in efficiency of energy transfer from a host material to a guest material, Forster mechanism (dipole-dipole interaction) and Dexter mechanism (electron exchange interaction), which are known as mechanisms of energy transfer between molecules, are considered. According to the mechanisms, it is preferable that an emission spectrum of a host material (a fluorescence spectrum in energy transfer from a singlet excited state, and a phosphorescence spectrum in energy transfer from a triplet excited state) largely overlap with an absorption spectrum of a guest material (specifically, a spectrum in an absorption band on the longest wavelength (lowest energy) side). However, in general, it is difficult to obtain an overlap between a fluorescence spectrum of a host material and an absorption spectrum in an absorption band on the longest wavelength (lowest energy) side of a guest material. The reason for this is as follows: if the fluorescence spectrum of the host material overlaps with the absorption spectrum in the absorption band on the longest wavelength (lowest energy) side of the guest material, since a phosphorescence spectrum of the host material is located on a longer wavelength (lower energy) side than the fluorescence spectrum, the $T_1$ level of the host material becomes lower than the $T_1$ level of the phosphorescent compound and the above-described problem of quenching occurs; yet, when the host material is designed in such a manner that the $T_1$ level of the host material is higher than the $T_1$ level of the phosphorescent compound in order to avoid the problem of quenching, the fluorescence spectrum of the host material is shifted to the shorter wavelength (higher energy) side, and thus the fluorescence spectrum does not have any overlap with the absorption spectrum in the absorption band on the longest wavelength (lowest energy) side of the guest material. For that reason, in general, it is difficult to obtain an overlap between a fluorescence spectrum of a host material and an absorption spectrum in an absorption band on the longest wavelength (lowest energy) side of a guest material so as to maximize energy transfer from a singlet excited state of a host material.

Thus, in this embodiment, a combination of the first organic compound 206 and the second organic compound 207 preferably forms an exciplex (also referred to as excited complex). In that case, the first organic compound 206 and the second organic compound 207 form an exciplex at the time of recombination of carriers (electrons and holes) in the light-emitting layer 204. Thus, in the light-emitting layer 204, a fluorescence spectrum of the first organic compound 206 and that of the second organic compound 207 are converted into an emission spectrum of the exciplex which is located on a longer wavelength side. Moreover, when the first organic compound 206 and the second organic compound 207 are selected in such a manner that the emission spectrum of the exciplex largely overlaps with the absorption spectrum of the guest material, energy transfer from a singlet excited state can be maximized. Note that also in the case of a triplet excited state, energy transfer from the exciplex, not the host material, is presumed to occur.

For the phosphorescent compound 205, the phosphorescent organometallic iridium complex described in Embodiment 1 is used. Although the combination of the first organic compound 206 and the second organic compound 207 can be determined such that an exciplex is formed, a combination of a compound which is likely to accept electrons (a compound having an electron-trapping property) and a compound which is likely to accept holes (a compound having a hole-trapping property) is preferably employed.

As a compound which is likely to accept electrons, a π-electron deficient heteroaromatic compound such as a nitrogen-containing heteroaromatic compound is preferable. For example, a quinoxaline derivative or a dibenzoquinoxaline derivative can be given and examples thereof include 2-[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo[f,h]quinoxaline (abbreviation: 2mDBTBPDBq-II), 2-[4-(3,6-diphenyl-9H-carbazol-9-yl)phenyl]dibenzo [f,h]quinoxaline (abbreviation: 2CzPDBq-III), 7-[3-(dibenzothiophen-4-yl)phenyl]dibenzo[f,h]quinoxaline (abbreviation: 7mDBTPDBq-II), and 6-[3-(dibenzothiophen-4-yl)phenyl]dibenzo[f,h]quinoxaline (abbreviation: 6mDBTPDBq-II).

As a compound which is likely to accept holes, a π-electron rich heteroaromatic compound (e.g., a carbazole derivative or an indole derivative) or an aromatic amine is preferable. For example, the following can be given: 4-phenyl-4'-(9-phenyl-9H-carbazol-3-yl)triphenylamine (abbreviation: PCBA1BP), 4,4'-di(1-naphthyl)-4''-(9-phenyl-9H-carbazol-3-yl)triphenylamine (abbreviation: PCBNBB), 3-[N-(1-naphthyl)-N-(9-phenylcarbazol-3-yl)amino]-9-phenylcarbazole (abbreviation: PCzPCN1), 4,4',4''-tris[N-(1-naphthyl)-

N-phenylamino]triphenylamine (abbreviation: 1'-TNATA), 2,7-bis[N-(4-diphenylaminophenyl)-N-phenylamino]-spiro-9,9'-bifluorene (abbreviation: DPA2SF), N,N'-bis(9-phenyl-carbazol-3-yl)-N,N'-diphenylbenzene-1,3-diamine (abbreviation: PCA2B), N-(9,9-dimethyl-2-N',N'-diphenylamino-9H-fluoren-7-yl)diphenylamine (abbreviation: DPNF), N,N',N''-triphenyl-N,N',N''-tris(9-phenylcarbazl-3-yl)benzene-1,3,5-triamine (abbreviation: PCA3B), 2-[N-(9-phenylcarbazol-3-yl)-N-phenylamino]spiro-9,9'-bifluorene (abbreviation: PCASF), 2-[N-(4-diphenylaminophenyl)-N-phenylamino]spiro-9,9'-bifluorene (abbreviation: DPASF), N,N'-bis[4-(carbazol-9-yl)phenyl]-N,N'-diphenyl-9,9-dimethylfluorene-2,7-diamine (abbreviation: YGA2F), 4,4'-bis[N-(3-methylphenyl)-N-phenylamino]biphenyl (abbreviation: TPD), 4,4'-bis[N-(4-diphenylaminophenyl)-N-phenylamino]biphenyl (abbreviation: DPAB), N-(9,9-dimethyl-9H-fluoren-2-yl)-N-{9,9-dimethyl-2-[N'-phenyl-N'-(9,9-dimethyl-9H-fluoren-2-yl)amino]-9H-fluoren-7-yl}phenylamine (abbreviation: DFLADFL), 3-[N-(9-phenylcarbazol-3-yl)-N-phenylamino]-9-phenylcarbazole (abbreviation: PCzPCA1), 3-[N-(4-diphenylaminophenyl)-N-phenylamino]-9-phenylcarbazole (abbreviation: PCzDPA1), 3,6-bis[N-(4-diphenylaminophenyl)-N-phenylamino]-9-phenylcarbazole (abbreviation: PCzDPA2), 4,4'-bis(N-{4-[N'-(3-methylphenyl)-N'-phenylamino]phenyl}-N-phenylamino)biphenyl (abbreviation: DNTPD), 3,6-bis[N-(4-diphenylaminophenyl)-N-(1-naphthyl)amino]-9-phenylcarbazole (abbreviation: PCzTPN2), and 3,6-bis[N-(9-phenylcarbazol-3-yl)-N-phenylamino]-9-phenylcarbazole (abbreviation: PCzPCA2).

As for the above-described first and second organic compounds 206 and 207, the present invention is not limited to the above examples. The combination is determined so that an exciplex can be formed, the emission spectrum of the exciplex overlaps with the absorption spectrum of the phosphorescent compound 205, and the peak of the emission spectrum of the exciplex has a longer wavelength than the peak of the absorption spectrum of the phosphorescent compound 205.

Note that in the case where a compound which is likely to accept electrons and a compound which is likely to accept holes are used for the first organic compound 206 and the second organic compound 207, carrier balance can be controlled by the mixture ratio of the compounds. Specifically, the ratio of the first organic compound to the second organic compound is preferably 1:9 to 9:1.

In the light-emitting element described in this embodiment, energy transfer efficiency can be improved owing to energy transfer utilizing an overlap between an emission spectrum of an exciplex and an absorption spectrum of a phosphorescent compound; accordingly, it is possible to achieve high external quantum efficiency of the light-emitting element.

Note that in another structure of the present invention, the light-emitting layer 204 can be formed using a host molecule having a hole-trapping property and a host molecule having an electron-trapping property as the two kinds of organic compounds other than the phosphorescent compound 205 (guest material) so that a phenomenon (guest coupled with complementary hosts: GCCH) occurs in which holes and electrons are introduced to guest molecules existing in the two kinds of host molecules and the guest molecules are brought into an excited state.

At this time, the host molecule having a hole-trapping property and the host molecule having an electron-trapping property can be respectively selected from the above-described compounds which are likely to accept holes and the above-described compounds which are likely to accept electrons.

Note that the light-emitting element described in this embodiment is an example of a structure of a light-emitting element; it is possible to apply a light-emitting element having another structure, which is described in another embodiment, to a light-emitting device that is one embodiment of the present invention. Further, as a light-emitting device including the above light-emitting element, a passive matrix light-emitting device and an active matrix light-emitting device can be manufactured. It is also possible to manufacture a light-emitting device with a microcavity structure including a light-emitting element which is a different light-emitting element from the above light-emitting elements as described in another embodiment. Each of the above light-emitting devices is included in the present invention.

Note that there is no particular limitation on the structure of the TFT in the case of manufacturing the active matrix light-emitting device. For example, a staggered TFT or an inverted staggered TFT can be used as appropriate. Further, a driver circuit formed over a TFT substrate may be formed of both an N-type TFT and a P-type TFT or only either an N-type TFT or a P-type TFT. Furthermore, there is also no particular limitation on crystallinity of a semiconductor film used for the TFT. For example, an amorphous semiconductor film, a crystalline semiconductor film, an oxide semiconductor film, or the like can be used.

Note that the structure described in this embodiment can be combined as appropriate with any of the structures described in the other embodiments.

(Embodiment 4)

In this embodiment, as one embodiment of the present invention, a light-emitting element (hereinafter referred to as tandem light-emitting element) in which a charge generation layer is provided between a plurality of EL layers is described.

Figure 3A:
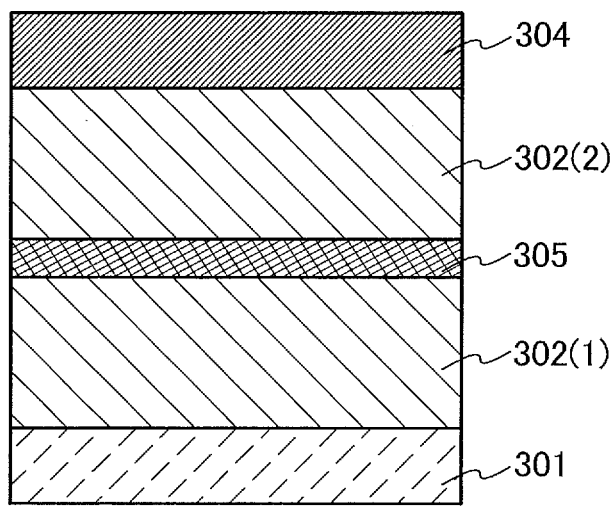
FIGS. 3A and 3B illustrate structures of light-emitting elements.

A light-emitting element described in this embodiment is a tandem light-emitting element including a plurality of EL layers (a first EL layer 302(1) and a second EL layer 302(2)) between a pair of electrodes (a first electrode 301 and a second electrode 304) as illustrated in FIG. 3A.

In this embodiment, the first electrode 301 functions as an anode, and the second electrode 304 functions as a cathode. Note that the first electrode 301 and the second electrode 304 can have structures similar to those described in Embodiment 2.

In addition, although the plurality of EL layers (the first EL layer 302(1) and the second EL layer 302(2)) may have a structure similar to that of the EL layer described in Embodiment 2 or 3, any of the EL layers may have a structure similar to that of the EL layer described in Embodiment 2 or 3. In other words, the structures of the first EL layer 302(1) and the second EL layer 302(2) may be the same or different from each other and can be similar to that of the EL layer described in Embodiment 2 or 3.

Further, a charge generation layer (I) 305 is provided between the plurality of EL layers (the first EL layer 302(1) and the second EL layer 302(2)). The charge generation layer (I) 305 has a function of injecting electrons into one of the EL layers and injecting holes into the other of the EL layers when a voltage is applied between the first electrode 301 and the second electrode 304. In this embodiment, when a voltage is applied such that the potential of the first electrode 301 is higher than that of the second electrode 304, the charge generation layer (I) 305 injects electrons into the first EL layer 302(1) and injects holes into the second EL layer 302(2).

Note that in terms of light extraction efficiency, the charge generation layer (I) 305 preferably has a light-transmitting property with respect to visible light (specifically, the charge generation layer (I) 305 has a visible light transmittance of 40% or more). Further, the charge generation layer (I) 305 functions even if it has lower conductivity than the first electrode 301 or the second electrode 304.

The charge generation layer (I) 305 may have either a structure in which an electron acceptor (acceptor) is added to an organic compound having a high hole-transport property or a structure in which an electron donor (donor) is added to an organic compound having a high electron-transport property. Alternatively, both of these structures may be stacked.

In the case of the structure in which an electron acceptor is added to an organic compound having a high hole-transport property, as the organic compound having a high hole-transport property, for example, an aromatic amine such as NPB, TPD, TDATA, MTDATA, or 4,4'-bis[N-(spiro-9,9'-bifluoren-2-yl)-N-phenylamino]biphenyl (abbreviation: BSPB), or the like can be used. The substances mentioned here are mainly ones that have a hole mobility of $10^{-6}$ cm$^2$/Vs or higher. Note that any substance other than the above substances may be used as long as they are organic compounds with a hole-transport property higher than an electron-transport property.

Further, as the electron acceptor, 7,7,8,8-tetracyano-2,3,5, 6-tetrafluoroquinodimethane (abbreviation: $F_4$-TCNQ), chloranil, or the like can be used. Alternatively, a transition metal oxide can be used. Further alternatively, an oxide of metals that belong to Group 4 to Group 8 of the periodic table can be used. Specifically, it is preferable to use vanadium oxide, niobium oxide, tantalum oxide, chromium oxide, molybdenum oxide, tungsten oxide, manganese oxide, or rhenium oxide because the electron-accepting property is high. Among these, molybdenum oxide is especially preferable because it is stable in the air, has a low hygroscopic property, and is easily handled.

On the other hand, in the case of the structure in which an electron donor is added to an organic compound having a high electron-transport property, as the organic compound having a high electron-transport property for example, a metal complex having a quinoline skeleton or a benzoquinoline skeleton, such as Alq, Almq$_3$, BeBq$_2$, or BAlq, or the like can be used. Alternatively, it is possible to use a metal complex having an oxazole-based ligand or a thiazole-based ligand, such as Zn(BOX)$_2$ or Zn(BTZ)$_2$. Further alternatively, instead of a metal complex, it is possible to use PBD, OXD-7, TAZ, Bphen, BCP, or the like. The substances mentioned here are mainly ones that have an electron mobility of $10^{-6}$ cm$^2$/Vs or higher. Note that any substance other than the above substances may be used as long as they are organic compounds with an electron-transport property higher than a hole-transport property.

As the electron donor, it is possible to use an alkali metal, an alkaline earth metal, a rare earth metal, a metal belonging to Group 2 or 13 of the periodic table, or an oxide or a carbonate thereof. Specifically, it is preferable to use lithium (Li), cesium (Cs), magnesium (Mg), calcium (Ca), ytterbium (Yb), indium (In), lithium oxide, cesium carbonate, or the like. Alternatively, an organic compound such as tetrathianaphthacene may be used as the electron donor.

Note that forming the charge generation layer (I) 305 by using any of the above materials can suppress an increase in drive voltage caused by the stack of the EL layers.

Figure 3B:
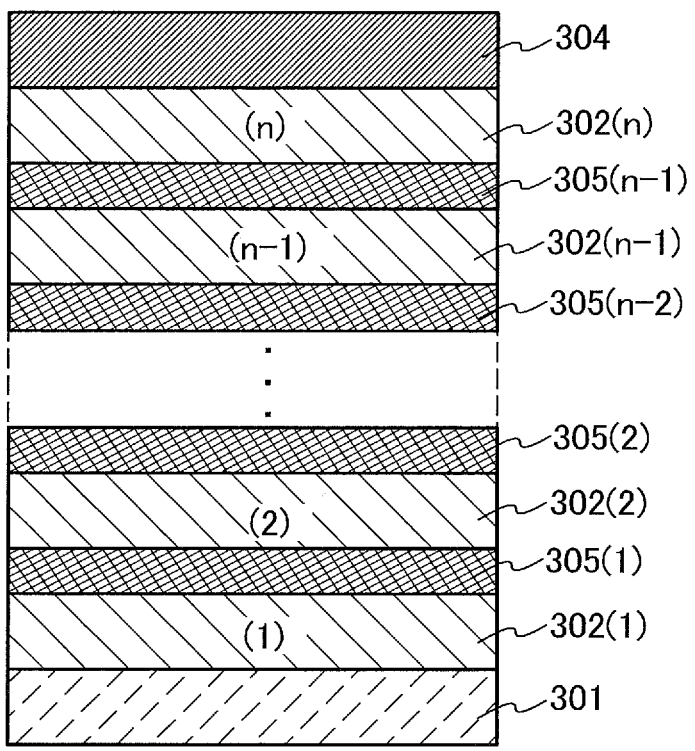

Although this embodiment shows the light-emitting element having two EL layers, the present invention can be similarly applied to a light-emitting element in which n EL layers (302(1) to 302(n)) (n is three or more) are stacked as illustrated in FIG. 3B. In the case where a plurality of EL layers are included between a pair of electrodes as in the light-emitting element according to this embodiment, by providing charge generation layers (I) (305(1) to 305(n−1)) between the EL layers, light emission in a high luminance region can be obtained with current density kept low. Since the current density can be kept low, the element can have a long lifetime. Further, in application to lighting devices, a voltage drop due to resistance of an electrode material can be reduced and accordingly homogeneous light emission in a large area is possible. Moreover, it is possible to achieve a light-emitting device of low power consumption, which can be driven at a low voltage.

By making the EL layers emit light of different colors from each other, the light-emitting element can provide light emission of a desired color as a whole. For example, by forming a light-emitting element having two EL layers such that the emission color of the first EL layer and the emission color of the second EL layer are complementary colors, the light-emitting element can provide white light emission as a whole. Note that the word "complementary" means color relationship in which an achromatic color is obtained when colors are mixed. In other words, when light obtained from a light-emitting substance and light of a complementary color are mixed, white light emission can be obtained.

Further, the same can be applied to a light-emitting element having three EL layers. For example, the light-emitting element as a whole can provide white light emission when the emission color of the first EL layer is red, the emission color of the second EL layer is green, and the emission color of the third EL layer is blue.

Note that the structure described in this embodiment can be combined as appropriate with any of the structures described in the other embodiments.

(Embodiment 5)

In this embodiment, as a light-emitting device utilizing phosphorescence which is one embodiment of the present invention, a light-emitting device using a phosphorescent organometallic iridium complex is described.

Figure 4:
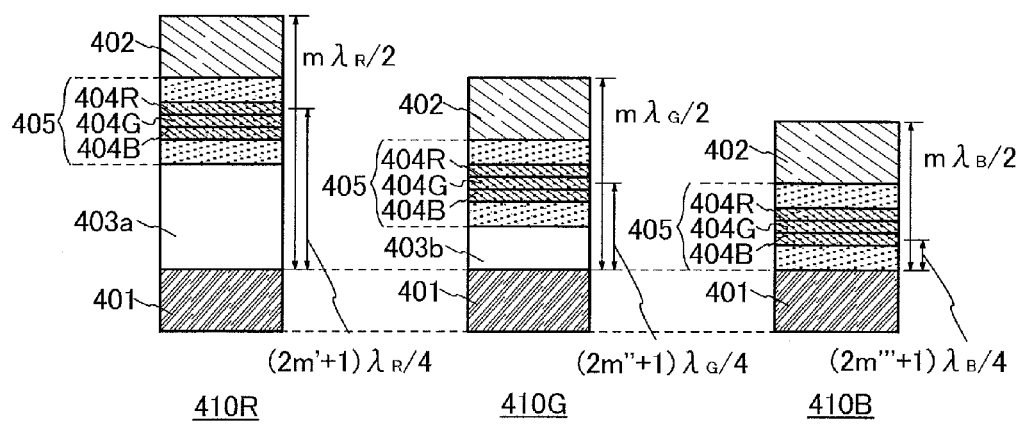
FIG. 4 illustrates a light-emitting device.

A light-emitting device described in this embodiment has a micro optical resonator (microcavity) structure in which a light resonant effect between a pair of electrodes is utilized. The light-emitting device includes a plurality of light-emitting elements each of which has at least an EL layer 405 between a pair of electrodes (a reflective electrode 401 and a semi-transmissive and semi-reflective electrode 402) as illustrated in FIG. 4. Further, the EL layer 405 includes at least light-emitting layers 404 (404R, 404G, and 404B) serving as a light-emitting region and may further include a hole-injection layer, a hole-transport layer, an electron-transport layer, an electron-injection layer, a charge generation layer (E), and the like. Note that the light-emitting layer 404 contains the phosphorescent organometallic iridium complex that is one embodiment of the present invention.

In this embodiment, a light-emitting device is described which includes light-emitting elements (a first light-emitting element (R) 410R, a second light-emitting element (G) 410G, and a third light-emitting element (B) 410B) having different structures as illustrated in FIG. 4.

The first light-emitting element (R) 410R has a structure in which a first transparent conductive layer 403a; an EL layer 405 including a first light-emitting layer (B) 404B, a second light-emitting layer (G) 404G, and a third light-emitting layer (R) 404R in part; and a semi-transmissive and semi-reflective electrode 402 are sequentially stacked over a reflective electrode 401. The second light-emitting element (G) 410G has a structure in which a second transparent conductive layer 403b, the EL layer 405, and the semi-transmissive and semi-reflective electrode 402 are sequentially stacked over the reflective electrode 401. The third light-emitting element (B) 410B has a structure in which the EL layer 405 and the semi-transmissive and semi-reflective electrode 402 are sequentially stacked over the reflective electrode 401.

Note that the reflective electrode 401, the EL layer 405, and the semi-transmissive and semi-reflective electrode 402 are common to the light-emitting elements (the first light-emitting element (R) 410R, the second light-emitting element (G) 410G, and the third light-emitting element (B) 410B). The first light-emitting layer (B) 404B emits light ($\lambda_B$) having a peak in a wavelength region from 420 nm to 480 nm The second light-emitting layer (G) 404G emits light ($\lambda_G$) having a peak in a wavelength region from 500 nm to 550 nm. The third light-emitting layer (R) 404R emits light ($\lambda_R$) having a peak in a wavelength region from 600 nm to 760 nm. Thus, in each of the light-emitting elements (the first light-emitting element (R) 410R, the second light-emitting element (G) 410G, and the third light-emitting element (B) 410B), light emitted from the first light-emitting layer (B) 404B, light emitted from the second light-emitting layer (G) 404G, and light emitted from the third light-emitting layer (R) 404R overlap with each other; accordingly, light having a broad emission spectrum that covers a visible light region can be emitted. Note that the above wavelengths satisfy the relation of $\lambda_B<\lambda_G<\lambda_R$.

Each of the light-emitting elements described in this embodiment has a structure in which the EL layer 405 is interposed between the reflective electrode 401 and the semi-transmissive and semi-reflective electrode 402. Light emitted in all directions from the light-emitting layers included in the EL layer 405 is resonated by the reflective electrode 401 and the semi-transmissive and semi-reflective electrode 402 which function as a micro optical resonator (microcavity). Note that the reflective electrode 401 is formed using a conductive material having reflectivity, and a film whose visible light reflectivity is 40% to 100%, preferably 70% to 100%, and whose resistivity is $1\times10^{-2}$ Ωcm or lower is used. In addition, the semi-transmissive and semi-reflective electrode 402 is formed using a conductive material having reflectivity and a conductive material having a light-transmitting property, and a film whose visible light reflectivity is 20% to 80%, preferably 40% to 70%, and whose resistivity is $1\times10^{-2}$ Ωcm or lower is used.

In this embodiment, the thicknesses of the transparent conductive layers (the first transparent conductive layer 403a and the second transparent conductive layer 403b) provided in the first light-emitting element (R) 410R and the second light-emitting element (G) 410G respectively, are varied between the light-emitting elements, whereby the light-emitting elements differ from each other in the optical path length from the reflective electrode 401 to the semi-transmissive and semi-reflective electrode 402. In other words, in light having a broad emission spectrum, which is emitted from the light-emitting layers of each of the light-emitting elements, light with a wavelength that is resonated between the reflective electrode 401 and the semi-transmissive and semi-reflective electrode 402 can be intensified while light with a wavelength that is not resonated therebetween can be attenuated. Thus, when the elements differ from each other in the optical path length from the reflective electrode 401 to the semi-transmissive and semi-reflective electrode 402, light with different wavelengths can be extracted.

Note that the total thickness from the reflective electrode 401 to the semi-transmissive and semi-reflective electrode 402 is set to $m\lambda_R/2$ (m is a natural number) in the first light-emitting element (R) 410R; the total thickness from the reflective electrode 401 to the semi-transmissive and semi-reflective electrode 402 is set to $m\lambda_G/2$ (m is a natural number) in the second light-emitting element (G) 410G; and the total thickness from the reflective electrode 401 to the semi-transmissive and semi-reflective electrode 402 is set to $m\lambda_B/2$ (m is a natural number) in the third light-emitting element (B) 410B.

In this manner, the light ($\lambda_R$) emitted from the third light-emitting layer (R) 404R included in the EL layer 405 is mainly extracted from the first light-emitting element (R) 410R, the light ($\lambda_G$) emitted from the second light-emitting layer (G) 404G included in the EL layer 405 is mainly extracted from the second light-emitting element (G) 410G, and the light ($\lambda_B$) emitted from the first light-emitting layer (B) 404B included in the EL layer 405 is mainly extracted from the third light-emitting element (B) 410B. Note that the light extracted from each of the light-emitting elements is emitted from the semi-transmissive and semi-reflective electrode 402 side.

Further, strictly speaking, the total thickness from the reflective electrode 401 to the semi-transmissive and semi-reflective electrode 402 can be the total thickness from a reflection region in the reflective electrode 401 to a reflection region in the semi-transmissive and semi-reflective electrode 402. However, it is difficult to precisely determine the positions of the reflection regions in the reflective electrode 401 and the semi-transmissive and semi-reflective electrode 402; therefore, it is presumed that the above effect can be sufficiently obtained wherever the reflection regions may be set in the reflective electrode 401 and the semi-transmissive and semi-reflective electrode 402.

Next, in the first light-emitting element (R) 410R, the optical path length from the reflective electrode 401 to the third light-emitting layer (R) 404R is adjusted to a desired thickness (($2m'+1)\lambda_R/4$, where m' is a natural number); thus, light emitted from the third light-emitting layer (R) 404R can be amplified. Light (first reflected light) that is reflected by the reflective electrode 401 of the light emitted from the third light-emitting layer (R) 404R interferes with light (first incident light) that directly enters the semi-transmissive and semi-reflective electrode 402 from the third light-emitting layer (R) 404R. Therefore, by adjusting the optical path length from the reflective electrode 401 to the third light-emitting layer (R) 404R to the desired value (($2m'+1)\lambda_R/4$, where m' is a natural number), the phases of the first reflected light and the first incident light can be aligned with each other and the light emitted from the third light-emitting layer (R) 404R can be amplified.

Note that strictly speaking, the optical path length from the reflective electrode 401 to the third light-emitting layer (R) 404R can be the optical path length from a reflection region in the reflective electrode 401 to a light-emitting region in the third light-emitting layer (R) 404R. However, it is difficult to precisely determine the positions of the reflection region in the reflective electrode 401 and the light-emitting region in the third light-emitting layer (R) 404R; therefore, it is presumed that the above effect can be sufficiently obtained wherever the reflection region and the light-emitting region may be set in the reflective electrode 401 and the third light-emitting layer (R) 404R, respectively.

Next, in the second light-emitting element (G) 410G, the optical path length from the reflective electrode 401 to the second light-emitting layer (G) 404G is adjusted to a desired thickness (($2m''+1)\lambda_G/4$, where m'' is a natural number); thus, light emitted from the second light-emitting layer (G) 404G can be amplified. Light (second reflected light) that is reflected by the reflective electrode 401 of the light emitted from the second light-emitting layer (G) 404G interferes with light (second incident light) that directly enters the semi-transmissive and semi-reflective electrode 402 from the second light-emitting layer (G) 404G. Therefore, by adjusting the optical path length from the reflective electrode 401 to the second light-emitting layer (G) 404G to the desired value (($2m''+1)\lambda_G/4$, where m'' is a natural number), the phases of the second reflected light and the second incident light can be aligned with each other and the light emitted from the second light-emitting layer (G) 404G can be amplified.

Note that strictly speaking, the optical path length from the reflective electrode 401 to the second light-emitting layer (G) 404G can be the optical path length from a reflection region in the reflective electrode 401 to a light-emitting region in the second light-emitting layer (G) 404G. However, it is difficult to precisely determine the positions of the reflection region in the reflective electrode 401 and the light-emitting region in the second light-emitting layer (G) 404G; therefore, it is presumed that the above effect can be sufficiently obtained wherever the reflection region and the light-emitting region may be set in the reflective electrode 401 and the second light-emitting layer (G) 404G, respectively.

Next, in the third light-emitting element (B) 410B, the optical path length from the reflective electrode 401 to the first light-emitting layer (B) 404B is adjusted to a desired thickness (($2m'''+1)\lambda_B/4$, where m''' is a natural number); thus, light emitted from the first light-emitting layer (B) 404B can be amplified. Light (third reflected light) that is reflected by the reflective electrode 401 of the light emitted from the first light-emitting layer (B) 404B interferes with light (third incident light) that directly enters the semi-transmissive and semi-reflective electrode 402 from the first light-emitting layer (B) 404B. Therefore, by adjusting the optical path length from the reflective electrode 401 to the first light-emitting layer (B) 404B to the desired value (($2m'''+1)\lambda_B/4$, where m''' is a natural number), the phases of the third reflected light and the third incident light can be aligned with each other and the light emitted from the first light-emitting layer (B) 404B can be amplified.

Note that strictly speaking, the optical path length from the reflective electrode 401 to the first light-emitting layer (B) 404B in the third light-emitting element can be the optical path length from a reflection region in the reflective electrode 401 to a light-emitting region in the first light-emitting layer (B) 404B. However, it is difficult to precisely determine the positions of the reflection region in the reflective electrode 401 and the light-emitting region in the first light-emitting layer (B) 404B; therefore, it is presumed that the above effect can be sufficiently obtained wherever the reflection region and the light-emitting region may be set in the reflective electrode 401 and the first light-emitting layer (B) 404B, respectively.

Note that although each of the light-emitting elements in the above-described structure includes a plurality of light-emitting layers in the EL layer, the present invention is not limited thereto; for example, the structure of the tandem light-emitting element which is described in Embodiment 4 can be combined, in which case a plurality of EL layers and a charge generation layer interposed therebetween are provided in one light-emitting element and one or more light-emitting layers are formed in each of the EL layers.

The light-emitting device described in this embodiment has a microcavity structure, in which light with wavelengths which differ depending on the light-emitting elements can be extracted even when they include the same EL layer, so that it is not needed to form light-emitting elements for the colors of R, G, and B. Therefore, the above structure is advantageous for full color display owing to easiness in achieving higher resolution display or the like. In addition, emission intensity with a predetermined wavelength in the front direction can be increased, whereby power consumption can be reduced. The above structure is particularly useful in the case of being applied to a color display (image display device) including pixels of three or more colors but may also be applied to lighting or the like.

(Embodiment 6)

In this embodiment, a light-emitting device including a light-emitting element in which the organometallic complex that is one embodiment of the present invention is used for a light-emitting layer is described.

The light-emitting device can be either a passive matrix light-emitting device or an active matrix light-emitting device. Note that any of the light-emitting elements described in the other embodiments can be applied to the light-emitting device described in this embodiment.

In this embodiment, an active matrix light-emitting device is described with reference to FIGS. 5A and 5B.

Figure 5A:
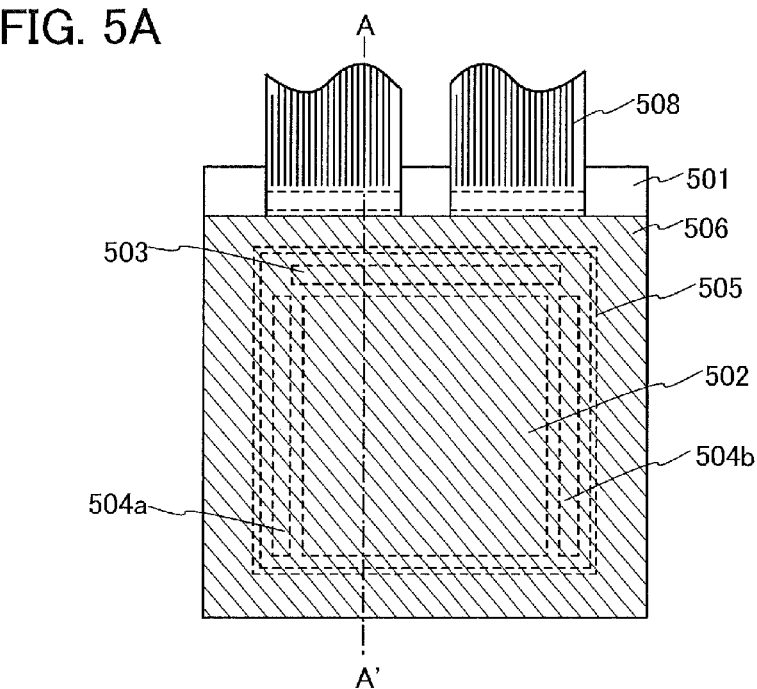
FIGS. 5A and 5B illustrate a light-emitting device.
Figure 5B:
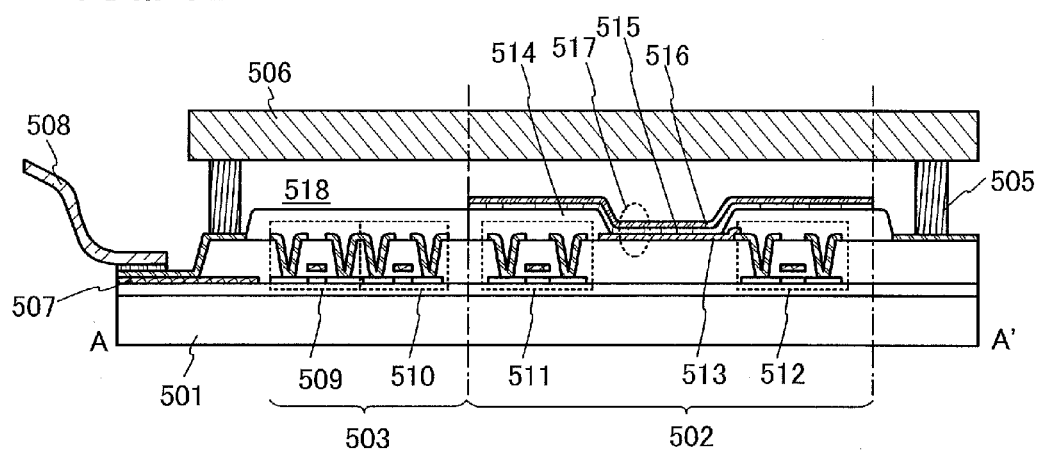

Note that FIG. 5A is a top view illustrating a light-emitting device and FIG. 5B is a cross-sectional view taken along the chain line A-A' in FIG. 5A. The active matrix light-emitting device according to this embodiment includes a pixel portion 502 provided over an element substrate 501, a driver circuit portion (a source line driver circuit) 503, and driver circuit portions (gate line driver circuits) 504 (504a and 504b). The pixel portion 502, the driver circuit portion 503, and the driver circuit portions 504 are sealed between the element substrate 501 and the sealing substrate 506 with a sealant 505.

In addition, a lead wiring 507 is provided over the element substrate 501. The lead wiring 507 is provided for connecting an external input terminal through which a signal (e.g., a video signal, a clock signal, a start signal, and a reset signal) or a potential from the outside is transmitted to the driver circuit portion 503 and the driver circuit portions 504. Here is shown an example in which a flexible printed circuit (FPC) 508 is provided as the external input terminal. Although the FPC 508 is illustrated alone, this FPC may be provided with a printed wiring board (PWB). The light-emitting device in the present specification includes, in its category, not only the light-emitting device itself but also the light-emitting device provided with the FPC or the PWB.

Next, a cross-sectional structure is described with reference to FIG. 5B. The driver circuit portion and the pixel portion are formed over the element substrate 501; here are illustrated the driver circuit portion 503 which is the source line driver circuit and the pixel portion 502.

The driver circuit portion 503 is an example where a CMOS circuit is formed, which is a combination of an n-channel TFT 509 and a p-channel TFT 510. Note that a circuit included in the driver circuit portion may be formed using various CMOS circuits, PMOS circuits, or NMOS circuits. Although this embodiment shows a driver integrated type in which the driver circuit is formed over the substrate, the driver circuit is not necessarily formed over the substrate, and may be formed outside the substrate.

The pixel portion 502 is formed of a plurality of pixels each of which includes a switching TFT 511, a current control TFT 512, and a first electrode (anode) 513 which is electrically connected to a wiring (a source electrode or a drain electrode) of the current control TFT 512. Note that an insulator 514 is formed to cover end portions of the first electrode (anode) 513. In this embodiment, the insulator 514 is formed using a positive photosensitive acrylic resin.

The insulator 514 preferably has a curved surface with curvature at an upper end portion or a lower end portion thereof in order to obtain favorable coverage by a film which is to be stacked over the insulator 514. For example, in the case of using a positive photosensitive acrylic resin as a material for the insulator 514, the insulator 514 preferably has a curved surface with a curvature radius (0.2 µm to 3 µm) at the upper end portion. Note that the insulator 514 can be formed using either a negative photosensitive resin or a positive photosensitive resin. The material of the insulator 514 is not limited to an organic compound and an inorganic compound such as silicon oxide or silicon oxynitride can also be used.

An EL layer 515 and a second electrode (cathode) 516 are stacked over the first electrode (anode) 513. In the EL layer 515, at least a light-emitting layer is provided which contains the organometallic complex that is one embodiment of the present invention. Further, in the EL layer 515, a hole-injection layer, a hole-transport layer, an electron-transport layer, an electron-injection layer, a charge generation layer, and the like can be provided as appropriate in addition to the light-emitting layer.

A light-emitting element 517 is formed of a stacked structure of the first electrode (anode) 513, the EL layer 515, and the second electrode (cathode) 516. For the first electrode (anode) 513, the EL layer 515, and the second electrode (cathode) 516, the materials described in Embodiment 2 can be used. Although not illustrated, the second electrode (cathode) 516 is electrically connected to the FPC 508 which is an external input terminal.

Although the cross-sectional view of FIG. 5B illustrates only one light-emitting element 517, a plurality of light-emitting elements are arranged in matrix in the pixel portion 502. Light-emitting elements which provide three kinds of light emission (R, G, and B) are selectively formed in the pixel portion 502, whereby a light-emitting device capable of full color display can be fabricated. Alternatively, a light-emitting device which is capable of full color display may be fabricated by a combination with color filters.

Further, the sealing substrate 506 is attached to the element substrate 501 with the sealant 505, whereby the light-emitting element 517 is provided in a space 518 surrounded by the element substrate 501, the sealing substrate 506, and the sealant 505. The space 518 may be filled with an inert gas (such as nitrogen or argon), or the sealant 505.

An epoxy-based resin is preferably used for the sealant 505. It is preferable that such a material do not transmit moisture or oxygen as much as possible. As the sealing substrate 506, a glass substrate, a quartz substrate, or a plastic substrate formed of fiberglass reinforced plastic (FRP), polyvinyl fluoride) (PVF), polyester, acrylic, or the like can be used.

As described above, an active matrix light-emitting device can be obtained.

Note that the structure described in this embodiment can be combined as appropriate with any of the structures described in the other embodiments.

(Embodiment 7)

In this embodiment, examples of a variety of electronic devices which are completed using a light-emitting device are described with reference to FIGS. 6A to 6D and FIGS. 7A to 7C. To the light-emitting device, the organometallic complex that is one embodiment of the present invention is applied.

Examples of the electronic devices to which the light-emitting device is applied are a television device (also referred to as television or television receiver), a monitor of a computer or the like, a camera such as a digital camera or a digital video camera, a digital photo frame, a mobile phone (also referred to as cellular phone or cellular phone device), a portable game machine, a portable information terminal, an audio reproducing device, and a large-sized game machine such as a pachinko machine. Specific examples of these electronic devices are illustrated in FIGS. 6A to 6D.

Figure 6A:
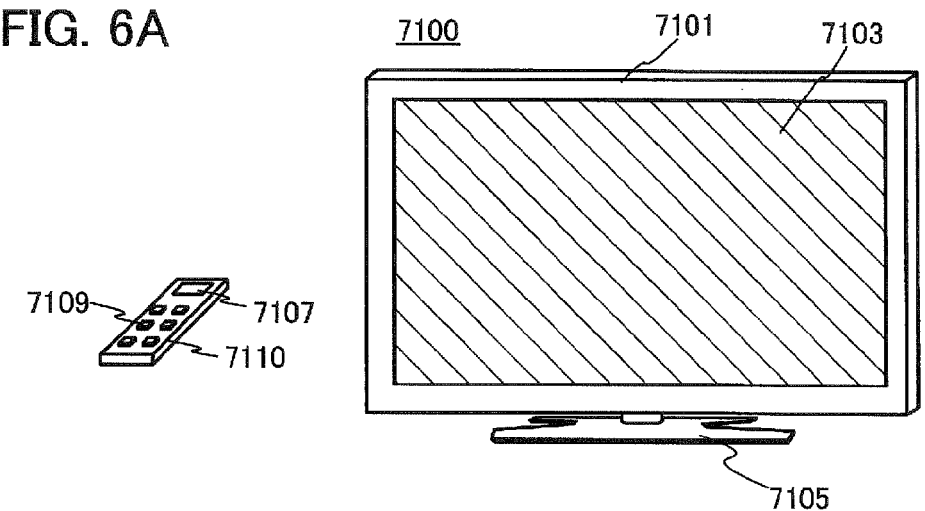
FIGS. 6A to 6D illustrate electronic devices.

FIG. 6A illustrates an example of a television set. In a television set 7100, a display portion 7103 is incorporated in a housing 7101. Images can be displayed on the display portion 7103, and the light-emitting device can be used for the display portion 7103. In addition, here, the housing 7101 is supported by a stand 7105.

Operation of the television set 7100 can be performed with an operation switch of the housing 7101 or a separate remote controller 7110. With operation keys 7109 of the remote controller 7110, channels and volume can be controlled and images displayed on the display portion 7103 can be controlled. Furthermore, the remote controller 7110 may be provided with a display portion 7107 for displaying data output from the remote controller 7110.

Note that the television set 7100 is provided with a receiver, a modem, and the like. With the receiver, a general television broadcast can be received. Furthermore, when the television set 7100 is connected to a communication network by wired or wireless connection via the modem, one-way (from a transmitter to a receiver) or two-way (between a transmitter and a receiver, between receivers, or the like) data communication can be performed.

Figure 6B:
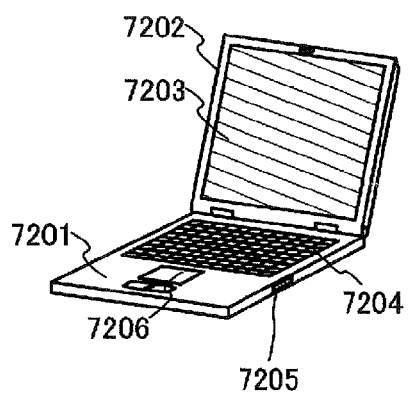

FIG. 6B illustrates a computer having a main body 7201, a housing 7202, a display portion 7203, a keyboard 7204, an external connection port 7205, a pointing device 7206, and the like. Note that this computer is manufactured using the light-emitting device for the display portion 7203.

Figure 6C:
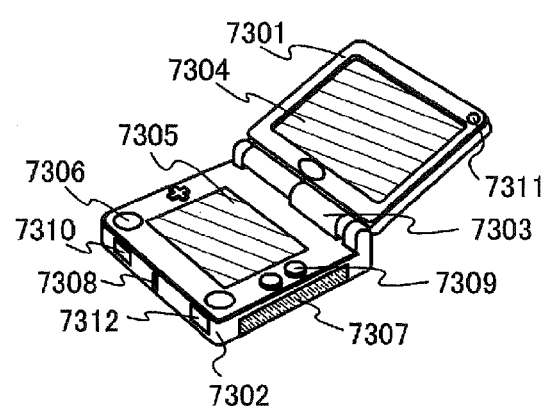

FIG. 6C illustrates a portable game machine having two housings, a housing 7301 and a housing 7302, which are connected with a joint portion 7303 so that the portable game machine can be opened or folded. A display portion 7304 is incorporated in the housing 7301, and a display portion 7305 is incorporated in the housing 7302. In addition, the portable game machine illustrated in FIG. 6C includes a speaker portion 7306, a recording medium insertion portion 7307, an LED lamp 7308, input means (an operation key 7309, a connection terminal 7310, a sensor 7311 (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared rays), and a microphone 7312), and the like. Needless to say, the structure of the portable game machine is not limited to the above as long as the light-emitting device is used for at least one of the display portion 7304 and the display portion 7305, and may include other accessories as appropriate. The portable game machine illustrated in FIG. 6C has a function of reading out a program or data stored in a storage medium to display it on the display portion, and a function of sharing information with another portable game machine by wireless communication. The functions of the portable game machine illustrated in FIG. 6C are not limited to these, and the portable game machine can have a variety of functions.

Figure 6D:
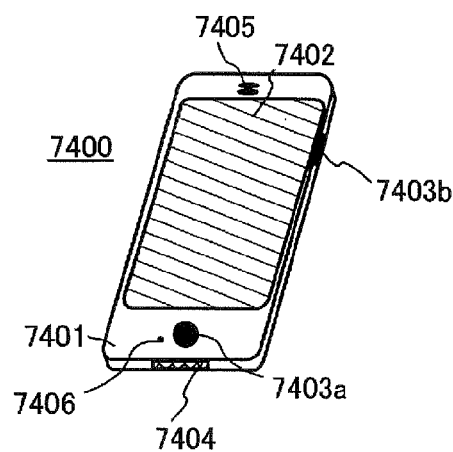

FIG. 6D illustrates an example of a mobile phone. A mobile phone 7400 is provided with a display portion 7402 incorporated in a housing 7401, operation buttons 7403a and 7403b, an external connection port 7404, a speaker 7405, a microphone 7406, and the like. Note that the mobile phone 7400 is manufactured using the light-emitting device for the display portion 7402.

When the display portion 7402 of the mobile phone 7400 illustrated in FIG. 6D is touched with a finger or the like, data can be input to the mobile phone 7400. Further, operations such as making a call and composing an e-mail can be performed by touching the display portion 7402 with a finger or the like.

There are mainly three screen modes of the display portion 7402. The first mode is a display mode mainly for displaying images. The second mode is an input mode mainly for inputting data such as text. The third mode is a display-and-input mode in which two modes of the display mode and the input mode are combined.

For example, in the case of making a call or composing an e-mail, a text input mode mainly for inputting text is selected for the display portion 7402 so that text displayed on the screen can be input. In this case, it is preferable to display a keyboard or number buttons on almost the entire screen of the display portion 7402.

When a detection device including a sensor for detecting inclination, such as a gyroscope or an acceleration sensor, is provided inside the mobile phone 7400, display on the screen of the display portion 7402 can be automatically switched by determining the orientation of the mobile phone 7400 (whether the mobile phone is placed horizontally or vertically for a landscape mode or a portrait mode).

The screen modes are switched by touching the display portion 7402 or operating the operation buttons 7403$a$ of the housing 7401. The screen modes can also be switched depending on the kind of image displayed on the display portion 7402. For example, when a signal of an image displayed on the display portion is a signal of moving image data, the screen mode is switched to the display mode. When the signal is a signal of text data, the screen mode is switched to the input mode.

Moreover, in the input mode, when input by touching the display portion 7402 is not performed for a certain period while a signal detected by an optical sensor in the display portion 7402 is detected, the screen mode may be controlled so as to be switched from the input mode to the display mode.

The display portion 7402 may function as an image sensor. For example, an image of a palm print, a fingerprint, or the like is taken when the display portion 7402 is touched with the palm or the finger, whereby personal authentication can be performed. Further, by providing a backlight or a sensing light source which emits near-infrared light in the display portion, an image of a finger vein, a palm vein, or the like can be taken.

Figure 7A:
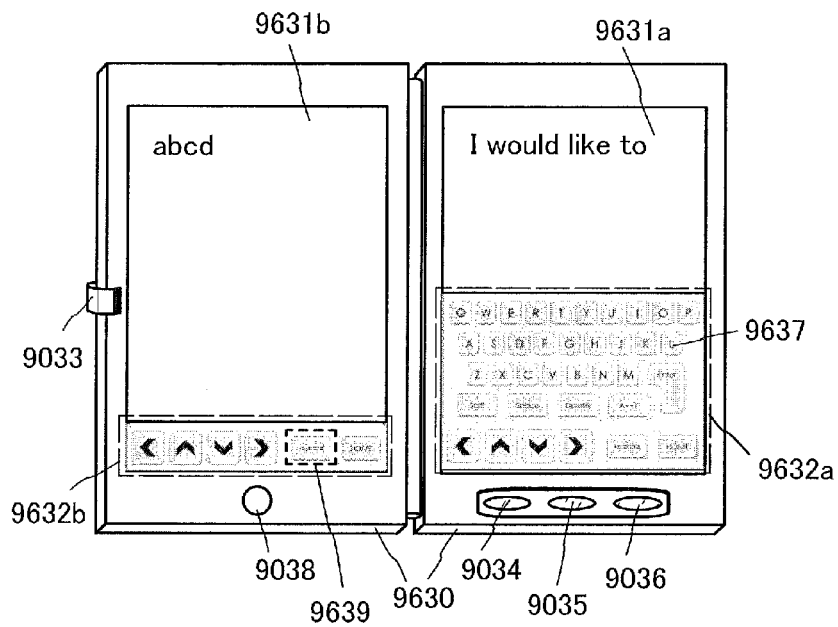
FIGS. 7A to 7C illustrate an electronic device.
Figure 7B:
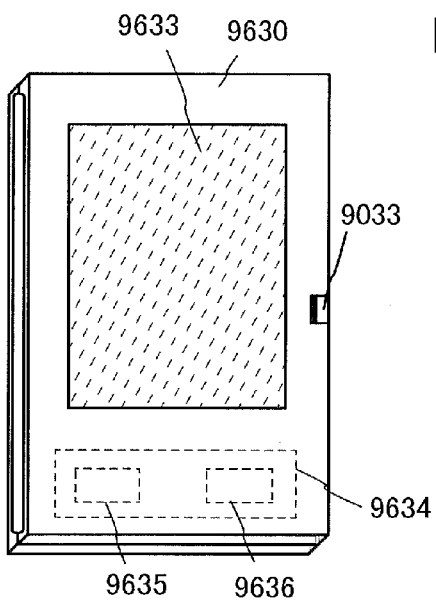

FIGS. 7A and 7B illustrate a foldable tablet terminal. The tablet terminal is opened in FIG. 7A. The tablet terminal includes a housing 9630, a display portion 9631$a$, a display portion 9631$b$, a display mode switch 9034, a power switch 9035, a power saver switch 9036, a clasp 9033, and an operation switch 9038. The tablet terminal is manufactured using the light-emitting device for either the display portion 9631$a$ or the display portion 9631$b$ or both.

Part of the display portion 9631$a$ can be a touch panel region 9632$a$ and data can be input when a displayed operation key 9637 is touched. Although a structure in which a half region in the display portion 9631$a$ has only a display function and the other half region also has a touch panel function is shown as an example, the display portion 9631$a$ is not limited to the structure. The whole region in the display portion 9631$a$ may have a touch panel function. For example, the display portion 9631$a$ can display keyboard buttons in the whole region to be a touch panel, and the display portion 9631$b$ can be used as a display screen.

As in the display portion 9631$a$, part of the display portion 9631$b$ can be a touch panel region 9632$b$. When a keyboard display switching button 9639 displayed on the touch panel is touched with a finger, a stylus, or the like, a keyboard can be displayed on the display portion 9631$b$.

Touch input can be performed in the touch panel region 9632$a$ and the touch panel region 9632$b$ at the same time.

The display mode switch 9034 can switch the display between portrait mode, landscape mode, and the like, and between monochrome display and color display, for example. The power saver switch 9036 can control display luminance in accordance with the amount of external light in use of the tablet terminal detected by an optical sensor incorporated in the tablet terminal. In addition to the optical sensor, another detection device including a sensor for detecting inclination, such as a gyroscope or an acceleration sensor, may be incorporated in the tablet terminal.

Note that FIG. 7A shows an example in which the display portion 9631$a$ and the display portion 9631$b$ have the same display area; however, without limitation thereon, one of the display portions may be different from the other display portion in size and display quality. For example, higher definition images may be displayed on one of the display portions 9631$a$ and 9631$b$.

The tablet terminal is closed in FIG. 7B. The tablet terminal includes the housing 9630, a solar cell 9633, a charge and discharge control circuit 9634, a battery 9635, and a DCDC converter 9636. In FIG. 7B, a structure including the battery 9635 and the DCDC converter 9636 is illustrated as an example of the charge and discharge control circuit 9634.

Since the tablet terminal is foldable, the housing 9630 can be closed when the tablet terminal is not used. As a result, the display portion 9631$a$ and the display portion 9631$b$ can be protected; thus, a tablet terminal which has excellent durability and excellent reliability in terms of long-term use can be provided.

In addition, the tablet terminal illustrated in FIGS. 7A and 7B can have a function of displaying a variety of kinds of data (e.g., a still image, a moving image, and a text image), a function of displaying a calendar, a date, the time, or the like on the display portion, a touch-input function of operating or editing the data displayed on the display portion by touch input, a function of controlling processing by a variety of kinds of software (programs), and the like.

The solar cell 9633 provided on a surface of the tablet terminal can supply power to the touch panel, the display portion, a video signal processing portion, or the like. Note that the solar battery 9633 can be provided on one or both surfaces of the housing 9630, so that the battery 9635 can be charged efficiently. The use of a lithium ion battery as the battery 9635 is advantageous in downsizing or the like.

Figure 7C:
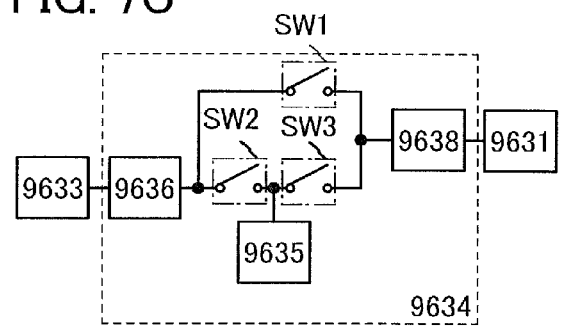

The structure and the operation of the charge and discharge control circuit 9634 illustrated in FIG. 7B will be described with reference to a block diagram in FIG. 7C. The solar cell 9633, the battery 9635, the DCDC converter 9636, a converter 9638, switches SW1 to SW3, and the display portion 9631 are illustrated in FIG. 7C, and the battery 9635, the DCDC converter 9636, the converter 9638, and the switches SW1 to SW3 correspond to the charge and discharge control circuit 9634 illustrated in FIG. 7B.

First, an example of the operation in the case where power is generated by the solar cell 9633 using external light is described. The voltage of power generated by the solar cell 9633 is stepped up or down by the DCDC converter 9636 so that the power has a voltage for charging the battery 9635.

Then, when the power from the solar cell 9633 is used for the operation of the display portion 9631, the switch SW1 is turned on and the voltage of the power is stepped up or down by the converter 9638 so as to be a voltage needed for the display portion 9631. In addition, when display on the display portion 9631 is not performed, the switch SW1 is turned off and the switch SW2 is turned on so that the battery 9635 may be charged.

Note that the solar cell 9633 is described as an example of a power generation means; however, without limitation thereon, the battery 9635 may be charged using another power generation means such as a piezoelectric element or a thermoelectric conversion element (Peltier element). For example, the battery 9635 may be charged with a non-contact power transmission module which is capable of charging by transmitting and receiving power by wireless (without contact), or another charge means used in combination.

It is needless to say that one embodiment of the present invention is not limited to the electronic device illustrated in FIGS. 7A to 7C as long as the display portion described in this embodiment is included.

As described above, the electronic devices can be obtained by application of the light-emitting device that is one embodiment of the present invention. The light-emitting device has a remarkably wide application range, and can be applied to electronic devices in a variety of fields.

Note that the structure described in this embodiment can be combined as appropriate with any of the structures described in the other embodiments.

(Embodiment 8)

In this embodiment, examples of a lighting device to which a light-emitting device including the organometallic complex that is one embodiment of the present invention is applied are described with reference to FIG. 8.

Figure 8:
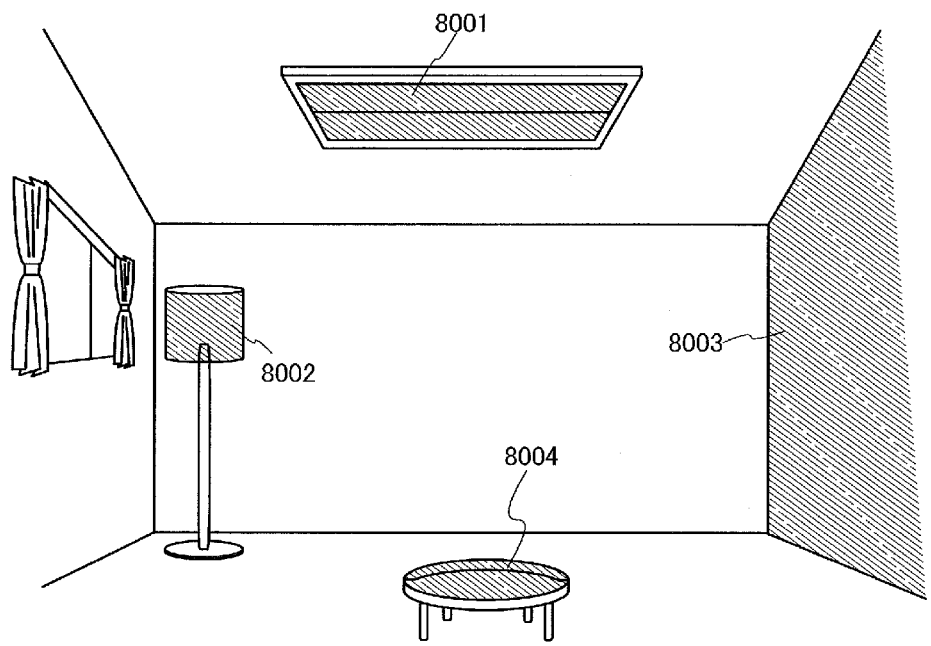
FIG. 8 illustrates lighting devices.

FIG. 8 illustrates an example in which the light-emitting device is used as an indoor lighting device 8001. Since the light-emitting device can have a large area, it can be used for a lighting device having a large area. In addition, a lighting device 8002 in which a light-emitting region has a curved surface can also be obtained with the use of a housing with a curved surface. A light-emitting element included in the light-emitting device described in this embodiment is in a thin film form, which allows the housing to be designed more freely. Therefore, the lighting device can be elaborately designed in a variety of ways. Further, a wall of the room may be provided with a large-sized lighting device 8003.

Moreover, when the light-emitting device is used for a table by being used as a surface of a table, a lighting device 8004 which has a function as a table can be obtained. When the light-emitting device is used as part of other furniture, a lighting device which has a function as the furniture can be obtained.

In this manner, a variety of lighting devices to which the light-emitting device is applied can be obtained. Note that such lighting devices are also embodiments of the present invention.

Note that the structure described in this embodiment can be combined as appropriate with any of the structures described in the other embodiments.

EXAMPLE 1

SYNTHESIS EXAMPLE 1

In this example, a synthesis method of a phosphorescent organometallic iridium complex tris{2-[5-(2-methylphenyl)-4-phenyl-4H-1,2,4-triazol-3-yl-κN2]phenyl-κC}iridium (III) (abbreviation: [Ir(mpptz)$_3$]), which is one embodiment of the present invention represented by Structural Formula (100) in Embodiment 1, is described. A structure of [Ir(mpptz)$_3$] (abbreviation) is shown below.

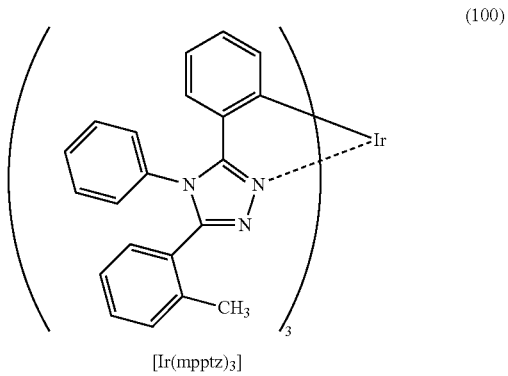

[Ir(mpptz)$_3$]

Step 1: Synthesis of
N-Benzoyl-N'-2-methylbenzoylhydrazide

First, 15.0 g (110.0 mmol) of benzoylhydrazine and 75 ml of N-methyl-2-pyrrolidinone (NMP) were put into a 300-ml three-neck flask and stirred while being cooled with ice. To this mixed solution, a mixed solution of 17.0 g (110.0 mmol) of o-toluoyl chloride and 15 ml of N-methyl-2-pyrrolidinone (NMP) was slowly added dropwise. After the addition, the mixture was stirred at room temperature for 24 hours. After reaction for the predetermined time, this reacted solution was slowly added to 500 ml of water, so that a white solid was precipitated. The precipitated solid was subjected to ultrasonic cleaning in which water and 1M hydrochloric acid were used alternately. Then, ultrasonic cleaning using hexane was performed, so that 19.5 g of a white solid of N-benzoyl-N'-2-methylbenzoylhydrazide was obtained in a yield of 70%. A synthesis scheme of Step 1 is shown in (a-1).

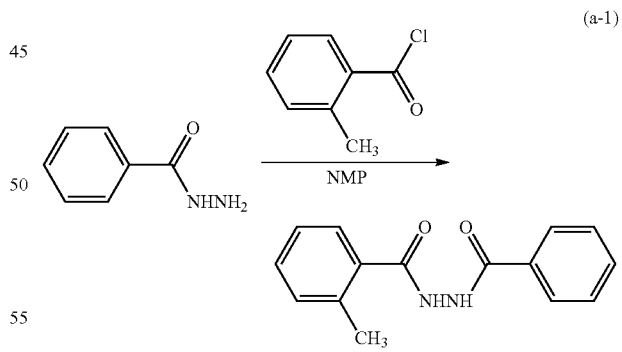

Step 2: Synthesis of [chloro(2-methylphenyl)methanone][chloro(phenyl)methylidene]hydrazone Next, 12.0 g (47.2 mmol) of N-benzoyl-N'-2-methylbenzoylhydrazide obtained in Step 1 and 200 ml of toluene were put into a 500-ml three-neck flask. To this mixed solution, 19.4 g (94.4 mmol) of phosphorus pentachloride was added and the mixture was heated and stirred at 120° C. for 6 hours.

After reaction for the predetermined time, the reacted solution was slowly poured into 200 ml of water and the mixture was stirred for 1 hour. After the stirring, an organic layer and an aqueous layer were separated, and the organic layer was washed with water and a saturated aqueous solution of sodium hydrogen carbonate. After the washing, the organic layer was dried with anhydrous magnesium sulfate. The magnesium sulfate was removed from this mixture by gravity filtration, and the filtrate was concentrated; thus, 12.6 g of a brown liquid of [chloro(2-methylphenyl)methanone][chloro(phenyl)methylidene]hydrazone was obtained in a yield of 92%. A synthesis scheme of Step 2 is shown in (a-2).

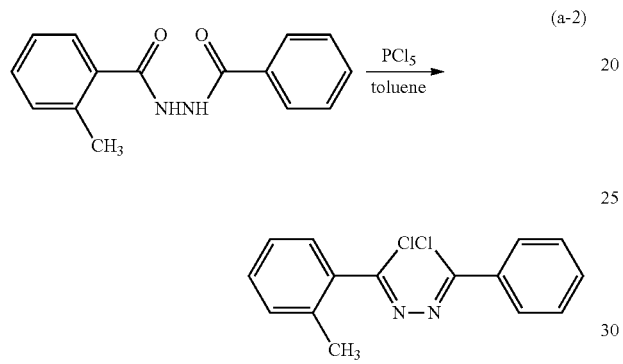

(a-2)

Step 3: Synthesis of 3-(2-Methylphenyl)-4,5-diphenyl-4H-1,2,4-triazole (abbreviation: Hmpptz)

Then, 5.1 g (17.6 mmol) of [chloro(2-methylphenyl)methanone][chloro(phenyl)methylidene]hydrazone obtained in Step 2, 60 ml of dimethylaniline, and 4.9 g (52.8 mmol) of aniline were put into a 500-ml recovery flask and heated and stirred at 120° C. for 7 hours. After the stirring, the reacted solution was added to 1N hydrochloric acid and the mixture was stirred for 30 minutes. Then, an organic layer was extracted with dichloromethane. This organic layer was washed with a saturated aqueous solution of sodium hydrogen carbonate and saturated brine. Purification by column chromatography was then performed. A mixed solvent of toluene and ethyl acetate in a ratio of 1:1 was used as a developing solvent. The obtained fraction was concentrated to give 3.4 g of a white solid of Hmpptz in a yield of 63%. A synthesis scheme of Step 3 is shown in (a-3).

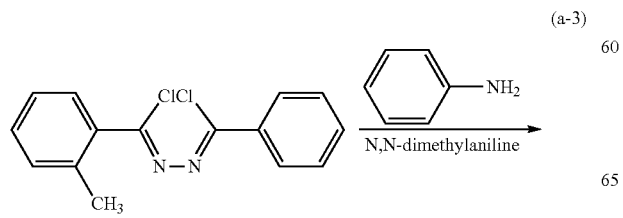

(a-3)

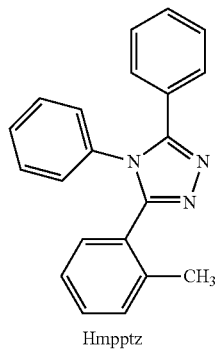

Hmpptz

Step 4: Synthesis of Tris{2-[5-(2-methylphenyl)-4-phenyl-4H-1,2,4-triazol-3-yl-κN2]phenyl-κC}iridium(III) (abbreviation: [Ir(mpptz)₃])

Then, 2.9 g (9.3 mmol) of Hmpptz, which was the ligand obtained in Step 3, and 1.6 g (3.1 mmol) of tris(acetylacetonato)iridium(III) were put into a container for high-temperature heating, and degasification was carried out. The mixture in the reaction container was heated and stirred at 250° C. for 48 hours under Ar flow. After reaction for the predetermined time, the reacted mixture was dissolved in dichloromethane and purified by flash column chromatography. A mixed solvent of dichloromethane and ethyl acetate in a ratio of 10:1 was used as a developing solvent. The obtained fraction was concentrated and the obtained solid was recrystallized with ethyl acetate, so that 1.0 g of a green powder of [Ir(mpptz)₃], the organometallic complex which is one embodiment of the present invention, was obtained in a yield of 29%. A synthesis scheme of Step 4 is shown in (a-4).

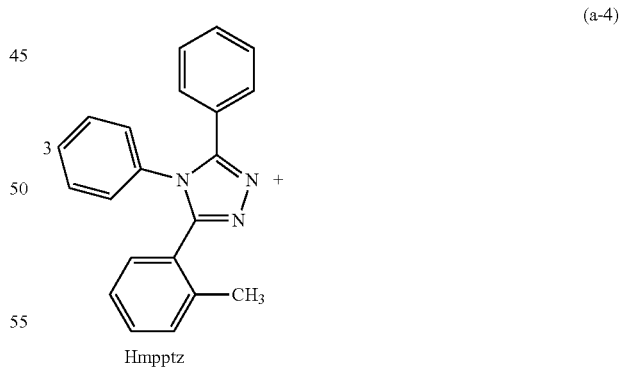

(a-4)

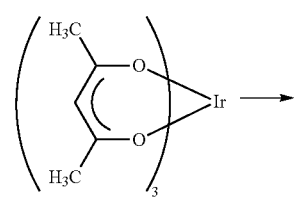

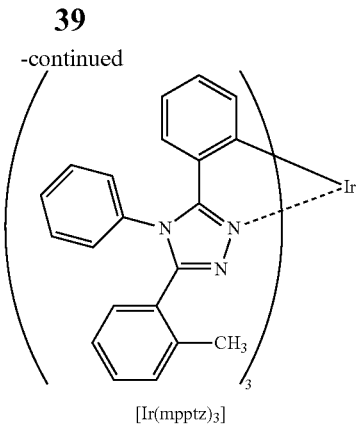

[Ir(mpptz)₃]

Figure 9:
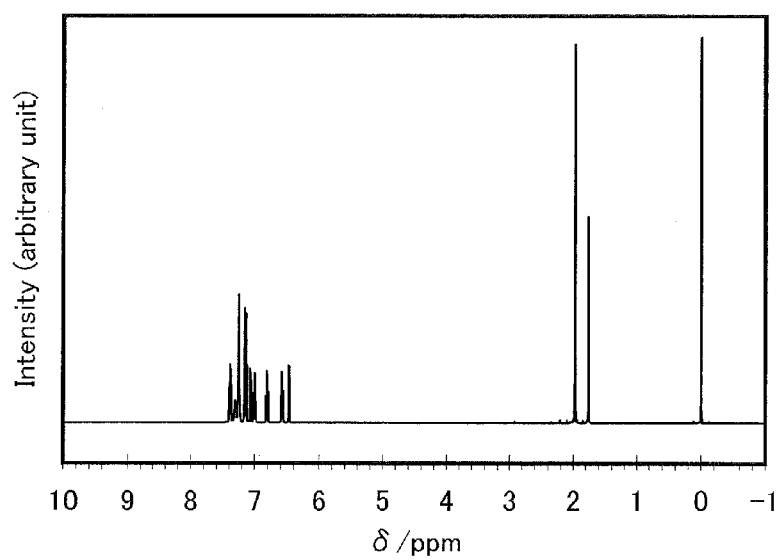
FIG. 9 shows a $^1$H-NMR chart of a phosphorescent organometallic iridium complex represented by Structural Formula (100).

An analysis result by nuclear magnetic resonance (¹H-NMR) spectroscopy of the green powder obtained in Step 4 is described below. FIG. 9 shows the ¹H-NMR chart. These results revealed that [Ir(mpptz)₃] (abbreviation), the organometallic complex which is one embodiment of the present invention represented by Structural Formula (100), was obtained in Synthesis Example 1.

1H-NMR. δ(CDCl₃): 1.98 (s, 3H), 6.46-6.48 (d, 1H), 6.57-6.61 (t, 1H), 6.79-6.82 (t, 1H), 6.98-7.02 (t, 1H), 7.05-7.07 (d, 1H), 7.12-7.17 (q, 3H), 7.23-7.32 (m, 3H), 7.38-7.40 (t, 2H).

Figure 10:
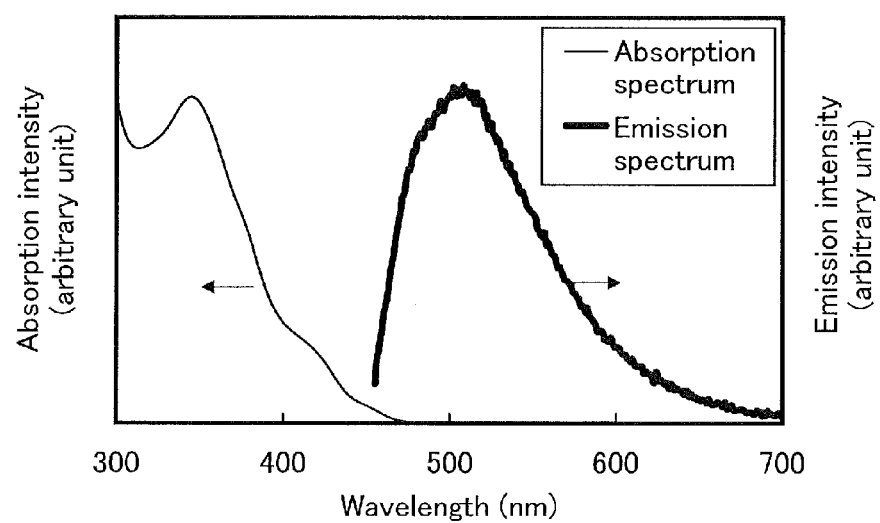
FIG. 10 shows an ultraviolet-visible absorption spectrum and an emission spectrum of a phosphorescent organometallic iridium complex represented by Structural Formula (100).

Next, [Ir(mpptz)₃] (abbreviation) was analyzed by ultraviolet-visible (UV) absorption spectroscopy. The UV spectrum was measured with an ultraviolet-visible spectrophotometer (V550 type manufactured by Japan Spectroscopy Corporation) using a dichloromethane solution (1.135 mmol/L) at room temperature. Further, an emission spectrum of [Ir(mpptz)₃] (abbreviation) was measured. The emission spectrum was measured by a fluorescence spectrophotometer (FS920 manufactured by Hamamatsu Photonics K. K.) using a degassed dichloromethane solution (1.135 mmol/L) at room temperature. FIG. 10 shows the measurement results. The horizontal axis represents wavelength and the vertical axes represent absorption intensity and emission intensity.

As shown in FIG. 10, [Ir(mpptz)₃] (abbreviation), the phosphorescent organometallic iridium complex that is one embodiment of the present invention, has an emission peak at 512 nm, and green light emission was observed from the dichloromethane solution.

Further, tris{2-[5-(2-methylphenyl)-4-phenyl-4H-1,2,4-triazol-3-yl-κN2]phenyl-κC}iridium(III) (abbreviation: [Ir(mpptz)₃]) obtained in this example was analyzed by liquid chromatography mass spectrometry (LC/MS).

The LC/MS analysis was carried out with Acquity UPLC (produced by Waters Corporation) and Xevo G2 T of MS (produced by Waters Corporation).

In the MS analysis, ionization was carried out by an electrospray ionization (ESI) method. At this time, the capillary voltage and the sample cone voltage were set to 3.0 kV and 30 V, respectively, and detection was performed in a positive mode. A component with m/z of 1124 which underwent the ionization under the above-described conditions was collided with an argon gas in a collision cell to dissociate into product ions. Energy (collision energy) for the collision with argon was 50 eV. The mass range for the measurement was m/z=30 to 1300.

Figure 35:
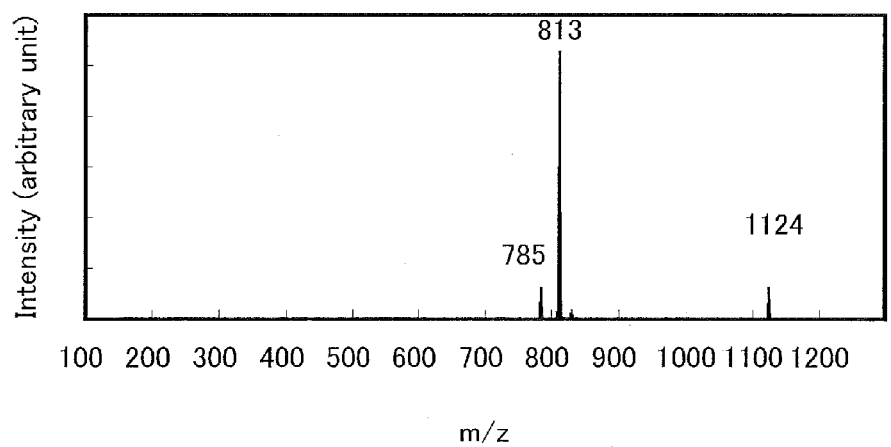
FIG. 35 shows LC/MS measurement results of a phosphorescent organometallic iridium complex represented by Structural Formula (100).

The detection result of the dissociated product ions by time-of-flight (TOF) MS are shown in FIG. 35.

The results in FIG. 35 show that product ions of [Ir(mpptz)₃] (abbreviation), the organometallic iridium complex that is one embodiment of the present invention represented by Structural Formula (100), were detected mainly around m/z 813 and m/z 785. Note that the results in FIG. 35 show characteristics derived from [Ir(mpptz)₃] (abbreviation) and therefore can be regarded as important data for identifying [Ir(mpptz)₃] (abbreviation) contained in the mixture.

EXAMPLE 2

SYNTHESIS EXAMPLE 2

In this example, a synthesis method of a phosphorescent organometallic iridium complex tris {2-[5-(2-methylphenyl)-4-(2,6-dimethylphenyl)-4H-1,2,4-triazol-3-yl-κN2]phenyl-κC}iridium(III) (abbreviation: [Ir(mpptz-dmp)₃]), which is one embodiment of the present invention represented by Structural Formula (101) in Embodiment 1, is described. A structure of [Ir(mpptz-dmp)₃] (abbreviation) is shown below.

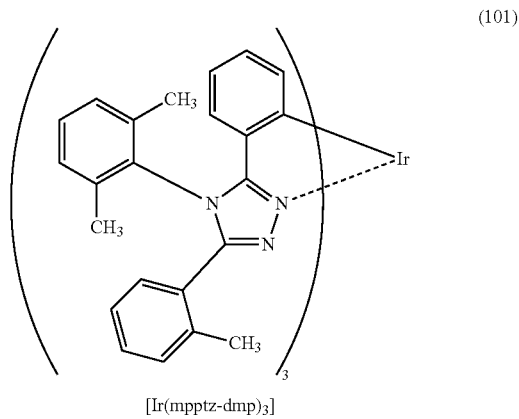

(101)

[Ir(mpptz-dmp)₃]

Step 1: Synthesis of 3-(2-Methylphenyl)-4-(2,6-dimethylphenyl)-5-phenyl-4H-1,2,4-triazole (abbreviation: Hmpptz-dmp First, 12.6 g (43.3 mmol) of [chloro(2-methylphenyl)methanone][chloro(phenyl)methylidene]hydrazone obtained in Step 2 in Synthesis Example 1, 15.7 g (134.5 mmol) of 2,6-dimethylaniline, and 100 ml of N,N-dimethylaniline were put into a 500-ml recovery flask and heated and stirred at 120° C. for 20 hours. After reaction for the predetermined time, this reacted solution was slowly added to 200 ml of 1N hydrochloric acid. Dichloromethane was added to this solution and an objective substance was extracted to an organic layer. The obtained organic layer was washed with water and an aqueous solution of sodium hydrogen carbonate, and was dried with magnesium sulfate. The magnesium sulfate was removed by gravity filtration, and the obtained filtrate was concentrated to give a black liquid. This liquid was purified by silica gel column chromatography. A mixed solvent of ethyl acetate and hexane in a ratio of 1:5 was used as a developing solvent. The obtained fraction was concentrated to give a white solid. This solid was recrystallized with ethyl acetate to give 4.5 g of a white solid of Hmpptz-dmp in a yield of 31%. A synthesis scheme of Step 1 is shown in (b-1).

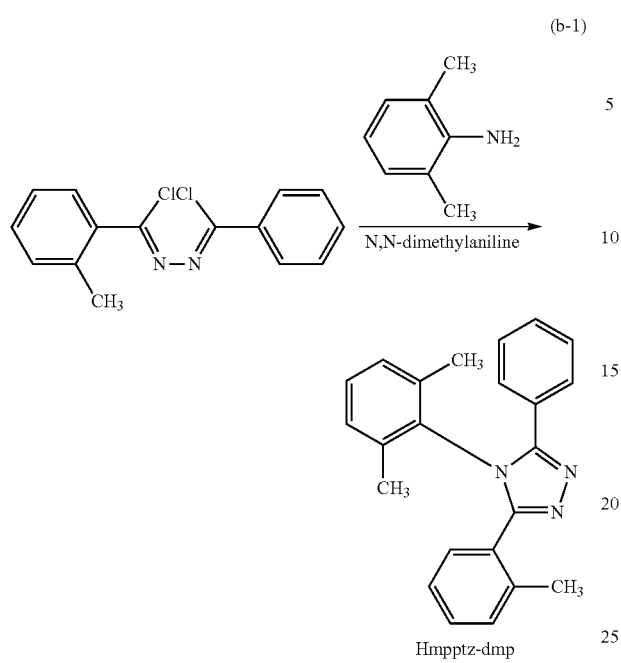

Hmpptz-dmp

Step 2: Synthesis of Tris{2-[5-(2-methylphenyl)-4-(2,6-dimethylphenyl)-4H-1,2,4-triazol-3-yl-κN2]phenyl-κC}iridium(III) (abbreviation: [Ir(mpptz-dmp)₃]

Then, 2.5 g (7.4 mmol) of Hmpptz-dmp, which was the ligand obtained in Step 1, and 0.7 g (1.5 mmol) of tris(acetylacetonato)iridium(III) were put into a container for high-temperature heating, and degasification was carried out. The mixture in the reaction container was heated and stirred at 250° C. for 48 hours under Ar flow. After reaction for the predetermined time, the obtained solid was washed with dichloromethane, and an insoluble green solid was obtained by suction filtration. This solid was dissolved in toluene and filtered through a stack of alumina and Celite. The obtained fraction was concentrated to give a green solid. This solid was recrystallized with toluene, so that 0.8 g of a green powder of [Ir(mpptz-dmp)₃] (abbreviation), the phosphorescent organometallic iridium complex that is one embodiment of the present invention, was obtained in a yield of 45%. A synthesis scheme of Step 2 is shown in (b-2).

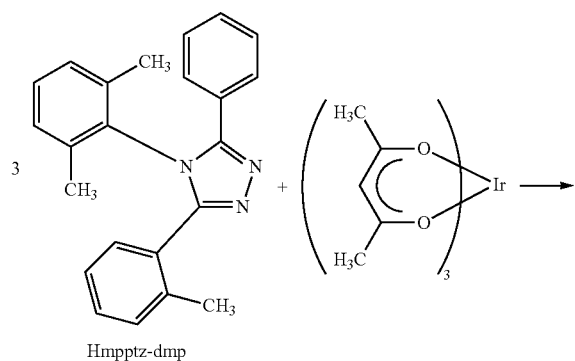

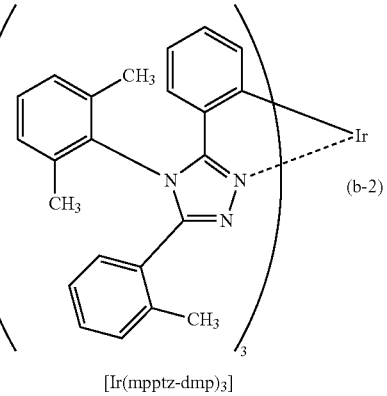

[Ir(mpptz-dmp)₃]

Figure 11:
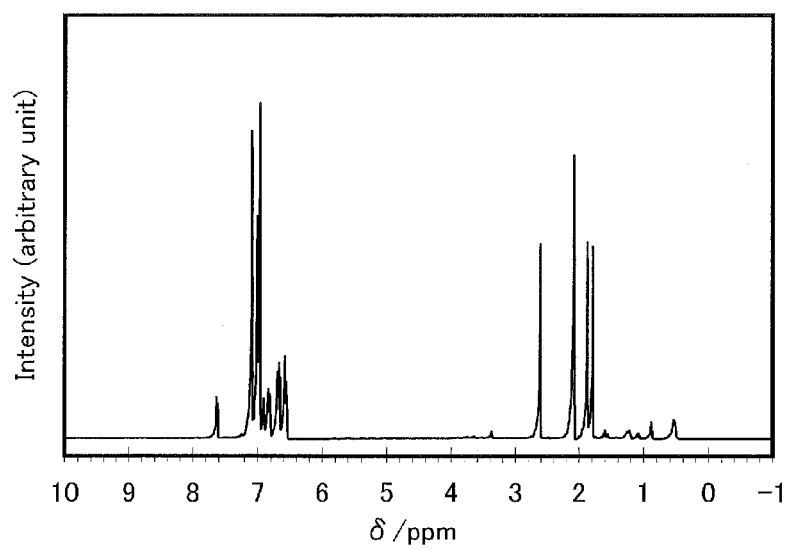
FIG. 11 shows a $^1$H-NMR chart of a phosphorescent organometallic iridium complex represented by Structural Formula (101).

An analysis result by nuclear magnetic resonance ($^1$H-NMR) spectroscopy of the green powder obtained in Step 2 is described below. FIG. 11 shows the $^1$H-NMR chart. These results revealed that [Ir(mpptz-dmp)₃] (abbreviation), the phosphorescent organometallic iridium complex which is one embodiment of the present invention represented by Structural Formula (101), was obtained in Synthesis Example 2.

1H-NMR. δ(toluene-d8): 1.82 (s, 3H), 1.90 (s, 3H), 2.64 (s, 3H), 6.56-6.62 (m, 3H), 6.67-6.75 (m, 3H), 6.82-6.88 (m, 1H), 6.91-6.97 (t, 1H), 7.00-7.12 (m, 2H), 7.63-7.67 (d, 1H).

Figure 12:
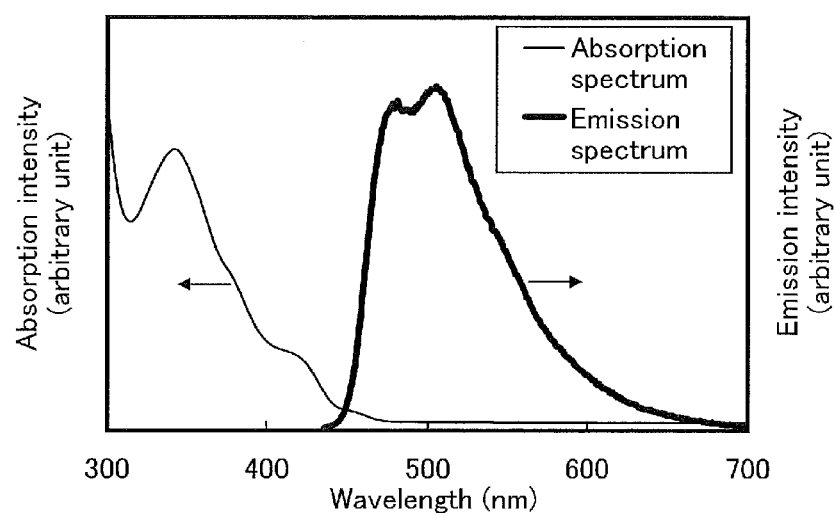
FIG. 12 shows an ultraviolet-visible absorption spectrum and an emission spectrum of a phosphorescent organometallic iridium complex represented by Structural Formula (101).

Next, [Ir(mpptz-dmp)₃] (abbreviation) was analyzed by ultraviolet-visible (UV) absorption spectroscopy. The UV spectrum was measured with an ultraviolet-visible spectrophotometer (V550 type manufactured by Japan Spectroscopy Corporation) using a toluene solution (0.845 mmol/L) at room temperature. Further, an emission spectrum of [Ir(mpptz-dmp)₃] (abbreviation) was measured. The emission spectrum was measured by a fluorescence spectrophotometer (FS920 manufactured by Hamamatsu Photonics K. K.) using a degassed toluene solution (0.845 mmol/L) at room temperature. FIG. 12 shows the measurement results. The horizontal axis represents wavelength and the vertical axes represent absorption intensity and emission intensity.

As shown in FIG. 12, [Ir(mpptz-dmp)₃] (abbreviation), the phosphorescent organometallic iridium complex that is one embodiment of the present invention, has emission peaks at 478 nm and 505 nm, and blue green light emission was observed from the toluene solution.

Further, tris{2-[5-(2-methylphenyl)-4-(2,6-dimethylphenyl)-4H-1,2,4-triazol-3-yl-κN2]phenyl-κC}iridium(III) (abbreviation: [Ir(mpptz-dmp)₃]) obtained in this example was analyzed by liquid chromatography mass spectrometry (LC/MS).

The LC/MS analysis was carried out with Acquity UPLC (produced by Waters Corporation) and Xevo G2 T of MS (produced by Waters Corporation).

In the MS analysis, ionization was carried out by an electrospray ionization (ESI) method. At this time, the capillary voltage and the sample cone voltage were set to 3.0 kV and 30 V, respectively, and detection was performed in a positive mode. A component with m/z of 1208 which underwent the ionization under the above-described conditions was collided with an argon gas in a collision cell to dissociate into product ions. Energy (collision energy) for the collision with argon was 50 eV. The mass range for the measurement was m/z=30 to 1300.

Figure 36:
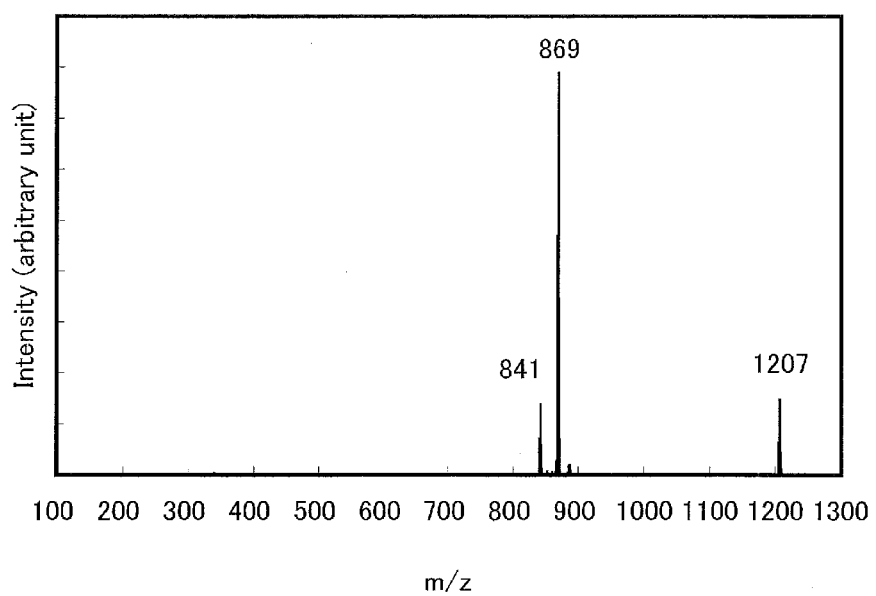
FIG. 36 shows LC/MS measurement results of a phosphorescent organometallic iridium complex represented by Structural Formula (101).

The detection result of the dissociated product ions by time-of-flight (TOF) MS are shown in FIG. 36.

The results in FIG. 36 show that product ions of [Ir(mpptz-dmp)₃] (abbreviation), the organometallic iridium complex that is one embodiment of the present invention represented by Structural Formula (101), were detected mainly around m/z 869 and m/z 841. Note that the results in FIG. 36 show characteristics derived from [Ir(mpptz-dmp)₃] (abbreviation) and therefore can be regarded as important data for identifying [Ir(mpptz-dmp)₃] (abbreviation) contained in the mixture.

EXAMPLE 3

Figure 13:
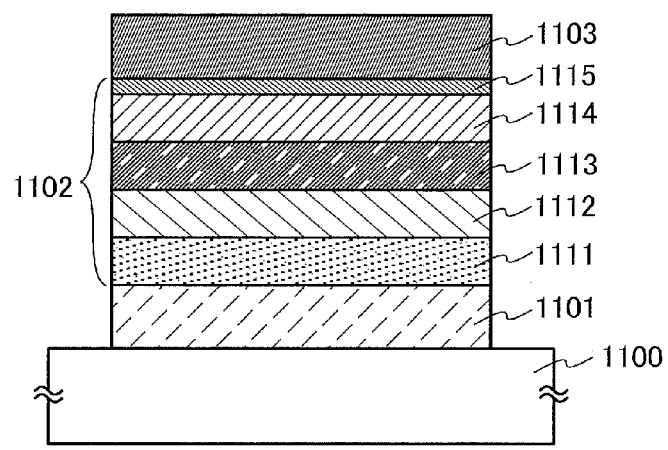
FIG. 13 illustrates a light-emitting element.

In this example, a light-emitting element 1 in which tris{2-[5-(2-methylphenyl)-4-phenyl-4H-1,2,4-triazol-3-yl-κN2]phenyl-κC}iridium(III) (abbreviation: [Ir(mpptz)₃]), the phosphorescent organometallic iridium complex represented by Structural Formula (100), is used for a light-emitting layer is described with reference to FIG. 13. Chemical formulae of materials used in this example are shown below.

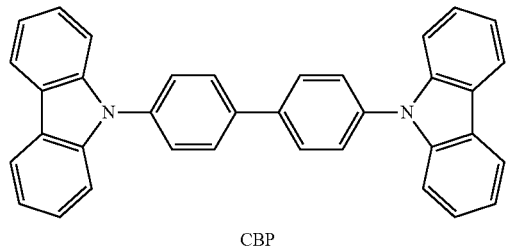
CBP

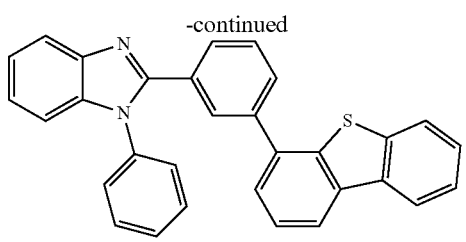
mDBTBIm-II

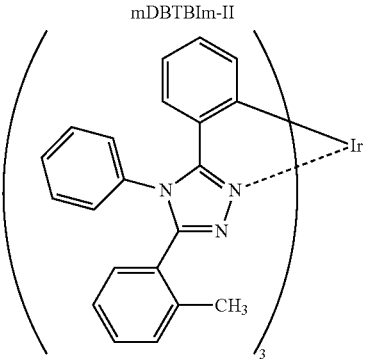
[Ir(mpptz)₃]

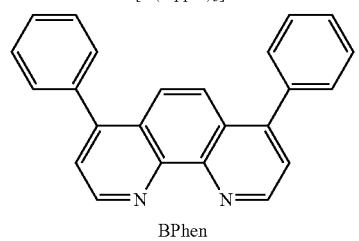
BPhen

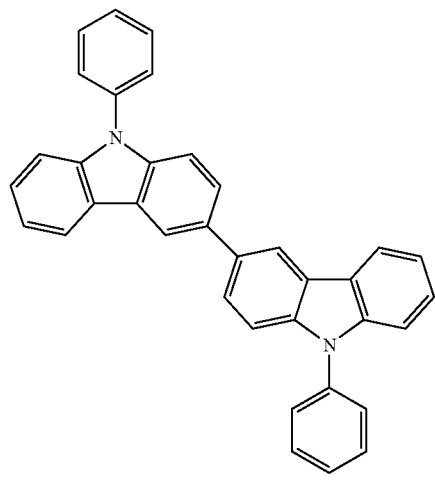
PCCP

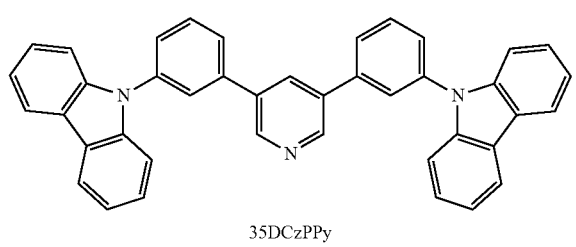
35DCzPPy

<<Fabrication of Light-emitting Element 1>>

First, indium tin oxide containing silicon oxide (ITSO) was deposited over a glass substrate 1100 by a sputtering method, so that a first electrode 1101 which functions as an anode was formed. The thickness was 110 nm and the electrode area was 2 mm×2 mm.

Then, as pretreatment for forming the light-emitting element over the substrate 1100, UV ozone treatment was performed for 370 seconds after washing of a surface of the substrate with water and baking that was performed at 200° C. for 1 hour.

After that, the substrate was transferred into a vacuum evaporation apparatus where the pressure had been reduced to approximately $10^{-4}$ Pa, and was subjected to vacuum baking at 170° C. for 30 minutes in a heating chamber of the vacuum evaporation apparatus, and then the substrate 1100 was cooled down for about 30 minutes.

Next, the substrate 1100 was fixed to a holder provided in the vacuum evaporation apparatus so that a surface of the substrate 1100 over which the first electrode 1101 was formed faced downward. In this example, a case will be described in which a hole-injection layer 1111, a hole-transport layer 1112, a light-emitting layer 1113, an electron-transport layer 1114, and an electron-injection layer 1115 which are included in an EL layer 1102 are sequentially formed by a vacuum evaporation method.

After reducing the pressure of the vacuum evaporation apparatus to $10^{-4}$ Pa, 4,4'-di(N-carbazolyl)biphenyl (abbreviation: CBP) and molybdenum(VI) oxide were co-evaporated with a mass ratio of CBP (abbreviation) to molybdenum oxide being 4:2, whereby the hole-injection layer 1111 was formed over the first electrode 1101. The thickness of the hole-injection layer 1111 was 60 nm Note that the co-evaporation is an evaporation method in which some different substances are evaporated from some different evaporation sources at the same time.

Next, 9-phenyl-9H-3-(9-phenyl-9H-carbazol-3-yl)carbazole (abbreviation: PCCP) was deposited by evaporation to a thickness of 20 nm, whereby the hole-transport layer 1112 was formed.

Next, the light-emitting layer 1113 was formed over the hole-transport layer 1112 in the following manner. First, 3,5-bis[3-(9H-carbazol-9-yl)phenyl]pyridine (abbreviation: 35DCzPPy), PCCP (abbreviation), and tris{2-[5-(2-methylphenyl)-4-phenyl-4H-1,2,4-triazol-3-yl-κN2]phenyl-κC}iridium(III) (abbreviation: [Ir(mpptz)$_3$]) were deposited by co-evaporation to a thickness of 30 nm with a mass ratio of 35DCzPPy (abbreviation) to PCCP (abbreviation) and [Ir(mpptz)$_3$] (abbreviation) being 0.3:1:0.06. After that, 35DCzPPy (abbreviation) and [Ir(mpptz)$_3$] (abbreviation) were deposited by co-evaporation to a thickness of 10 nm with a mass ratio of 35DCzPPy (abbreviation) to [Ir(mpptz)$_3$] (abbreviation) being 1:0.06. Thus, the light-emitting layer 1113 having a stacked layer structure was formed.

Then, over the light-emitting layer 1113, 2-[3-(dibenzothiophen-4-yl)phenyl]-1-phenyl-1H-benzimidazole (abbreviation: mDBTBIm-II) and [Ir(mpptz)$_3$] (abbreviation) were deposited by co-evaporation to a thickness of 10 nm with a mass ratio of mDBTBIm-II (abbreviation) and [Ir(mpptz)$_3$] (abbreviation) being 1:0.06, and bathophenanthroline (abbreviation: Bphen) was deposited by evaporation to a thickness of 15 nm, whereby the electron-transport layer 1114 having a staked-layer structure was formed. Furthermore, lithium fluoride was deposited by evaporation to a thickness of 1 nm over the electron-transport layer 1114, whereby the electron-injection layer 1115 was formed.

Finally, aluminum was deposited by evaporation to a thickness of 200 nm over the electron-injection layer 1115 to form a second electrode 1103 serving as a cathode; thus, the light-emitting element 1 was obtained. Note that in all the above evaporation steps, evaporation was performed by a resistance-heating method.

An element structure of the light-emitting element 1 obtained as described above is shown in Table 1.

Further, the fabricated light-emitting element 1 was sealed in a glove box containing a nitrogen atmosphere so as not to be exposed to the air (specifically, a sealant was applied onto an outer edge of the element and heat treatment was performed at 80° C. for 1 hour at the time of sealing).

<<Operation Characteristics of Light-emitting Element 1>>

Operation characteristics of the fabricated light-emitting element 1 were measured. Note that the measurement was carried out at room temperature (under an atmosphere in which the temperature was kept at 25° C.).

Figure 14:
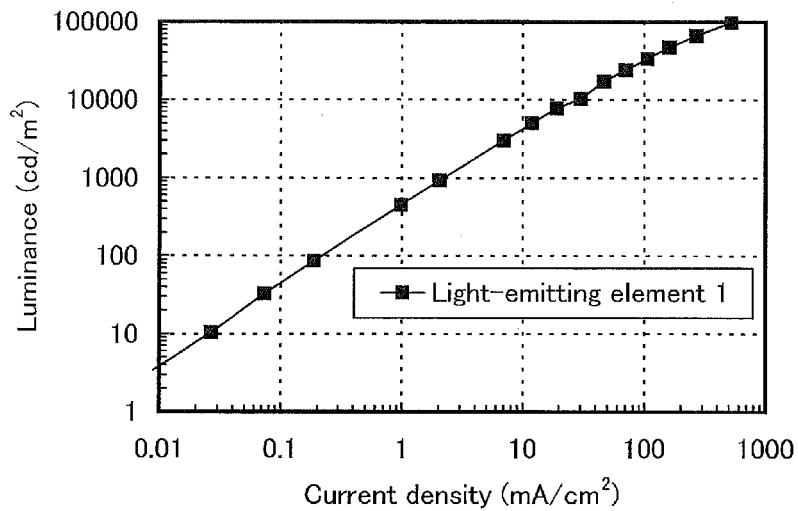
FIG. 14 shows current density-luminance characteristics of a light-emitting element 1.
Figure 15:
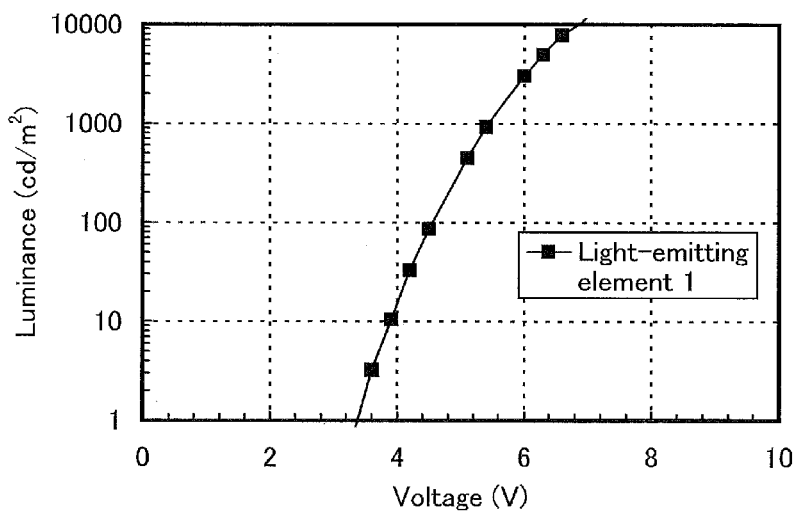
FIG. 15 shows voltage-luminance characteristics of a light-emitting element 1.
Figure 16:
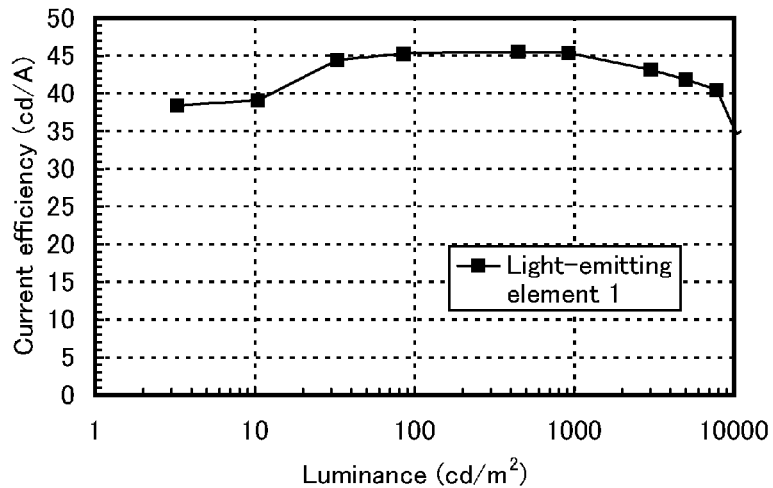
FIG. 16 shows luminance-current efficiency characteristics of a light-emitting element 1.
Figure 17:
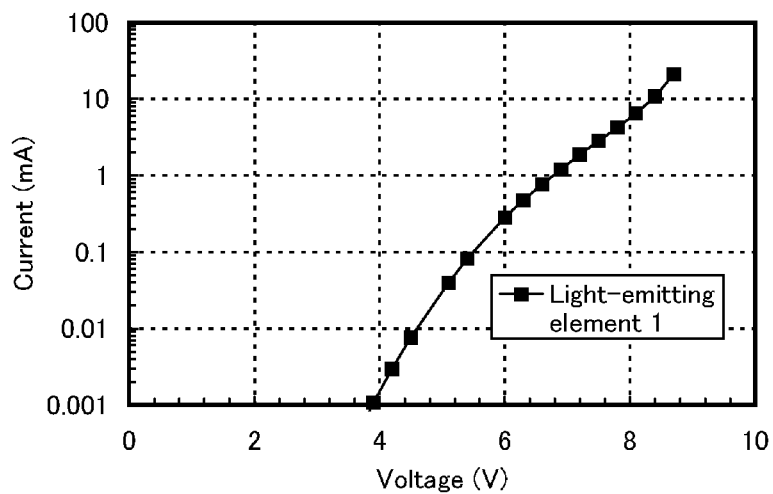
FIG. 17 shows voltage-current characteristics of a light-emitting element 1.
Figure 18:
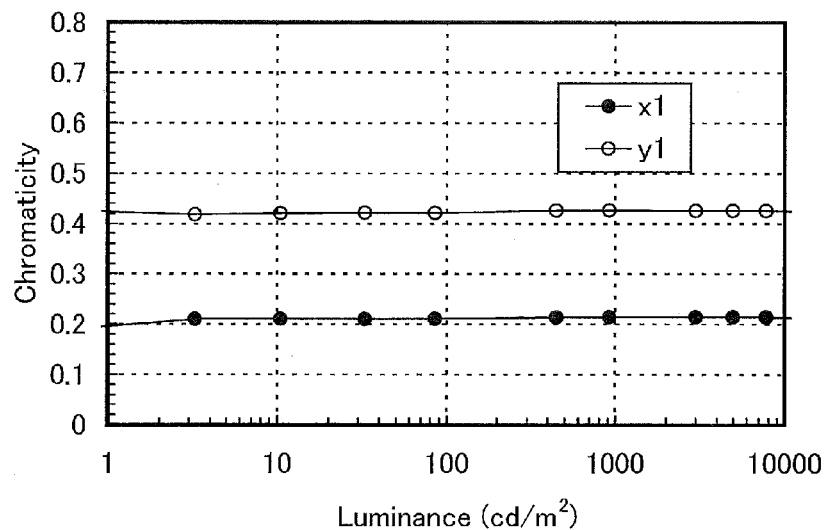
FIG. 18 shows luminance-chromaticity characteristics of a light-emitting element 1.

FIG. 14 shows current density-luminance characteristics of the light-emitting element 1. In FIG. 14, the vertical axis represents luminance (cd/m$^2$) and the horizontal axis represents current density (mA/cm$^2$). FIG. 15 shows voltage-luminance characteristics of the light-emitting element 1. In FIG. 15, the vertical axis represents luminance (cd/m$^2$) and the horizontal axis represents voltage (V). Further, FIG. 16 shows luminance-current efficiency characteristics of the light-emitting element 1. In FIG. 16, the vertical axis represents current efficiency (cd/A) and the horizontal axis represents luminance (cd/m$^2$). FIG. 17 shows voltage-current characteristics of the light-emitting element 1. In FIG. 17, the vertical axis represents current (mA) and the horizontal axis represents voltage (V). In addition, FIG. 18 shows luminance-chromaticity characteristics of the light-emitting element 1. In FIG. 18, the vertical axis represents chromaticity coordinate and the horizontal axis represents luminance (cd/m$^2$).

FIG. 16 reveals high efficiency of the light-emitting element 1 in which part of the light-emitting layer uses [Ir(mpptz)$_3$] (abbreviation), the phosphorescent organometallic iridium complex that is one embodiment of the present invention. Table 2 shows initial values of main characteristics of the light-emitting element 1 at a luminance of about 1000 cd/m$^2$.

TABLE 2

| | Voltage (V) | Current (mA) | Current Density (mA/cm$^2$) | Chromaticity (x, y) | Luminance (cd/m$^2$) | Current Efficiency (cd/A) | Power Efficiency (lm/W) | Quantum Efficiency (%) |
|---|---|---|---|---|---|---|---|---|
| Light-emitting Element 1 | 5.4 | 0.081 | 2.0 | (0.21, 0.43) | 920 | 45 | 26 | 19 |

The above results show that the light-emitting element 1 fabricated in this example is a high-luminance light-emitting element having high current efficiency. Moreover, it can be found that the light-emitting element exhibits green light emission.

Figure 19:
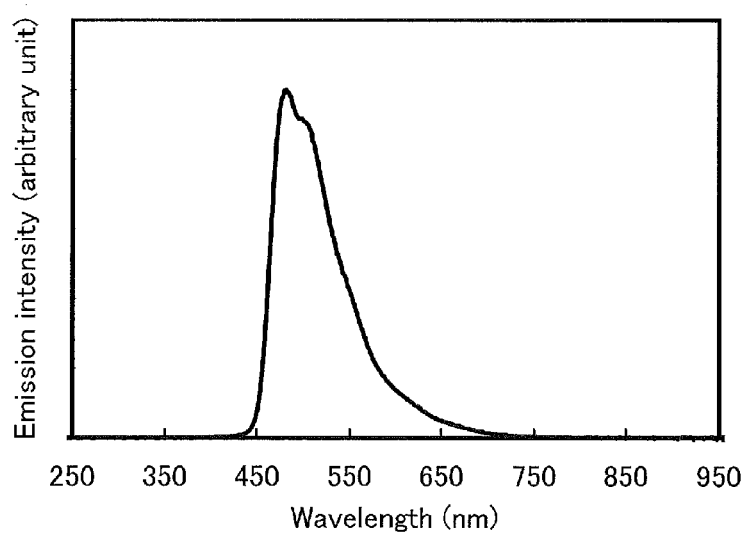
FIG. 19 shows an emission spectrum of a light-emitting element 1.

FIG. 19 shows an emission spectrum when a current at a current density of 0.1 mA/cm$^2$ was supplied to the light-emitting element 1. As shown in FIG. 19, the emission spectrum of the light-emitting element 1 has a peak at 486 nm and it is suggested that the peak is derived from emission of the phosphorescent organometallic iridium complex [Ir(mpptz)$_3$] (abbreviation).

TABLE 1

| | First Electrode | Hole-injection Layer | Hole-transport Layer | Light-emitting Layer | Electron-transport Layer | Electron-injection Layer | Second Electrode |
|---|---|---|---|---|---|---|---|
| Light-emitting Element 1 | ITSO (110 nm) | CBP:MoOx (4:2 60 nm) | PCCP (20 nm) | * | ** Bphen (15 nm) | LiF (1 nm) | Al (200 nm) |

* 35DCzPPy:PCCP:[Ir(mpptz)$_3$] (0.3:1:0.06 30 nm)\35DCzPPy:[Ir(mpptz)$_3$] (1:0.06 10 nm)
** mDBTBIm-II:[Ir(mpptz)$_3$](1:0.06 10 nm)

Figure 20:
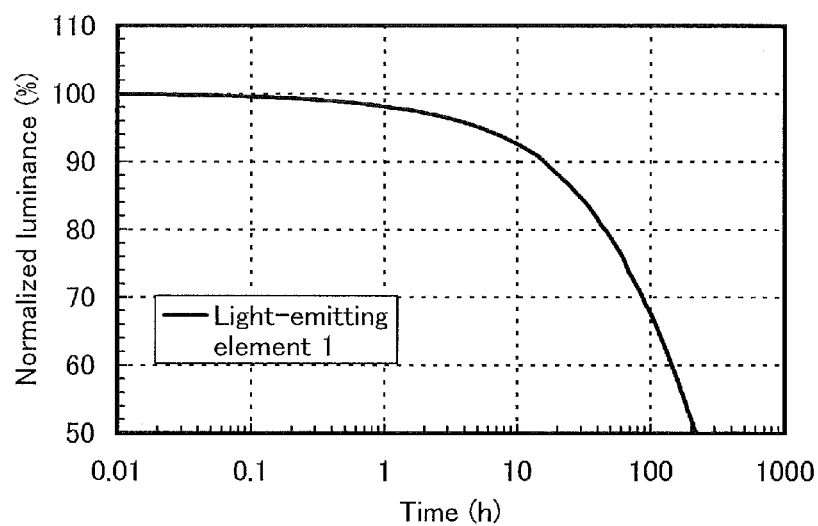
FIG. 20 shows reliability of a light-emitting element 1.

The light-emitting element 1 was subjected to a reliability test. Results of the reliability test are shown in FIG. 20. In FIG. 20, the vertical axis represents normalized luminance (%) with an initial luminance of 100% and the horizontal axis represents driving time (h) of the element. Note that in the reliability test, the light-emitting element 1 was driven under the conditions where the initial luminance was set to 1000 cd/m² and the current density was constant. The light-emitting element 1 kept about 66% of the initial luminance after 100 hours elapsed.

Thus, the reliability test revealed high reliability of the light-emitting element 1. In addition, it was confirmed that with the use of the phosphorescent organometallic iridium complex that is one embodiment of the present invention, a light-emitting element with a long lifetime can be obtained.

EXAMPLE 4

In this example, a light-emitting element 2 in which tris{2-[5-(2-methylphenyl)-4-(2,6-dimethylphenyl)-4H-1,2,4-triazol-3-yl-κN2]phenyl-κC}iridium(III) (abbreviation: [Ir(mpptz-dmp)$_3$]), the phosphorescent organometallic iridium complex represented by Structural Formula (101), is used for a light-emitting layer is described. Note that in the description of the light-emitting element 2 in this example, FIG. 13 which is used in the description of the light-emitting element 1 in Example 1 is to be referred to. Chemical formulae of materials used in this example are shown below.

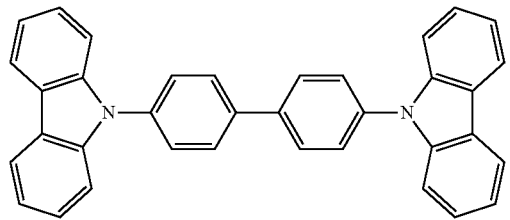

CBP

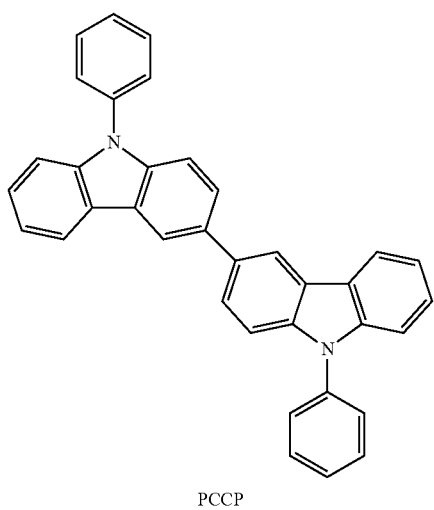

PCCP

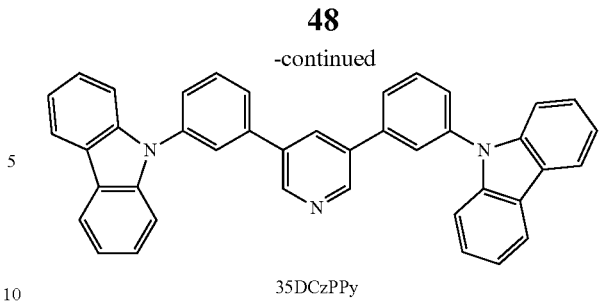

35DCzPPy

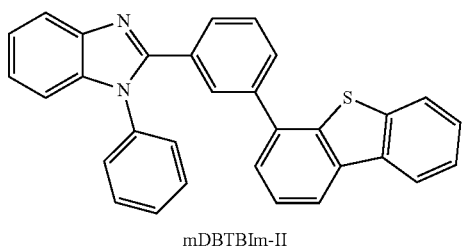

mDBTBIm-II

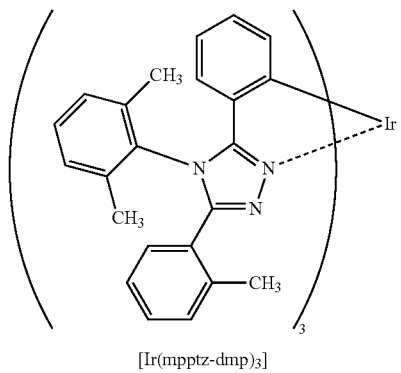

[Ir(mpptz-dmp)$_3$]

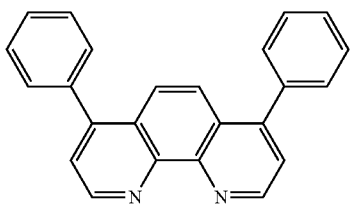

BPhen

<<Fabrication of Light-emitting Element 2>>

First, indium tin oxide containing silicon oxide (ITSO) was deposited over the glass substrate 1100 by a sputtering method, so that the first electrode 1101 which functions as an anode was formed. The thickness was 110 nm and the electrode area was 2 mm×2 mm.

Then, as pretreatment for forming the light-emitting element over the substrate 1100, UV ozone treatment was performed for 370 seconds after washing of a surface of the substrate with water and baking that was performed at 200° C. for 1 hour.

After that, the substrate was transferred into a vacuum evaporation apparatus where the pressure had been reduced to approximately $10^{-4}$ Pa, and was subjected to vacuum baking at 170° C. for 30 minutes in a heating chamber of the vacuum evaporation apparatus, and then the substrate 1100 was cooled down for about 30 minutes.

Next, the substrate 1100 was fixed to a holder provided in the vacuum evaporation apparatus so that a surface of the substrate 1100 over which the first electrode 1101 was formed faced downward. In this example, a case will be described in which the hole-injection layer 1111, the hole-transport layer 1112, the light-emitting layer 1113, the electron-transport layer 1114, and the electron-injection layer 1115 which are included in the EL layer 1102 are sequentially formed by a vacuum evaporation method.

After reducing the pressure of the vacuum evaporation apparatus to $10^{-4}$ Pa, 4,4'-di(N-carbazolyl)biphenyl (abbreviation: CBP) and molybdenum(VI) oxide were co-evaporated with a mass ratio of CBP (abbreviation) to molybdenum oxide being 4:2, whereby the hole-injection layer 1111 was formed over the first electrode 1101. The thickness of the hole-injection layer 1111 was 60 nm. Note that the co-evaporation is an evaporation method in which some different substances are evaporated from some different evaporation sources at the same time.

Next, 9-phenyl-9H-3-(9-phenyl-9H-carbazol-3-yl)carbazole (abbreviation: PCCP) was deposited by evaporation to a thickness of 20 nm, whereby the hole-transport layer 1112 was formed.

Next, the light-emitting layer 1113 was formed over the hole-transport layer 1112 in the following manner. First, 3,5-bis[3-(9H-carbazol-9-yl)phenyl]pyridine (abbreviation: 35DCzPPy), PCCP (abbreviation), and tris{2-[5-(2-methylphenyl)-4-(2,6-dimethylphenyl)-4H-1,2,4-triazol-3-yl-κN2]phenyl-κC}iridium(III) (abbreviation: [Ir(mpptz-dmp)$_3$]) were deposited by co-evaporation to a thickness of 30 nm with a mass ratio of 35DCzPPy (abbreviation) to PCCP (abbreviation) and [Ir(mpptz-dmp)$_3$] (abbreviation) being 0.3:1:0.06. After that, 35DCzPPy (abbreviation) and [Ir(mpptz-dmp)$_3$] (abbreviation) were deposited by co-evaporation to a thickness of 10 nm with a mass ratio of 35DCzPPy (abbreviation) to [Ir(mpptz-dmp)$_3$] (abbreviation) being 1:0.06. Thus, the light-emitting layer 1113 having a stacked layer structure was formed.

Then, over the light-emitting layer 1113, 2-[3-(dibenzothiophen-4-yl)phenyl]-1-phenyl-1H-benzimidazole (abbreviation: mDBTBIm-II) and [Ir(mpptz-dmp)$_3$] (abbreviation) were deposited by co-evaporation to a thickness of 10 nm with a mass ratio of mDBTBIm-II (abbreviation) and [Ir(mpptz-dmp)$_3$] (abbreviation) being 1:0.06, and bathophenanthroline (abbreviation: Bphen) was deposited by evaporation to a thickness of 15 nm, whereby the electron-transport layer 1114 having a staked-layer structure was formed. Furthermore, lithium fluoride was deposited by evaporation to a thickness of 1 nm over the electron-transport layer 1114, whereby the electron-injection layer 1115 was formed.

Finally, aluminum was deposited by evaporation to a thickness of 200 nm over the electron-injection layer 1115 to form the second electrode 1103 serving as a cathode; thus, the light-emitting element 2 was obtained. Note that in all the above evaporation steps, evaporation was performed by a resistance-heating method.

An element structure of the light-emitting element 2 obtained as described above is shown in Table 3.

TABLE 3

| | First Electrode | Hole-injection Layer | Hole-transport Layer | Light-emitting Layer | Electron-transport Layer | Electron-injection Layer | Second Electrode |
|---|---|---|---|---|---|---|---|
| Light-emitting Element 2 | ITSO (110 nm) | CBP:MoO$x$ (4:2 60 nm) | PCCP (20 nm) | * | ** Bphen (15 nm) | LiF (1 nm) | Al (200 nm) |

* 35DCzPPy:PCCP:[Ir(mpptz-dmp)$_3$] (0.3:1:0.06 30 nm)\35DCzPPy:[Ir(mpptz-dmp)$_3$] (1:0.06 10 nm)
** mDBTBIm-II:[Ir(mpptz-dmp)$_3$](1:0.06 10 nm)

Further, the fabricated light-emitting element 2 was sealed in a glove box containing a nitrogen atmosphere so as not to be exposed to the air (specifically, a sealant was applied onto an outer edge of the element and heat treatment was performed at 80° C. for 1 hour at the time of sealing).

<<Operation Characteristics of Light-emitting Element 2>>

Operation characteristics of the fabricated light-emitting element 2 were measured. Note that the measurement was carried out at room temperature (under an atmosphere in which the temperature was kept at 25° C.).

Figure 21:
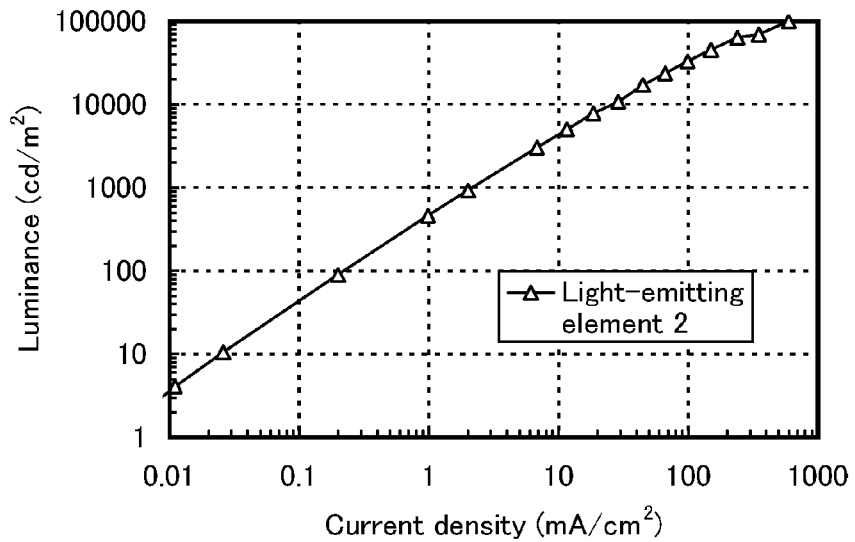
FIG. 21 shows current density-luminance characteristics of a light-emitting element 2.
Figure 22:
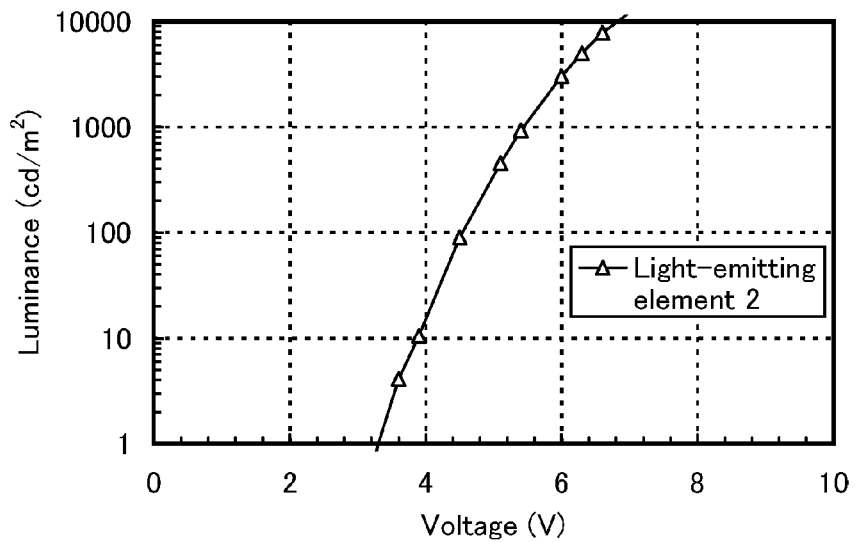
FIG. 22 shows voltage-luminance characteristics of a light-emitting element 2.
Figure 23:
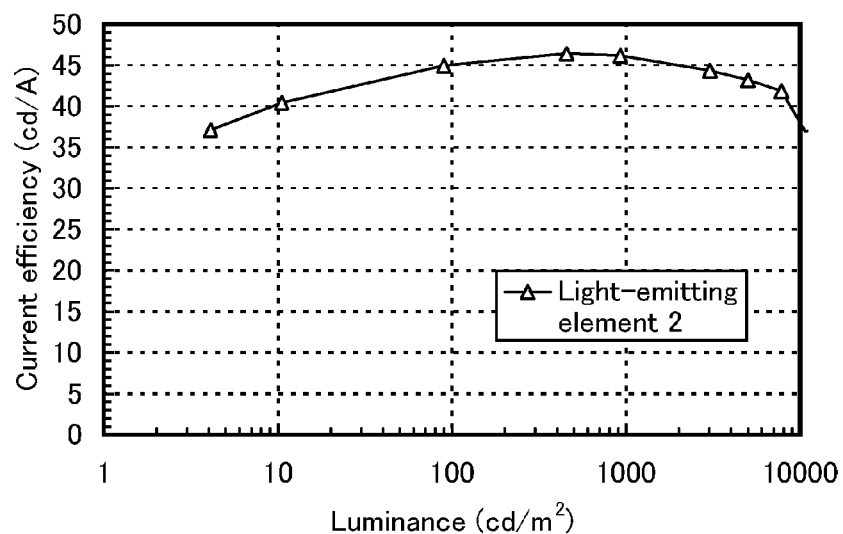
FIG. 23 shows luminance-current efficiency characteristics of a light-emitting element 2.
Figure 24:
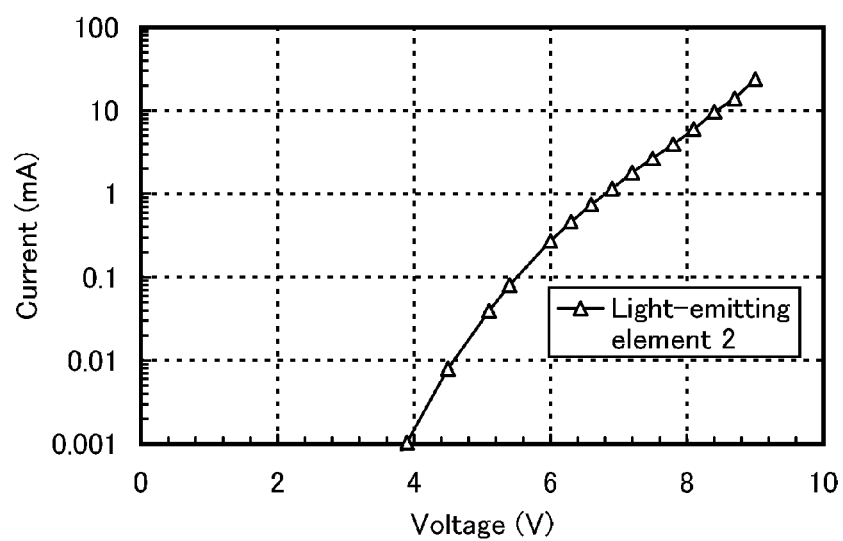
FIG. 24 shows voltage-current characteristics of a light-emitting element 2.
Figure 25:
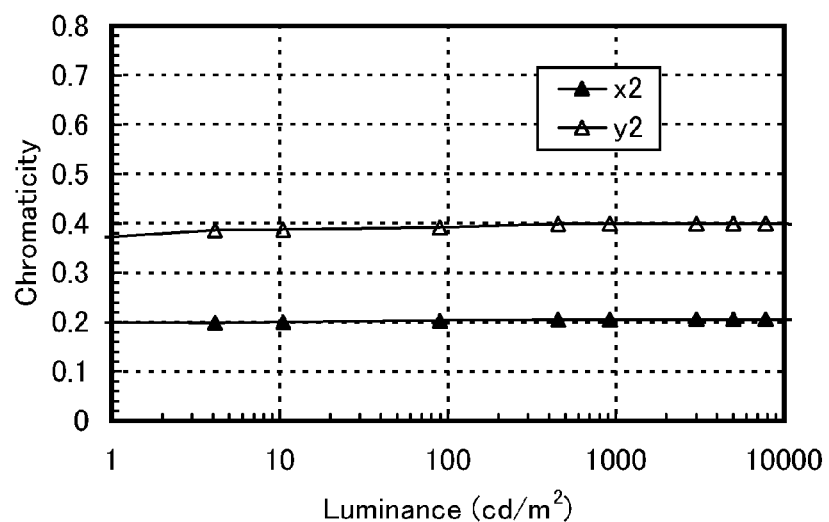
FIG. 25 shows luminance-chromaticity characteristics of a light-emitting element 2.

FIG. 21 shows current density-luminance characteristics of the light-emitting element 2. In FIG. 21, the vertical axis represents luminance (cd/m$^2$) and the horizontal axis represents current density (mA/cm$^2$). FIG. 22 shows voltage-luminance characteristics of the light-emitting element 2. In FIG. 22, the vertical axis represents luminance (cd/m$^2$) and the horizontal axis represents voltage (V). Further, FIG. 23 shows luminance-current efficiency characteristics of the light-emitting element 2. In FIG. 23, the vertical axis represents current efficiency (cd/A) and the horizontal axis represents luminance (cd/m$^2$). FIG. 24 shows voltage-current characteristics of the light-emitting element 2. In FIG. 24, the vertical axis represents current (mA) and the horizontal axis represents voltage (V). In addition, FIG. 25 shows luminance-chromaticity characteristics of the light-emitting element 2. In FIG. 25, the vertical axis represents chromaticity coordinate and the horizontal axis represents luminance (cd/m$^2$).

FIG. 23 reveals high efficiency of the light-emitting element 2 in which part of the light-emitting layer uses [Ir(mpptz-dmp)$_3$] (abbreviation), the phosphorescent organometallic iridium complex that is one embodiment of the present invention. Table 4 shows initial values of main characteristics of the light-emitting element 2 at a luminance of about 1000 cd/m$^2$.

TABLE 4

| | Voltage (V) | Current (mA) | Current Density (mA/cm$^2$) | Chromaticity (x, y) | Luminance (cd/m$^2$) | Current Efficiency (cd/A) | Power Efficiency (lm/W) | Quantum Efficiency (%) |
|---|---|---|---|---|---|---|---|---|
| Light-emitting Element 2 | 5.4 | 0.08 | 2.0 | (0.21, 0.40) | 920 | 46 | 27 | 20 |

The above results show that the light-emitting element 2 fabricated in this example is a high-luminance light-emitting element having high current efficiency. Moreover, as for color purity, it can be found that the light-emitting element exhibits blue green light emission with excellent color purity.

Figure 26:
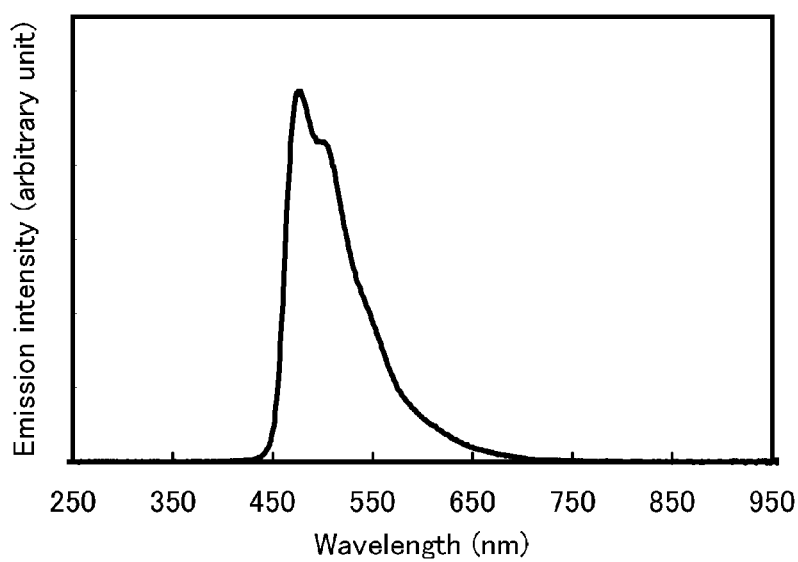
FIG. 26 shows an emission spectrum of a light-emitting element 2.

FIG. 26 shows an emission spectrum when a current at a current density of 0.1 mA/cm$^2$ was supplied to the light-emitting element 2. As shown in FIG. 26, the emission spectrum of the light-emitting element 2 has a peak at 479 nm and it is suggested that the peak is derived from emission of the phosphorescent organometallic iridium complex [Ir(mpptz-dmp)$_3$] (abbreviation).

Figure 27:
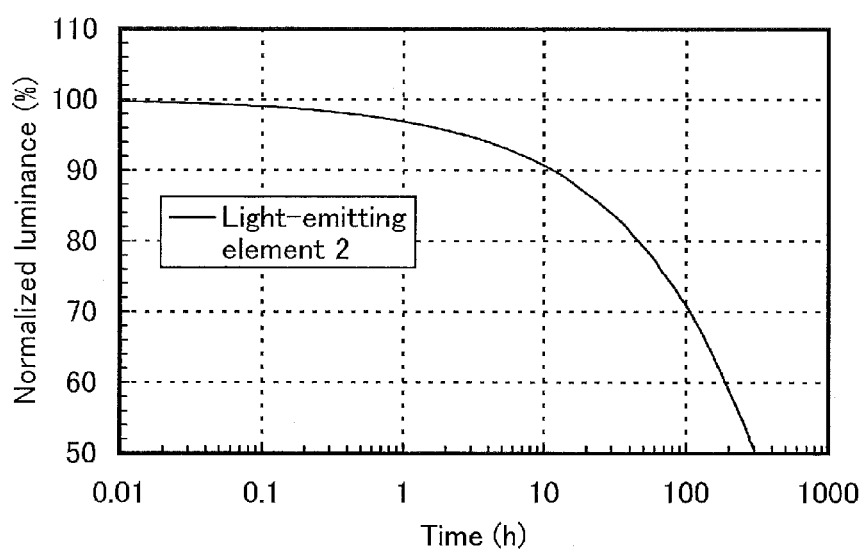
FIG. 27 shows reliability of a light-emitting element 2.

The light-emitting element 2 was subjected to a reliability test. Results of the reliability test are shown in FIG. 27. In FIG. 27, the vertical axis represents normalized luminance (%) with an initial luminance of 100% and the horizontal axis represents driving time (h) of the element. Note that in the reliability test, the light-emitting element 2 was driven under the conditions where the initial luminance was set to 1000 cd/m$^2$ and the current density was constant. The light-emitting element 2 kept about 70% of the initial luminance after 100 hours elapsed.

Thus, the reliability test revealed high reliability of the light-emitting element 2. In addition, it was confirmed that with the use of the phosphorescent organometallic iridium complex that is one embodiment of the present invention, a light-emitting element with a long lifetime can be obtained.

EXAMPLE 5

In this example, a light-emitting element 3 in which [Ir(mpptz-dmp)$_3$] (abbreviation), the phosphorescent organometallic iridium complex represented by Structural Formula (101), is used for a light-emitting layer is described. Note that in the description of the light-emitting element 3 in this example, FIG. 13 which is used in the description of the light-emitting element 1 in Example 1 is to be referred to. Chemical formulae of materials used in this example are shown below.

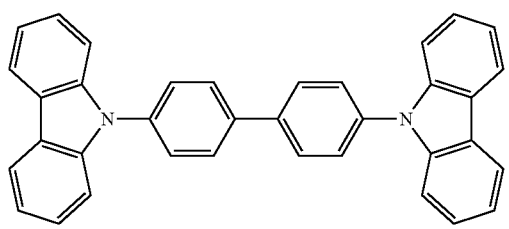

CBP

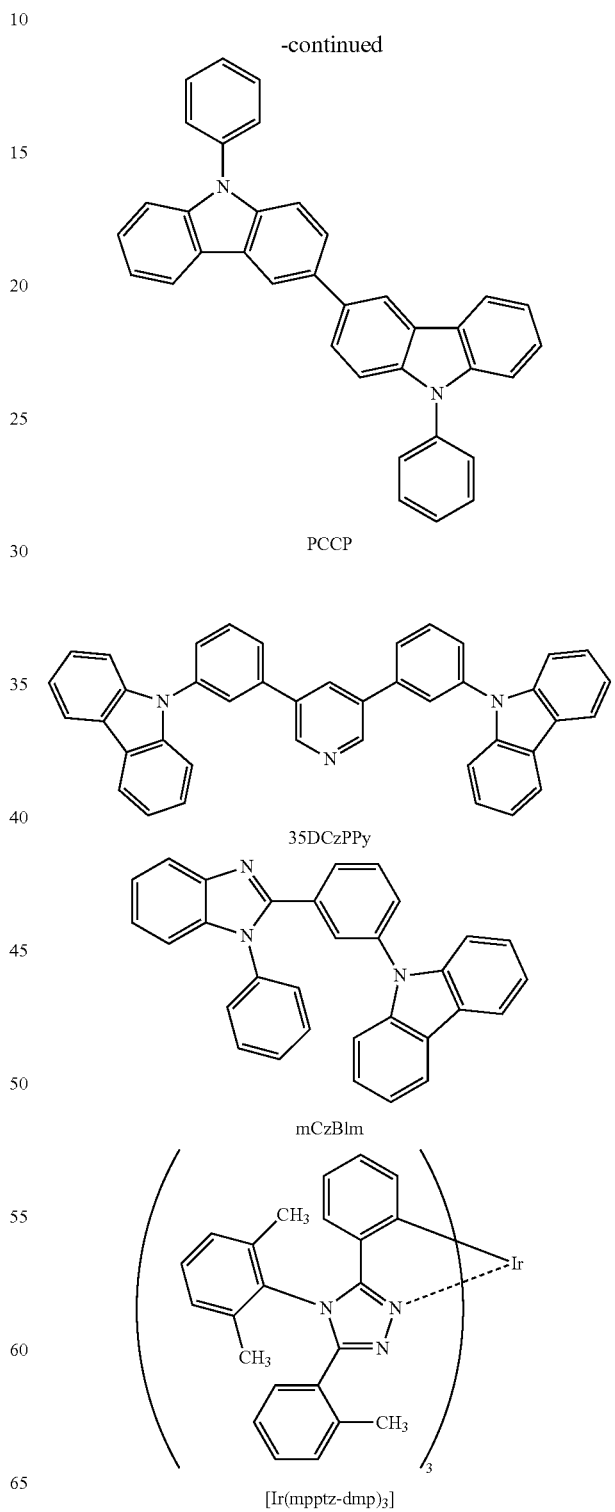

PCCP

35DCzPPy mCzBIm

[Ir(mpptz-dmp)$_3$]

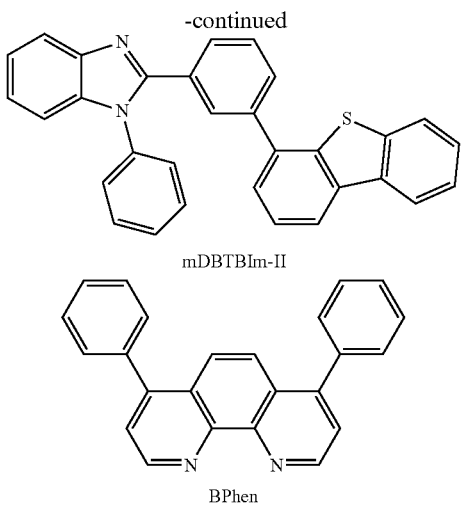

mDBTBIm-II

BPhen

<<Fabrication of Light-emitting Element 3>>

First, indium tin oxide containing silicon oxide (ITSO) was deposited over the glass substrate 1100 by a sputtering method, so that the first electrode 1101 which functions as an anode was formed. The thickness was 110 nm and the electrode area was 2 mm×2 mm.

Then, as pretreatment for forming the light-emitting element over the substrate 1100, UV ozone treatment was performed for 370 seconds after washing of a surface of the substrate with water and baking that was performed at 200° C. for 1 hour.

After that, the substrate was transferred into a vacuum evaporation apparatus where the pressure had been reduced to approximately $10^{-4}$ Pa, and was subjected to vacuum baking at 170° C. for 30 minutes in a heating chamber of the vacuum evaporation apparatus, and then the substrate 1100 was cooled down for about 30 minutes.

Next, the substrate 1100 was fixed to a holder provided in the vacuum evaporation apparatus so that a surface of the substrate 1100 over which the first electrode 1101 was formed faced downward. In this example, a case will be described in which the hole-injection layer 1111, the hole-transport layer 1112, the light-emitting layer 1113, the electron-transport layer 1114, and the electron-injection layer 1115 which are included in the EL layer 1102 are sequentially formed by a vacuum evaporation method.

After reducing the pressure of the vacuum evaporation apparatus to $10^{-4}$ Pa, 4,4'-di(N-carbazolyl)biphenyl (abbreviation: CBP) and molybdenum(VI) oxide were co-evaporated with a mass ratio of CBP (abbreviation) to molybdenum oxide being 4:2, whereby the hole-injection layer 1111 was formed over the first electrode 1101. The thickness of the hole-injection layer 1111 was 60 nm Note that the co-evaporation is an evaporation method in which some different substances are evaporated from some different evaporation sources at the same time.

Next, 9-phenyl-9H-3-(9-phenyl-9H-carbazol-3-yl)carbazole (abbreviation: PCCP) was deposited by evaporation to a thickness of 20 nm, whereby the hole-transport layer 1112 was formed.

Next, the light-emitting layer 1113 was formed over the hole-transport layer 1112 in the following manner. First, 2-[3-(9H-carbazol-9-yl)phenyl]-1-phenylbenzimidazole (abbreviation: mCzBIm), PCCP (abbreviation), and tris{2-[5-(2-methylphenyl)-4-(2,6-dimethylphenyl)-4H-1,2,4-triazol-3-yl-κN2]phenyl-κC}iridium(III) (abbreviation: [Ir(mpptz-dmp)₃]) were deposited by co-evaporation to a thickness of 30 nm with a mass ratio of mCzBIm (abbreviation) to PCCP (abbreviation) and [Ir(mpptz-dmp)₃] (abbreviation) being 0.25:1:0.06. After that, mCzBIm (abbreviation), PCCP (abbreviation), and [Ir(mpptz-dmp)₃] (abbreviation) were deposited by co-evaporation to a thickness of 10 nm with a mass ratio of mCzBIm (abbreviation) to PCCP (abbreviation) and [Ir(mpptz-dmp)₃] (abbreviation) being 1:0.15:0.06. Thus, the light-emitting layer 1113 having a stacked layer structure was formed.

Then, over the light-emitting layer 1113, 2-[3-(dibenzothiophen-4-yl)phenyl]-1-phenyl-1H-benzimidazole (abbreviation: mDBTBIm-II) and [Ir(mpptz-dmp)₃] (abbreviation) were deposited by co-evaporation to a thickness of 10 nm with a mass ratio of mDBTBIm-II (abbreviation) and [Ir(mpptz-dmp)₃] (abbreviation) being 1:0.06, and bathophenanthroline (abbreviation: Bphen) was deposited by evaporation to a thickness of 15 nm, whereby the electron-transport layer 1114 having a staked-layer structure was formed. Furthermore, lithium fluoride was deposited by evaporation to a thickness of 1 nm over the electron-transport layer 1114, whereby the electron-injection layer 1115 was formed.

Finally, aluminum was deposited by evaporation to a thickness of 200 nm over the electron-injection layer 1115 to form the second electrode 1103 serving as a cathode; thus, the light-emitting element 3 was obtained. Note that in all the above evaporation steps, evaporation was performed by a resistance-heating method.

An element structure of the light-emitting element 3 obtained as described above is shown in Table 5.

TABLE 5

| | First Electrode | Hole-injection Layer | Hole-transport Layer | Light-emitting Layer | Electron-transport Layer | Electron-injection Layer | Second Electrode |
|---|---|---|---|---|---|---|---|
| Light-emitting Element 3 | ITSO (110 nm) | CBP:MoOx (4:2 60 nm) | PCCP (20 nm) | * | ** Bphen (15 nm) | LiF (1 nm) | Al (200 nm) |

* mCzBIm:PCCP:[Ir(mpptz-dmp)₃] (0.25:1:0.06 30 nm)\mCzBIm:PCCP:[Ir(mpptz-dmp)₃] (1:0.15:0.06 10 nm)
** mDBTBImII:[Ir(mpptz-dmp)₃](1:0.06 10 nm)

Further, the fabricated light-emitting element 3 was sealed in a glove box containing a nitrogen atmosphere so as not to be exposed to the air (specifically, a sealant was applied onto an outer edge of the element and heat treatment was performed at 80° C. for 1 hour at the time of sealing).

<<Operation Characteristics of Light-emitting Element 3>>

Operation characteristics of the fabricated light-emitting element 3 were measured. Note that the measurement was carried out at room temperature (under an atmosphere in which the temperature was kept at 25° C.).

Figure 28:
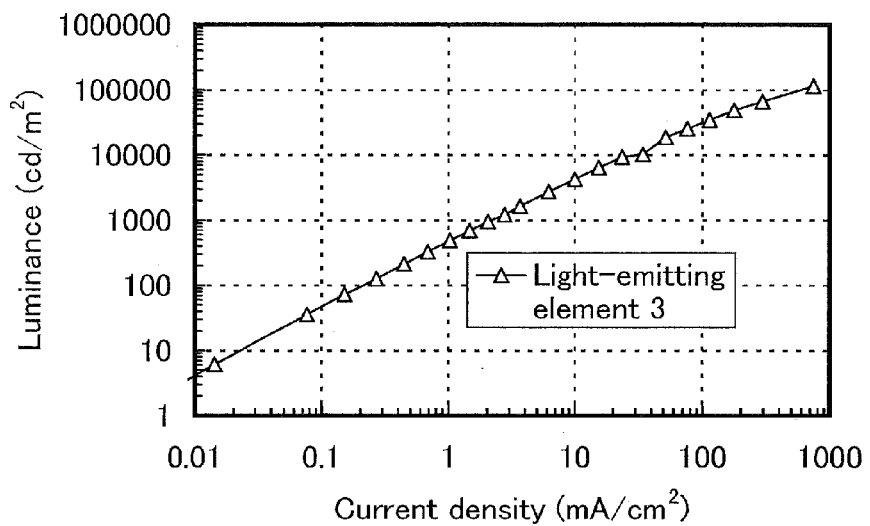
FIG. 28 shows current density-luminance characteristics of a light-emitting element 3.
Figure 29:
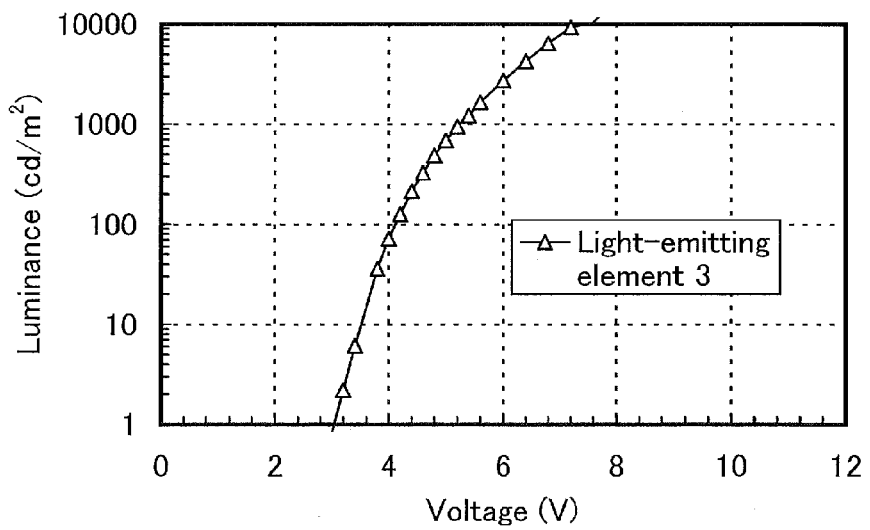
FIG. 29 shows voltage-luminance characteristics of a light-emitting element 3.
Figure 30:
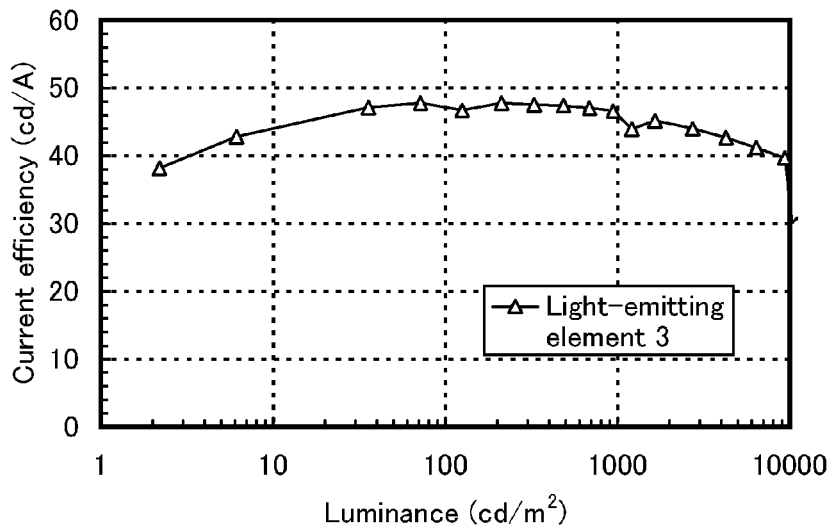
FIG. 30 shows luminance-current efficiency characteristics of a light-emitting element 3.
Figure 31:
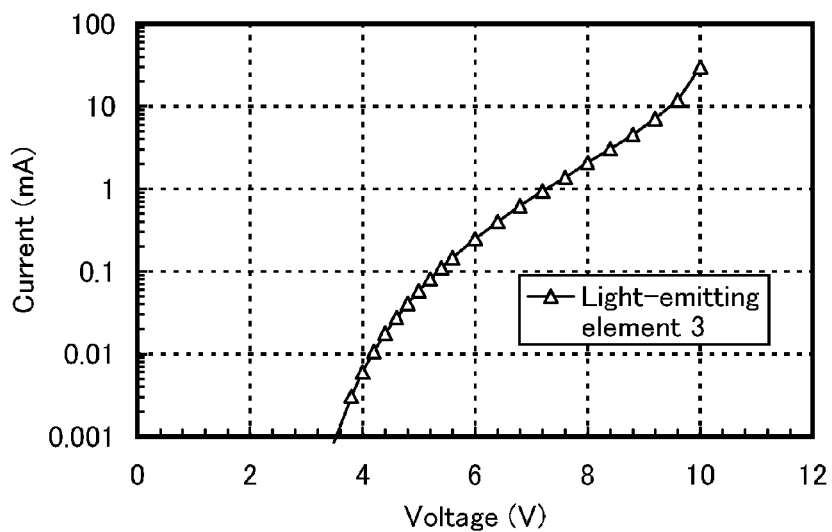
FIG. 31 shows voltage-current characteristics of a light-emitting element 3.
Figure 32:
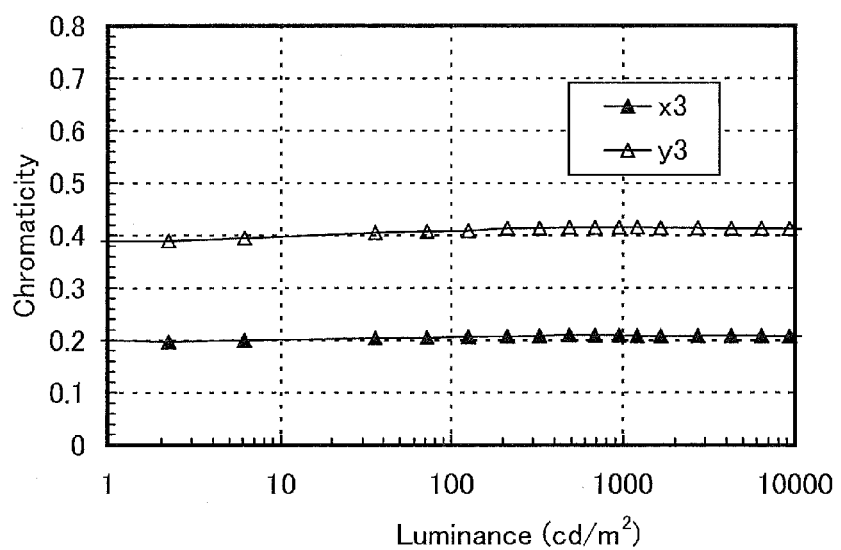
FIG. 32 shows luminance-chromaticity characteristics of a light-emitting element 3.

FIG. 28 shows current density-luminance characteristics of the light-emitting element 3. In FIG. 28, the vertical axis represents luminance (cd/m$^2$) and the horizontal axis represents current density (mA/cm$^2$). FIG. 29 shows voltage-luminance characteristics of the light-emitting element 3. In FIG. 29, the vertical axis represents luminance (cd/m$^2$) and the horizontal axis represents voltage (V). Further, FIG. 30 shows luminance-current efficiency characteristics of the light-emitting element 3. In FIG. 30, the vertical axis represents current efficiency (cd/A) and the horizontal axis represents luminance (cd/m$^2$). FIG. 31 shows voltage-current characteristics of the light-emitting element 3. In FIG. 31, the vertical axis represents current (mA) and the horizontal axis represents voltage (V). In addition, FIG. 32 shows luminance-chromaticity characteristics of the light-emitting element 3. In FIG. 32, the vertical axis represents chromaticity coordinate and the horizontal axis represents luminance (cd/m$^2$).

FIG. 30 reveals high efficiency of the light-emitting element 3 in which part of the light-emitting layer uses [Ir(mpptz-dmp)$_3$] (abbreviation), the phosphorescent organometallic iridium complex that is one embodiment of the present invention. Table 6 shows initial values of main characteristics of the light-emitting element 3 at a luminance of about 1000 cd/m$^2$.

4-(2,6-diisopropylphenyl)-4H-1,2,4-triazol-3-yl-κN2]phenyl-κC}iridium(III) (abbreviation: [Ir(mpptz-diPrp)$_3$]), which is one embodiment of the present invention represented by Structural Formula (105) in Embodiment 1, is described. A structure of [Ir(mpptz-diPrp)$_3$] (abbreviation) is shown below.

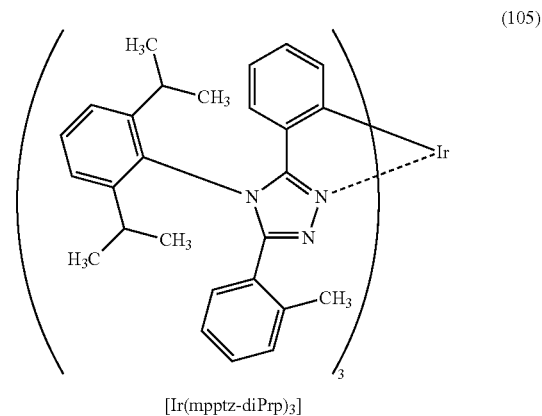

[Ir(mpptz-diPrp)$_3$]

TABLE 6

| | Voltage (V) | Current (mA) | Current Density (mA/cm$^2$) | Chromaticity (x, y) | Luminance (cd/m$^2$) | Current Efficiency (cd/A) | Power Efficiency (lm/W) | Quantum Efficiency (%) |
|---|---|---|---|---|---|---|---|---|
| Light-emitting Element 3 | 5.2 | 0.08 | 2.0 | (0.21, 0.42) | 940 | 47 | 28 | 20 |

The above results show that the light-emitting element 3 fabricated in this example is a high-luminance light-emitting element having high current efficiency. Moreover, it can be found that the light-emitting element exhibits blue green light emission.

Figure 33:
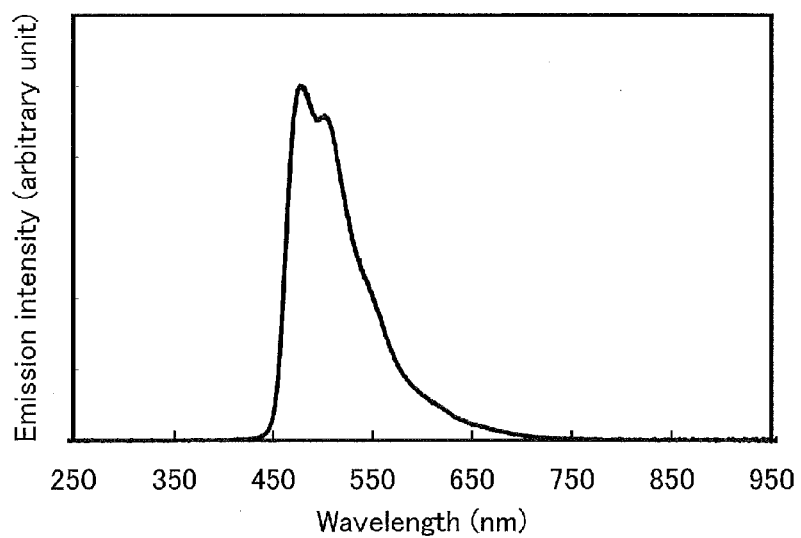
FIG. 33 shows an emission spectrum of a light-emitting element 3.

FIG. 33 shows an emission spectrum when a current at a current density of 0.1 mA/cm$^2$ was supplied to the light-emitting element 3. As shown in FIG. 33, the emission spectrum of the light-emitting element 3 has a peak at 482 nm and it is suggested that the peak is derived from emission of the phosphorescent organometallic iridium complex [Ir(mpptz-dmp)$_3$] (abbreviation).

Figure 34:
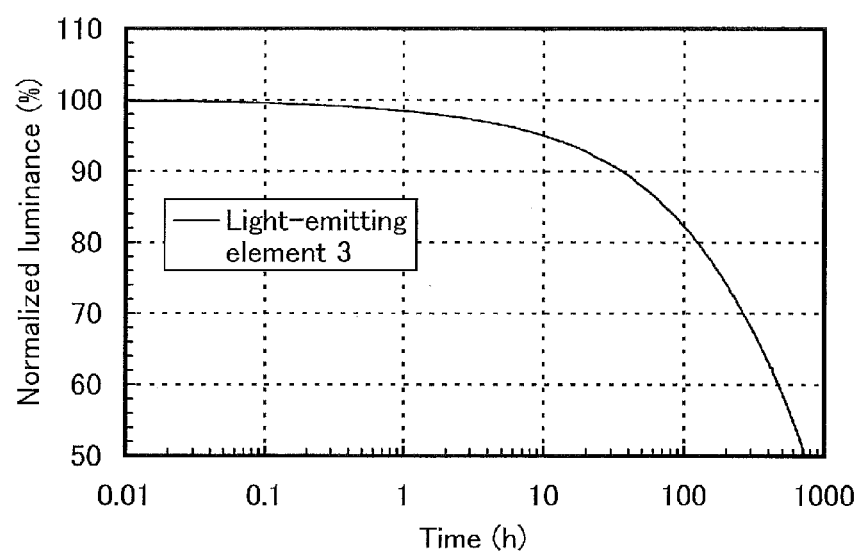
FIG. 34 shows reliability of a light-emitting element 3.

The light-emitting element 3 was subjected to a reliability test. Results of the reliability test are shown in FIG. 34. In FIG. 34, the vertical axis represents normalized luminance (%) with an initial luminance of 100% and the horizontal axis represents driving time (h) of the element. Note that in the reliability test, the light-emitting element 3 was driven under the conditions where the initial luminance was set to 1000 cd/m$^2$ and the current density was constant. The light-emitting element 3 kept about 80% of the initial luminance after 100 hours elapsed.

Thus, the reliability test revealed high reliability of the light-emitting element 3. In addition, it was confirmed that with the use of the phosphorescent organometallic iridium complex that is one embodiment of the present invention, a light-emitting element with a long lifetime can be obtained.

EXAMPLE 6

SYNTHESIS EXAMPLE 3

In this example, a synthesis method of a phosphorescent organometallic iridium complex tris{2-[5-(2-methylphenyl)-

Step 1: Synthesis of 3-Phenyl-4-(2,6-diisopropylphenyl)-5-(2-methylphenyl)-1,2,4-4H-triazole (abbreviation: Hmpptz-diPrp Into a 300-mL three-neck flask were put 12.6 g (43.3 mmol) of [chloro(2-methylphenyl)methanone][chloro(phenyl)methylidene]hydrazone, 25.0 g (141 mmol) of 2,6-diisopropylaniline, and 100 mL of N,N-dimethylaniline, and the mixture was heated and stirred at 160° C. for 20 hours. After reaction for the predetermined time, the reacted solution was slowly added to 500 mL of 1M hydrochloric acid, and the mixture was stiffed for 30 minutes. Dichloromethane was added to this solution and an objective substance was extracted. The obtained organic layer was washed with water and an aqueous solution of sodium hydrogen carbonate, and was dried with magnesium sulfate. The magnesium sulfate was removed by gravity filtration, and the solvent in the obtained organic layer was distilled off to give a brown liquid. This liquid was purified by silica gel column chromatography. A mixed solvent of ethyl acetate and hexane in a ratio of 1:2 was used as a developing solvent. The obtained fraction was concentrated to give 5.2 g of a brown solid of Hmpptz-diPrp (abbreviation), an objective 4H-triazole derivative, in a yield of 52%. A synthesis scheme of Step 1 is shown in (c-1).

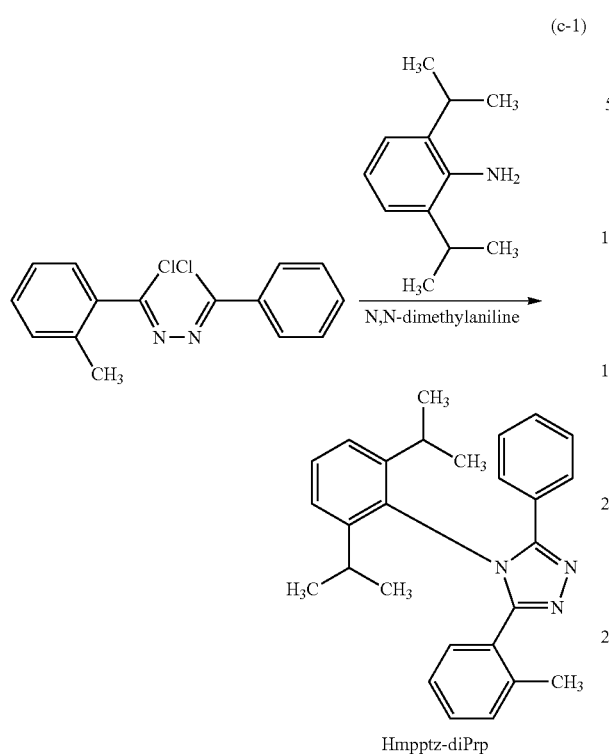

(c-1)

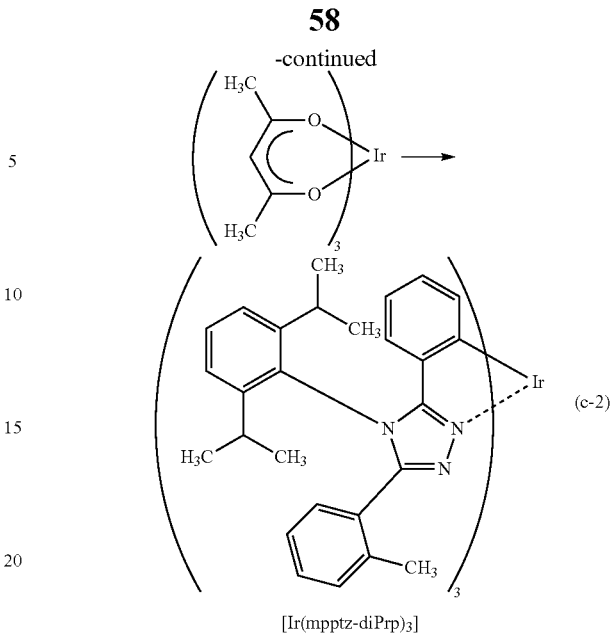

[Ir(mpptz-diPrp)₃]

Step 2: Synthesis of Tris{2-[5-(2-methylphenyl)-4-(2,6-diisopropylphenyl)-4H-1,2,4-triazol-3-yl-κN2]phenyl-κC}iridium(III) (abbreviation: [Ir(mpptz-diPrp)₃]

Then, 4.0 g (10.0 mmol) of Hmpptz-diPrp (abbreviation), which was the ligand obtained in Step 1, and 1.0 g (2.0 mmol) of tris(acetylacetonato)iridium(III) were put into a container for high-temperature heating, and degasification was carried out. The mixture in the reaction container was heated and stirred at 250° C. for 48 hours under Ar flow. After reaction for the predetermined time, the obtained solid was washed with dichloromethane to give a yellow solid. This solid was recrystallized with toluene, so that 1.4 g of a yellow powder of [Ir(mpptz-diPrp)₃] (abbreviation), the phosphorescent organometallic iridium complex which is one embodiment of the present invention, was obtained in a yield of 51%. A synthesis scheme of Step 2 is shown in (c-2).

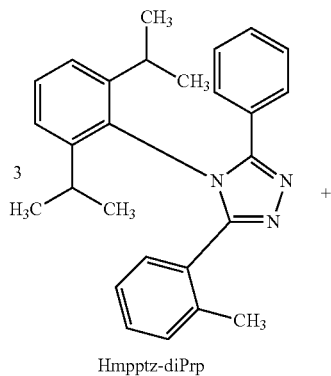

Hmpptz-diPrp

Figure 37:
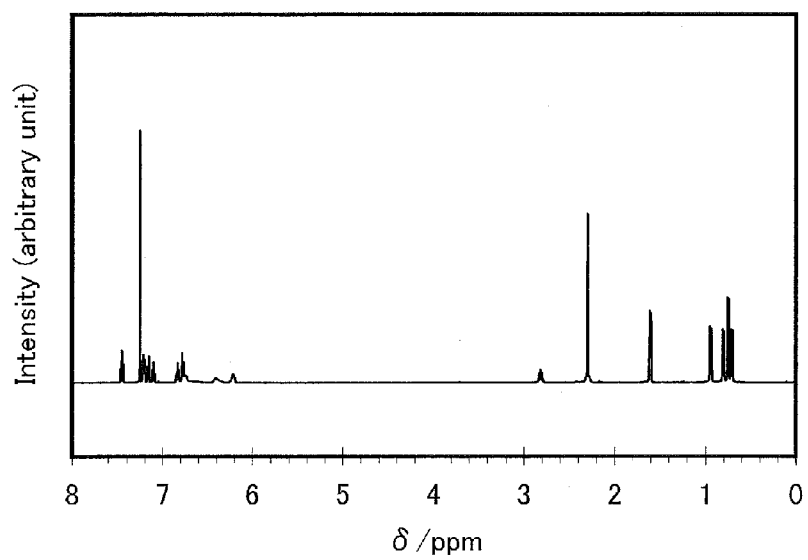
FIG. 37 shows a $^1$H-NMR chart of a phosphorescent organometallic iridium complex represented by Structural Formula (105).

An analysis result by nuclear magnetic resonance (¹H-NMR) spectroscopy of the yellow powder obtained in Step 2 is described below. FIG. 37 shows the ¹H-NMR chart. These results revealed that [Ir(mpptz-diPrp)₃] (abbreviation), the phosphorescent organometallic iridium complex which is one embodiment of the present invention represented by Structural Formula (105), was obtained in Synthesis Example 3.

1H-NMR. δ(CDCl₃): 0.69-0.71 (d, 3H), 0.73-0.76 (d, 3H), 0.78-0.81 (d, 3H), 0.92-0.95 (d, 3H), 2.24-2.29 (m, 1H), 2.30 (s, 3H), 2.79-2.85 (m, 1H), 6.16-6.18 (d, 1H), 6.47-6.52 (t, 1H), 6.67-6.71 (t, 1H), 6.77-6.79 (d, 1H), 6.81-6.84 (t, 1H), 6.89-6.91 (d, 1H), 7.09-7.13 (t, 1H), 7.15-7.17 (t, 1H), 7.19-7.22 (q, 2H), 7.43-7.47 (t, 1H).

Figure 38:
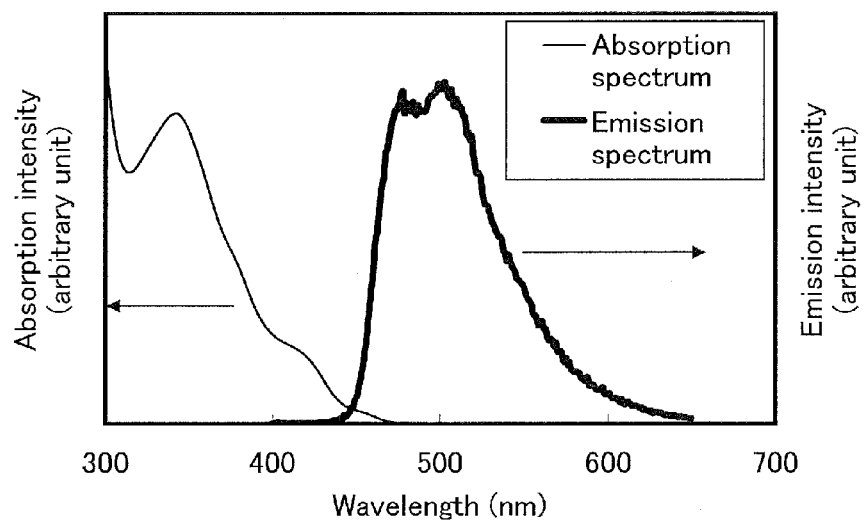
FIG. 38 shows an ultraviolet-visible absorption spectrum and an emission spectrum of a phosphorescent organometallic iridium complex represented by Structural Formula (105).

Next, an ultraviolet-visible absorption spectrum (hereinafter, simply referred to as an "absorption spectrum") of a dichloromethane solution of [Ir(mpptz-diPrp)₃] (abbreviation) and an emission spectrum thereof were measured. The measurement of the absorption spectrum was conducted at room temperature, for which an ultraviolet-visible light spectrophotometer (V550 type manufactured by Japan Spectroscopy Corporation) was used and the dichloromethane solution (0.643 mmol/L) was put in a quartz cell. In addition, the measurement of the emission spectrum was conducted at room temperature, for which a fluorescence spectrophotometer (FS920 manufactured by Hamamatsu Photonics K. K.) was used and the degassed toluene solution (0.643 mmol/L) was put in a quartz cell. Measurement results of the obtained absorption and emission spectra are shown in FIG. 38, in which the horizontal axis represents wavelength and the vertical axes represent absorption intensity and emission intensity. In FIG. 38 where there are two solid lines, the thin line represents the absorption spectrum and the thick line represents the emission spectrum. Note that the absorption spectrum in FIG. 38 is the results obtained in such a way that the absorption spectrum measured by putting only dichloromethane in a quartz cell was subtracted from the absorption spectrum measured by putting the dichloromethane solution (0.062 mmol/L) in a quartz cell.

As shown in FIG. 38, [Ir(mpptz-diPrp)₃] (abbreviation), the phosphorescent organometallic iridium complex that is one embodiment of the present invention, has emission peaks at 480 nm and 503 nm, and blue green light emission was observed from the dichloromethane solution.

Next, [Ir(mpptz-diPrp)₃] (abbreviation) obtained in this example was analyzed by liquid chromatography mass spectrometry (LC/MS).

The LC/MS analysis was carried out with Acquity UPLC (produced by Waters Corporation) and Xevo G2 T of MS (produced by Waters Corporation).

In the MS analysis, ionization was carried out by an electrospray ionization (ESI) method. At this time, the capillary voltage and the sample cone voltage were set to 3.0 kV and 30 V, respectively, and detection was performed in a positive mode. A component with m/z of 1376.65 which underwent the ionization under the above-described conditions was collided with an argon gas in a collision cell to dissociate into product ions. Energy (collision energy) for the collision with argon was 70 eV. The mass range for the measurement was m/z=100 to 1500.

Figure 39:
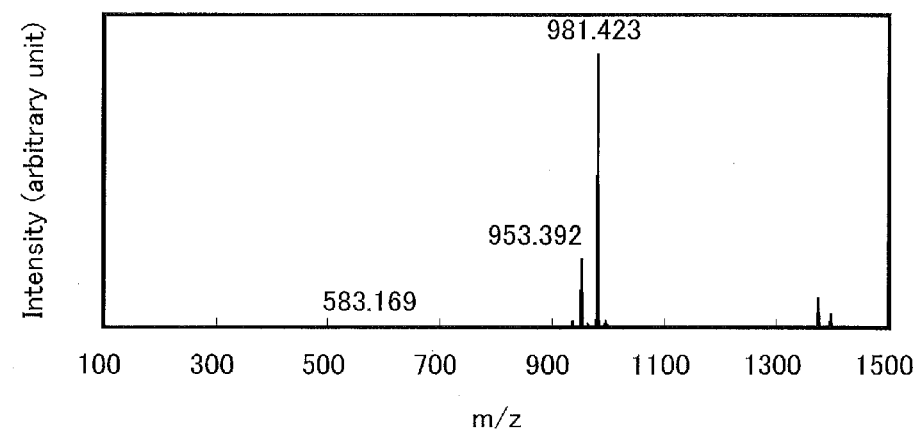
FIG. 39 shows LC/MS measurement results of a phosphorescent organometallic iridium complex represented by Structural Formula (105).

The detection result of the dissociated product ions by time-of-flight (TOF) MS are shown in FIG. 39.

The results in FIG. 39 show that product ions of [Ir(mpptz-diPrp)₃] (abbreviation), the phosphorescent organometallic iridium complex that is one embodiment of the present invention represented by Structural Formula (105), were detected mainly around m/z 981.42 and m/z 953.39. Note that the results in FIG. 39 show characteristics derived from [Ir(mpptz-diPrp)₃] (abbreviation) and therefore can be regarded as important data for identifying [Ir(mpptz-diPrp)₃] (abbreviation) contained in the mixture.

It is presumed that the product ion around m/z 981.42 is a cation in a state where one Hmpptz-diPrp (abbreviation), which is the ligand, was eliminated from the compound represented by Structural Formula (105), and this is characteristic of the phosphorescent organometallic iridium complex that is one embodiment of the present invention. It is presumed that the product ion around m/z 953.39 resulted from elimination of two methyl groups from the product ion around m/z 981.42, which suggests that [Ir(mpptz-diPrp)₃] (abbreviation), the organometallic iridium complex that is one embodiment of the present invention, includes a methyl group.

EXAMPLE 7

SYNTHESIS EXAMPLE 4

In this example, a synthesis method of a phosphorescent organometallic iridium complex tris{2-[5-(2,3-dimethylphenyl)-4-(2,6-dimethylphenyl)-4H-1,2,4-triazol-3-yl-κN2]phenyl-κC}iridium(III) (abbreviation: [Ir(2,3dmpptz-dmp)₃]), which is one embodiment of the present invention represented by Structural Formula (112) in Embodiment 1, is described. A structure of [Ir(2,3dmpptz-dmp)₃] (abbreviation) is shown below.

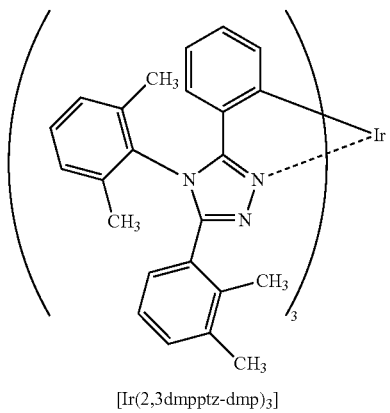

[Ir(2,3dmpptz-dmp)₃]

Step 1: Synthesis of 1-(2,3-Dimethylbenzoyl)-2-benzoylhydrazine

First, 9.4 g (69.0 mmol) of benzoylhydrazine and 50 mL of N-methyl-2-pyrrolidinone (NMP) were put into a 300-mL three-neck flask and stiffed under nitrogen flow while being cooled with ice. To this mixed solution, a mixed solution of 13.0 g (77.1 mmol) of 2,3-dimethylbenzoyl chloride and 10 mL of NMP was slowly added dropwise, and the mixture was stiffed at room temperature for 24 hours. After reaction for the predetermined time, this reacted solution was slowly added to 500 mL of water, so that a white solid was precipitated. The precipitated solid was washed by repeating twice ultrasonic cleaning in which water and then 1M hydrochloric acid were used. Then, ultrasonic cleaning using hexane was performed, so that 16.9 g of a white solid of 1-(2,3-dimethylbenzoyl)-2-benzoylhydrazine was obtained in a yield of 91%. A synthesis scheme of Step 1 is shown in (d-1).

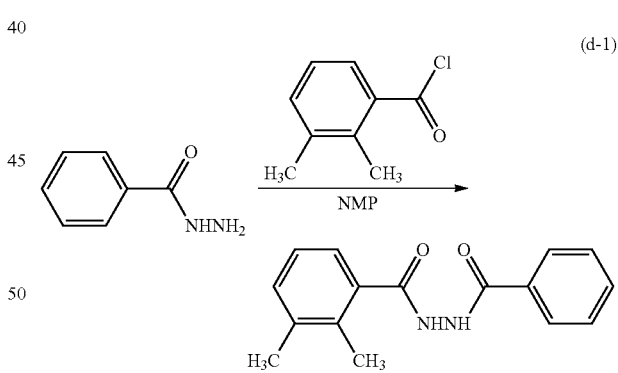

Step 2: Synthesis of [Chloro(2,3-dimethylphenyl)methanone][chloro(phenyl)methylidene]hydrazone Next, 16.9 g (62.9 mmol) of 1-(2,3-dimethylbenzoyl)-2-benzoylhydrazine obtained in Step 1 and 330 mL of toluene were put into a 1-L three-neck flask. To this mixed solution, 50.0 g (240.1 mmol) of phosphorus pentachloride was added and the mixture was heated and stirred at 120° C. for 17 hours. After reaction for the predetermined time, this reacted solution was slowly added to 1 L of water, and the mixture was stirred at room temperature for 30 minutes. An organic layer was collected, and this organic layer was slowly added to 1 L of a 1M aqueous solution of potassium hydroxide and the mixture was stirred at room temperature for 30 minutes. Further, this organic layer was washed with a saturated aqueous solution of sodium hydrogen carbonate and then with pure water. The organic layer was collected and dried with magnesium sulfate and then the solvent was distilled off, so that 21.2 g of a yellow liquid of [chloro(2,3-dimethylphenyl)methanone] [chloro(phenyl)methylidene]hydrazone was obtained in a crude yield of 110%. A synthesis scheme of Step 2 is shown in (d-2).

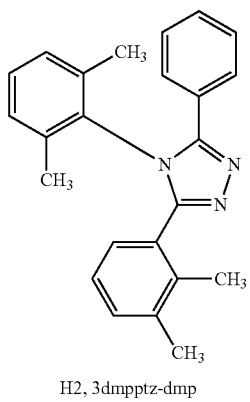

(d-2)

Step 3: Synthesis of 3-Phenyl-4-(2,6-dimethylphenyl)-5-(2,3-dimethylphenyl)-1,2,4-4H-triazole (abbreviation: H2,3dmpptz-dmp Into a 500-mL three-neck flask were put 21.2 g (69.5 mmol) of [chloro(2,3-dimethylphenyl)methanone][chloro(phenyl)methylidene]hydrazone obtained in Step 2, 30.0 g (247.6 mmol) of 2,6-dimethylaniline, and 170 mL of N,N-dimethylaniline, and the mixture was heated and stirred at 150° C. for 24 hours. After reaction for the predetermined time, the reacted solution was slowly poured into 1M hydrochloric acid and the mixture was stirred for 30 minutes, so that a yellow solid was precipitated. This yellow solid was collected by suction filtration. This solid was purified by silica gel column chromatography. As developing solvents, first, a mixed solvent of hexane and ethyl acetate in a ratio of 2:1 was used, and then only ethyl acetate was used. An objective fraction obtained was concentrated to give a white solid. This solid was recrystallized with ethyl acetate to give 9.0 g of H2,3dmpptz-dmp (abbreviation), an objective 4H-triazole derivative, in a yield of 37%. A synthesis scheme of Step 3 is shown in (d-3).

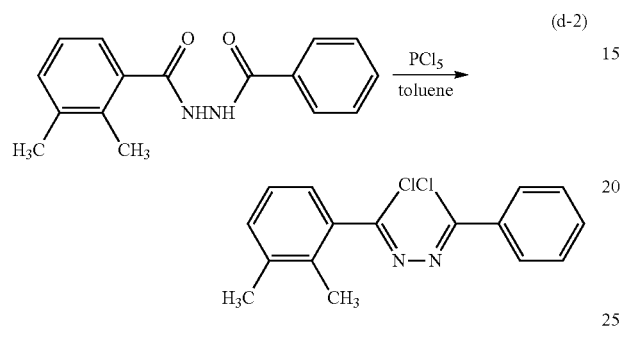

(d-3)

Step 4: Synthesis of Tris {2-[5-(2,3-dimethylphenyl)-4-(2,6-dimethylphenyl)-4H-1,2,4-triazol-3-yl-κN2]phenyl-κC}iridium(III) (abbreviation: [Ir(2,3dmpptz-dmp)₃]

Into a container for high-temperature heating were put 3.0 g (8.48 mmol) of H2,3dmpptz-dmp (abbreviation), which was the ligand obtained in Step 3, and 0.83 g (1.67 mmol) of tris(acetylacetonato)iridium(III), and degasification was carried out.

The mixture in the reaction container was heated and stirred at 250° C. for 48 hours under Ar flow. The reacted mixture was washed with dichloromethane to give a yellow solid. This solid was recrystallized with toluene, so that 0.4 g of a yellow solid of [Ir(2,3dmpptz-dmp)₃] (abbreviation), the phosphorescent organometallic iridium complex which is one embodiment of the present invention, was obtained in a yield of 19%. A synthesis scheme of Step 4 is shown in (d-4).

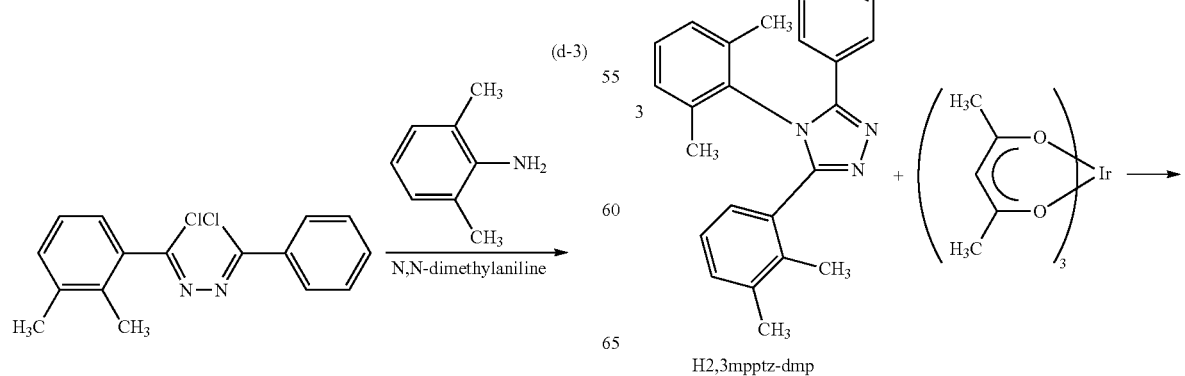

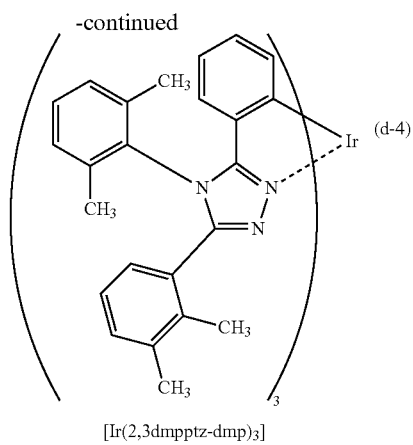

[Ir(2,3dmpptz-dmp)₃]

Figure 40:
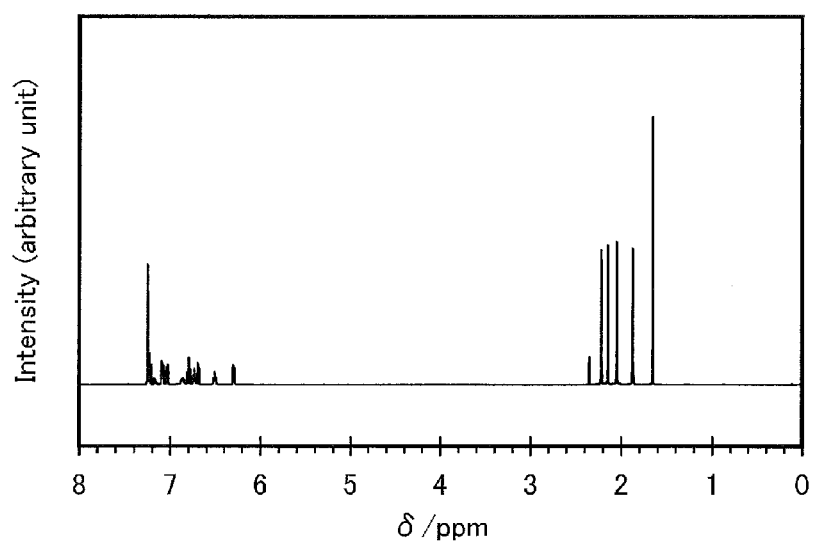
FIG. 40 shows a $^1$H-NMR chart of a phosphorescent organometallic iridium complex represented by Structural Formula (112).

An analysis result by nuclear magnetic resonance (¹H-NMR) spectroscopy of the yellow solid obtained in Step 4 is described below. FIG. 40 shows the ¹H-NMR chart. These results revealed that [Ir(2,3dmpptz-dmp)₃] (abbreviation), the phosphorescent organometallic iridium complex which is one embodiment of the present invention represented by Structural Formula (112), was obtained in Synthesis Example 4.

¹H-NMR. δ(d-toluene): 1.85 (s, 3H), 2.05 (s, 3H), 2.15 (s, 3H), 2.20 (s, 3H), 6.28-6.31 (d, 1H), 6.48-6.53 (d, 1H), 6.68-6.70 (d, 1H), 6.71-6.78 (t, 1H), 6.78-6.82 (t, 1H), 6.84-6.88 (m, 1H), 7.01-7.15 (d, 1H), 7.07-7.11 (d, 2H), 7.21-7.25 (m, 1H).

Figure 41:
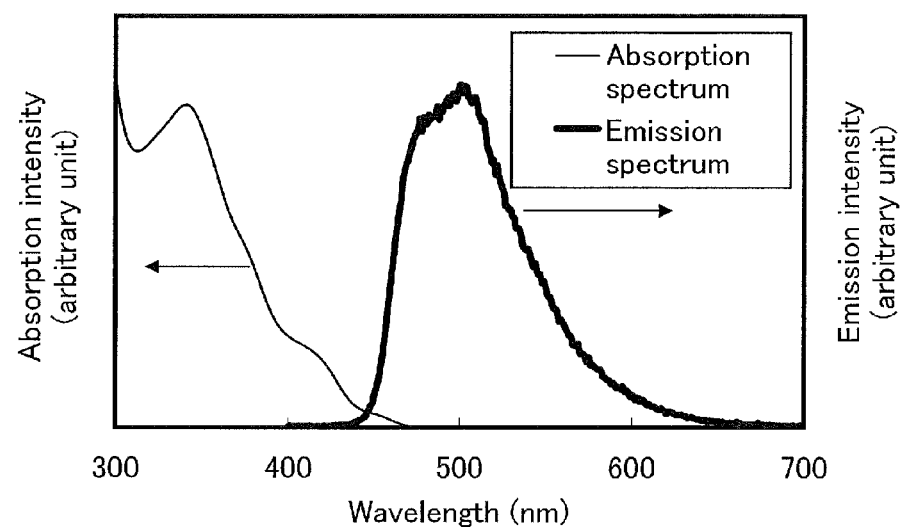
FIG. 41 shows an ultraviolet-visible absorption spectrum and an emission spectrum of a phosphorescent organometallic iridium complex represented by Structural Formula (112).

Next, an ultraviolet-visible absorption spectrum (hereinafter, simply referred to as an "absorption spectrum") of a toluene solution of [Ir(2,3dmpptz-dmp)₃] (abbreviation) and an emission spectrum thereof were measured. The measurement of the absorption spectrum was conducted at room temperature, for which an ultraviolet-visible light spectrophotometer (V550 type manufactured by Japan Spectroscopy Corporation) was used and the toluene solution (0.98 mmol/L) was put in a quartz cell. In addition, the measurement of the emission spectrum was conducted at room temperature, for which a fluorescence spectrophotometer (FS920 manufactured by Hamamatsu Photonics K. K.) was used and the degassed toluene solution (0.98 mmol/L) was put in a quartz cell. Measurement results of the obtained absorption and emission spectra are shown in FIG. 41, in which the horizontal axis represents wavelength and the vertical axes represent absorption intensity and emission intensity. In FIG. 41 where there are two solid lines, the thin line represents the absorption spectrum and the thick line represents the emission spectrum. Note that the absorption spectrum in FIG. 41 is the results obtained in such a way that the absorption spectrum measured by putting only dichloromethane in a quartz cell was subtracted from the absorption spectrum measured by putting the dichloromethane solution (0.062 mmol/L) in a quartz cell.

As shown in FIG. 41, [Ir(2,3dmpptz-dmp)₃] (abbreviation), the phosphorescent organometallic iridium complex that is one embodiment of the present invention, has emission peaks at 480 nm and 501 nm, and blue green light emission was observed from the toluene solution.

Further, [Ir(2,3dmpptz-dmp)₃] (abbreviation) obtained in this example was analyzed by liquid chromatography mass spectrometry (LC/MS).

The LC/MS analysis was carried out with Acquity UPLC (produced by Waters Corporation) and Xevo G2 T of MS (produced by Waters Corporation).

In the MS analysis, ionization was carried out by an electrospray ionization (ESI) method. At this time, the capillary voltage and the sample cone voltage were set to 3.0 kV and 30 V, respectively, and detection was performed in a positive mode. A component with m/z of 1250.52 which underwent the separation and the ionization was collided with an argon gas in a collision cell to dissociate into product ions. Energy (collision energy) for the collision with argon was 50 eV. The mass range for the measurement was m/z=30 to 1500.

Figure 42:
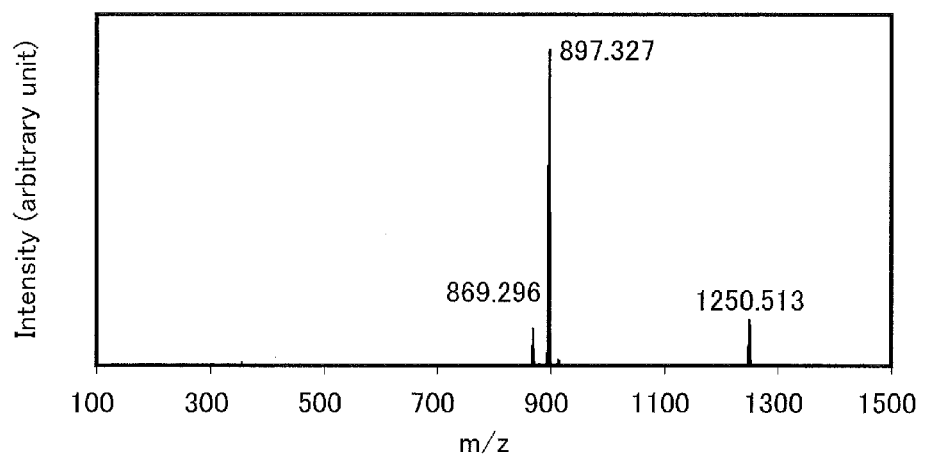
FIG. 42 shows LC/MS measurement results of a phosphorescent organometallic iridium complex represented by Structural Formula (112).

The detection result of the dissociated product ions by time-of-flight (TOF) MS are shown in FIG. 42.

The results in FIG. 42 show that product ions of [Ir(2,3dmpptz-dmp)₃] (abbreviation), the phosphorescent organometallic iridium complex that is one embodiment of the present invention represented by Structural Formula (112), were detected mainly around m/z 897.33 and m/z 869.23. Note that the results in FIG. 42 show characteristics derived from [Ir(2,3dmpptz-dmp)₃] (abbreviation) and therefore can be regarded as important data for identifying [Ir(2,3dmpptz-dmp)₃] (abbreviation) contained in the mixture.

It is presumed that the product ion around m/z 897.33 is a cation in a state where one H2,3dmpptz-dmp (abbreviation), which is the ligand, was eliminated from the compound represented by Structural Formula (112), and this is characteristic of the phosphorescent organometallic iridium complex that is one embodiment of the present invention. It is presumed that the product ion around m/z 869.23 resulted from elimination of two methyl groups from the product ion around m/z 897.33, which suggests that [Ir(2,3dmpptz-dmp)₃] (abbreviation), the phosphorescent organometallic iridium complex that is one embodiment of the present invention, includes a methyl group.

EXAMPLE 8

SYNTHESIS EXAMPLE 5

In this example, a synthesis method of a phosphorescent organometallic iridium complex tris{2-[4-(2,6-dimethylphenyl)-5-(2,4,6-trimethylphenyl)-4H-1,2,4-triazol-3-yl-κN2]phenyl-κC}iridium(III) (abbreviation: [Ir(tmpptz-dmp)₃]), which is one embodiment of the present invention represented by Structural Formula (121) in Embodiment 1, is described. A structure of [Ir(tmpptz-dmp)₃] (abbreviation) is shown below.

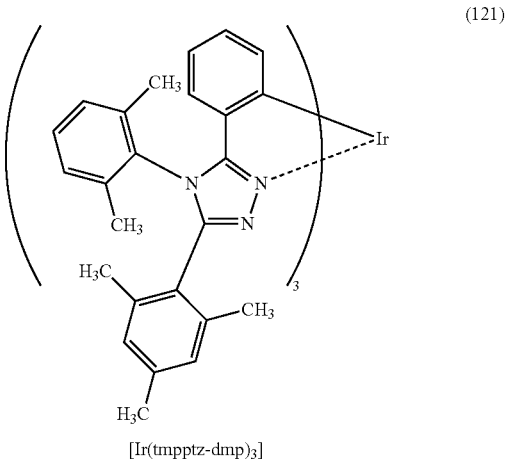

[Ir(tmpptz-dmp)₃]

Step 1: Synthesis of 1-(2,4,6-Trimethylbenzoyl)-2-benzoylhydrazine

First, 16.7 g (123.3 mmol) of benzoylhydrazine and 100 mL of N-methyl-2-pyrrolidinone (NMP) were put into a 300-mL three-neck flask and stiffed under nitrogen flow while being cooled with ice. To this mixed solution, a mixed solution of 25.0 g (137.3 mmol) of 2,4,6-trimethylbenzoyl chloride and 20 mL of NMP was slowly added dropwise, and the mixture was stiffed at room temperature for 24 hours. After reaction for the predetermined time, this reacted solution was slowly added to 500 mL of water, so that a white solid was precipitated. The precipitated solid was washed by repeating twice ultrasonic cleaning in which water and then 1M hydrochloric acid were used. Then, ultrasonic cleaning using hexane was performed, so that 22.7 g of a white solid of 1-(2,4,6-trimethylbenzoyl)-2-benzoylhydrazine was obtained in a yield of 65%. A synthesis scheme of Step 1 is shown in (e-1).

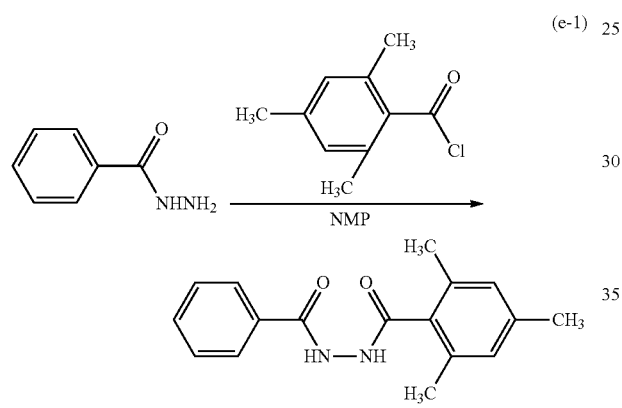

Step 2: Synthesis of [Chloro(2,4,6-trimethylphenyl)methanone][chloro(phenyl)methylidene]hydrazone Next, 11.6 g (41.1 mmol) of 1-(2,4,6-trimethylbenzoyl)-2-benzoylhydrazine obtained in Step 1 and 250 mL of toluene were put into a 1-L three-neck flask. To this mixed solution, 25.0 g (120.0 mmol) of phosphorus pentachloride was added and the mixture was heated and stirred at 120° C. for 8 hours. After reaction for the predetermined time, this reacted solution was slowly added to 500 mL of water, and the mixture was stirred at room temperature for 30 minutes. An organic layer was collected, and this organic layer was slowly added to 1 L of a 1M aqueous solution of potassium hydroxide and the mixture was stirred at room temperature for 30 minutes. Further, this organic layer was washed with a saturated aqueous solution of sodium hydrogen carbonate and then with pure water. The organic layer was collected and dried with magnesium sulfate and then the solvent was distilled off, so that a yellow oily substance was obtained. This oily substance was purified by silica gel chromatography. As a developing solvent, a mixed solvent of hexane and ethyl acetate in a ratio of 5:1 was used. The obtained fraction was concentrated to give 7.2 g of a yellow liquid of [chloro(2,4,6-trimethylphenyl)methanone][chloro(phenyl)methylidene]hydrazone in a yield of 55%. A synthesis scheme of Step 2 is shown in (e-2).

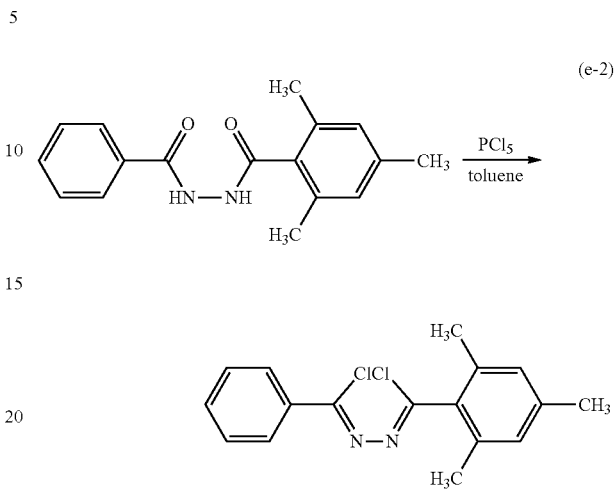

Step 3: Synthesis of 3-Phenyl-4-(2,6-dimethylphenyl)-5-(2,4,6-trimethylphenyl)-1,2,4-4H-triazole (abbreviation: Htmpptz-dmp)

Into a 200-mL three-neck flask were put 7.0 g (21.9 mmol) of [chloro(2,4,6-trimethylphenyl)methanone][chloro(phenyl)methylidene]hydrazone obtained in Step 2, 8.0 g (65.7 mmol) of 2,6-dimethylaniline, and 50 mL of N,N-dimethylaniline, and the mixture was heated and stirred at 170° C. for 24 hours. After reaction for the predetermined time, the reacted solution was slowly poured into 1M hydrochloric acid and the mixture was stirred for 30 minutes. Dichloromethane was poured into this mixture and an organic layer was extracted. This organic layer was washed with a saturated aqueous solution of sodium hydrogen carbonate and pure water and dried with magnesium sulfate; then, the solvent was distilled off, so that a yellow oily substance was obtained. This oily substance was purified by silica gel column chromatography. As a developing solvent, a mixed solvent of hexane and ethyl acetate in a ratio of 3:1 was used. The obtained fraction was concentrated to give 2.3 g of a white solid of Htmpptz-dmp, an objective 4H-triazole derivative, in a yield of 27%. A synthesis scheme of Step 3 is shown in (e-3).

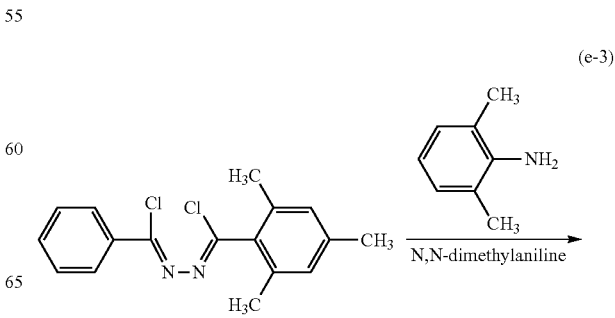

-continued

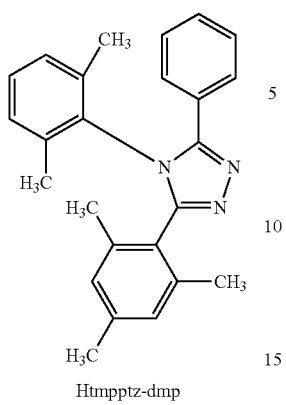

Htmpptz-dmp

Step 4: Synthesis of Tris{2-[4-(2,6-dimethylphenyl)-5-(2,4,6-trimethylphenyl)-4H-1,2,4-triazol-3-yl-κN2]phenyl-κC}iridium(III) (abbreviation: [Ir(tmpptz-dmp)₃]

Into a container for high-temperature heating were put 2.2 g (6.0 mmol) of Htmpptz-dmp (abbreviation), which was the ligand obtained in Step 3, and 0.6 g (1.2 mmol) of tris(acetylacetonato)iridium(III), and degasification was carried out. The mixture was in the reaction container heated and stirred at 250° C. for 48 hours under Ar flow. The reacted mixture was purified by silica gel chromatography. As a developing solvent, a mixed solvent of hexane and ethyl acetate in a ratio of 2:1 was used. The obtained fraction was concentrated to give a yellow solid. This solid was recrystallized with ethyl acetate, so that 0.7 g of a yellowish green solid was obtained in a yield of 27%. By a train sublimation method, this solid was purified. The purification by sublimation was performed by heating at 310° C. under a pressure of 3.5 Pa with an Ar flow rate of 5 mL/min. After the purification by sublimation, 0.5 g of a yellow solid of [Ir(tmpptz-dmp)₃] (abbreviation), the phosphorescent organometallic iridium complex which is one embodiment of the present invention, was obtained in a yield of 76%. A synthesis scheme of Step 4 is shown in (e-4).

(e-4)

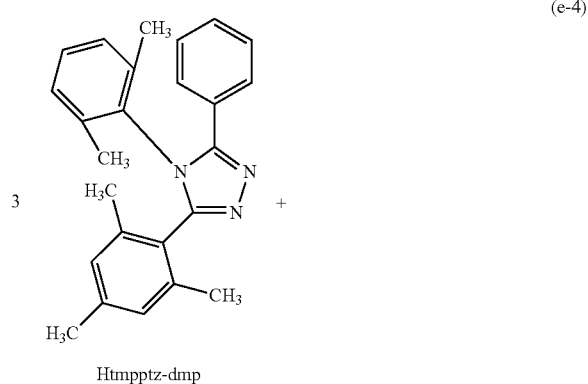

Htmpptz-dmp

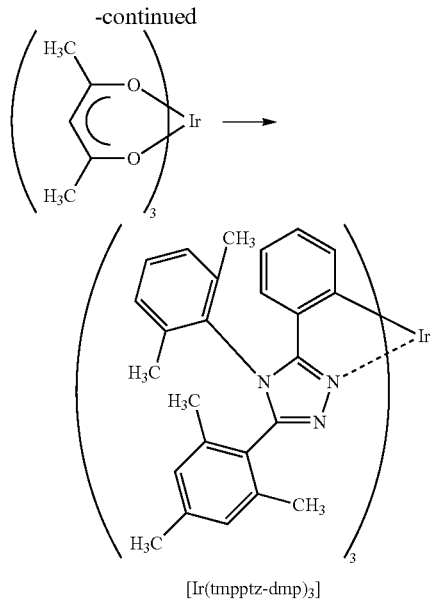

[Ir(tmpptz-dmp)₃]

Figure 43:
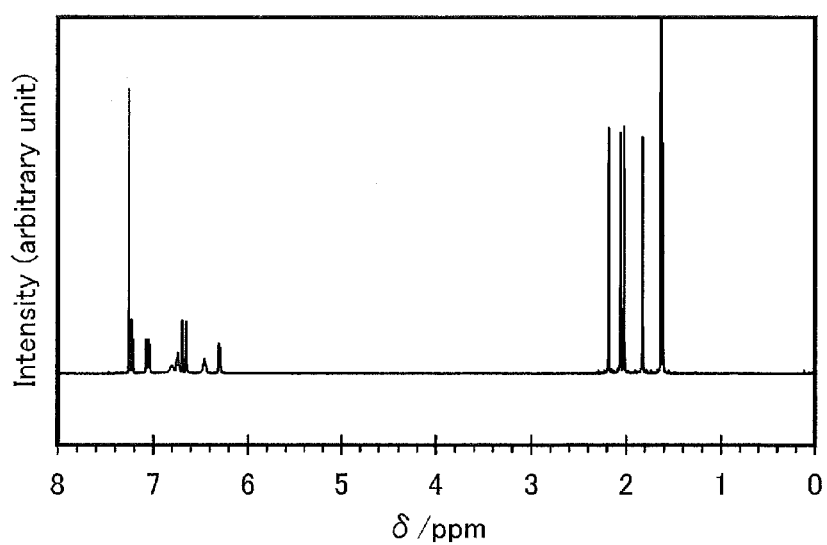
FIG. 43 shows a $^1$H-NMR chart of a phosphorescent organometallic iridium complex represented by Structural Formula (121).

An analysis result by nuclear magnetic resonance (¹H-NMR) spectroscopy of the yellow solid obtained in Step 4 is described below. FIG. 43 shows the ¹H-NMR chart. These results revealed that [Ir(tmpptz-dmp)₃] (abbreviation), the phosphorescent organometallic iridium complex which is one embodiment of the present invention represented by Structural Formula (121), was obtained in Synthesis Example 5.

¹H-NMR. δ(CDCl₃): 1.61 (s, 3H), 1.83 (s, 3H), 2.03 (s, 3H), 2.08 (s, 3H), 2.18 (s, 3H), 6.28-6.31 (d, 1H), 6.42-6.48 (t, 1H), 6.64 (s, 1H), 6.69 (s, 1H), 6.72-6.76 (t, 1H), 6.78-6.82 (m, 1H), 7.02-7.09 (m, 2H), 7.21-7.25 (t, 1H).

Figure 44:
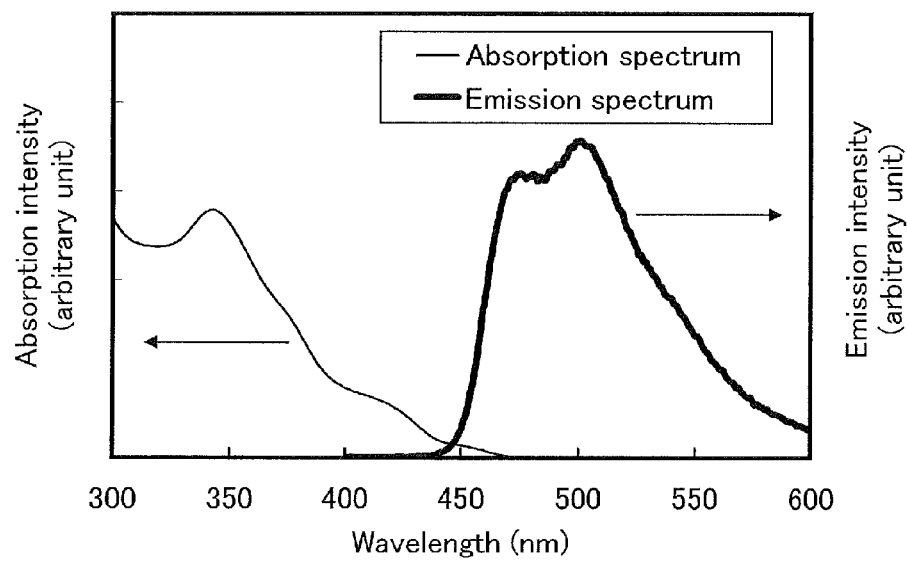
FIG. 44 shows an ultraviolet-visible absorption spectrum and an emission spectrum of a phosphorescent organometallic iridium complex represented by Structural Formula (121).

Next, an ultraviolet-visible absorption spectrum (hereinafter, simply referred to as an "absorption spectrum") of a toluene solution of [Ir(tmpptz-dmp)₃] (abbreviation) and an emission spectrum thereof were measured. The measurement of the absorption spectrum was conducted at room temperature, for which an ultraviolet-visible light spectrophotometer (V550 type manufactured by Japan Spectroscopy Corporation) was used and the toluene solution (0.98 mmol/L) was put in a quartz cell. In addition, the measurement of the emission spectrum was conducted at room temperature, for which a fluorescence spectrophotometer (FS920 manufactured by Hamamatsu Photonics K. K.) was used and the degassed toluene solution (0.98 mmol/L) was put in a quartz cell. Measurement results of the obtained absorption and emission spectra are shown in FIG. 44, in which the horizontal axis represents wavelength and the vertical axes represent absorption intensity and emission intensity. In FIG. 44 where there are two solid lines, the thin line represents the absorption spectrum and the thick line represents the emission spectrum. Note that the absorption spectrum in FIG. 44 is the results obtained in such a way that the absorption spectrum measured by putting only dichloromethane in a quartz cell was subtracted from the absorption spectrum measured by putting the dichloromethane solution (0.062 mmol/L) in a quartz cell.

As shown in FIG. 44, [Ir(tmpptz-dmp)₃] (abbreviation), the phosphorescent organometallic iridium complex that is one embodiment of the present invention, has emission peaks at 480 nm and 501 nm, and blue green light emission was observed from the toluene solution.

Further, [Ir(tmpptz-dmp)₃] (abbreviation) obtained in this example was analyzed by liquid chromatography mass spectrometry (LC/MS).

The LC/MS analysis was carried out with Acquity UPLC (produced by Waters Corporation) and Xevo G2 T of MS (produced by Waters Corporation).

In the MS analysis, ionization was carried out by an electrospray ionization (ESI) method. At this time, the capillary voltage and the sample cone voltage were set to 3.0 kV and 30 V, respectively, and detection was performed in a positive mode. The mass range for the measurement was m/z=30 to 1500.

A component with m/z of 1291.56 which underwent the separation and the ionization under the above-described conditions was collided with an argon gas in a collision cell to dissociate into product ions. Energy (collision energy) for the collision with argon was 50 eV. The detection result of the dissociated product ions by time-of-flight (TOF) MS are shown in FIG. 45.

Figure 45:
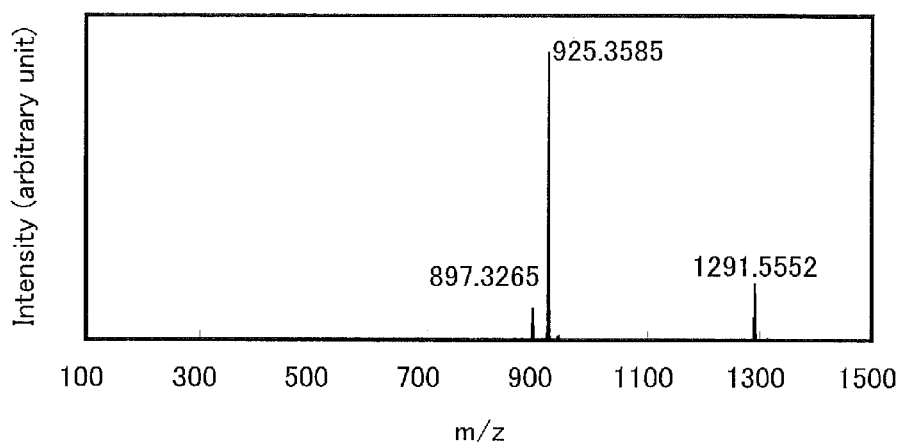
FIG. 45 shows LC/MS measurement results of a phosphorescent organometallic iridium complex represented by Structural Formula (121).

The results in FIG. 45 show that product ions of [Ir(tmpptz-dmp)₃] (abbreviation), the phosphorescent organometallic iridium complex that is one embodiment of the present invention represented by Structural Formula (121), were detected mainly around m/z 925.36 and m/z 897.33. Note that the results in FIG. 45 show characteristics derived from [Ir(tmpptz-dmp)₃] (abbreviation) and therefore can be regarded as important data for identifying [Ir(tmpptz-dmp)₃] (abbreviation) contained in the mixture.

It is presumed that the product ion around m/z 925.36 is a cation in a state where acetylacetone and a proton were eliminated from the compound represented by Structural Formula (121), and this is characteristic of the phosphorescent organometallic iridium complex that is one embodiment of the present invention. It is presumed that the product ion around m/z 897.33 resulted from elimination of two methyl groups from the product ion around m/z 925.36, which suggests that [Ir(tmpptz-dmp)₃] (abbreviation), the organometallic complex that is one embodiment of the present invention, includes a methyl group.

EXAMPLE 9

In this example, the following light-emitting elements in each of which a phosphorescent organometallic iridium complex is used for a light-emitting layer will be described: a light-emitting element 4 in which tris{2-[5-(2-methylphenyl)-4-(2,6-diisopropylphenyl)-4H-1,2,4-triazol-3-yl-κN2]phenyl-κC}iridium(III) (abbreviation: [Ir(mpptz-diPrp)₃]) represented by Structural Formula (105) is used; a light-emitting element 5 in which tris{2-[5-(2,3-dimethylphenyl)-4-(2,6-dimethylphenyl)-4H-1,2,4-triazol-3-yl-κN2]phenyl-κC}iridium(III) (abbreviation: [Ir(2,3dmpptz-dmp)₃]) represented by Structural Formula (112) is used; a light-emitting element 6 in which tris{2-[4-(2,6-dimethylphenyl)-5-(2,4,6-trimethylphenyl)-4H-1,2,4-triazol-3-yl-κN2]phenyl-κC}iridium(III) (abbreviation: [Ir(tmpptz-dmp)₃]) represented by Structural Formula (121) is used; and a comparative light-emitting element in which tris{2-[5-(2-methylphenyl)-4-methyl-4H-1,2,4-triazol-3-yl-κN2]phenyl-κC}iridium(III) (abbreviation: [Ir(mpptz-Me)₃]) is used. Note that in the description of the light-emitting elements 4 to 6 and the comparative light-emitting element in this example, FIG. 13 which is used in the description of the light-emitting element 1 in Example 1 is to be referred to. Chemical formulae of materials used in this example are shown below.

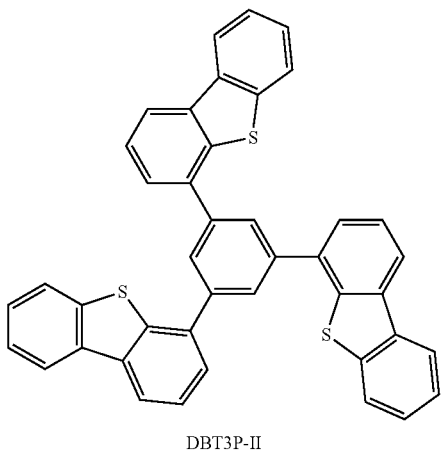

DBT3P-II

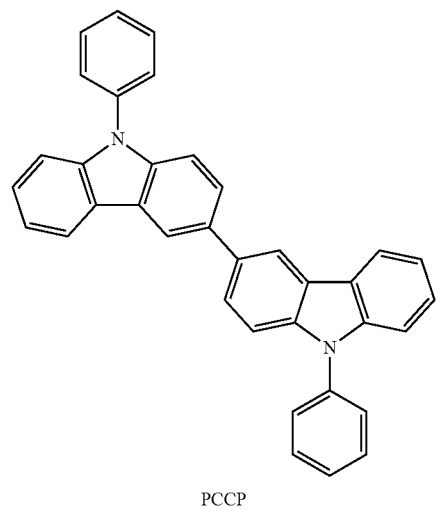

PCCP

35DCzPPy

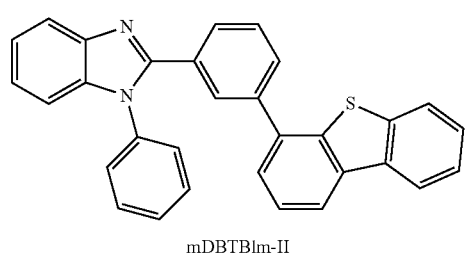

mDBTBIm-II

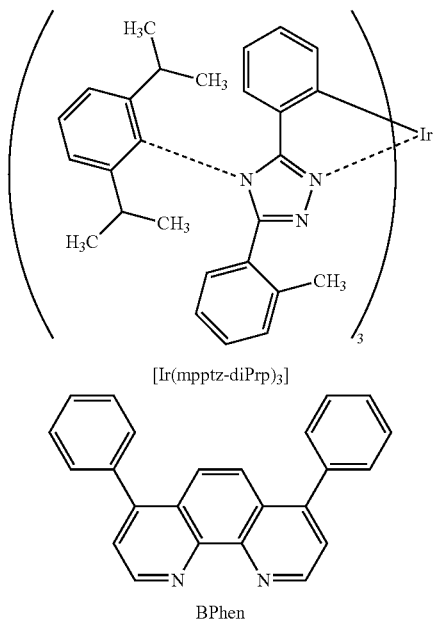

[Ir(mpptz-diPrp)₃]

BPhen

<<Fabrication of Light-emitting Elements 4 to 6 and Comparative Light-emitting Element>>

First, indium tin oxide containing silicon oxide (ITSO) was deposited over the glass substrate 1100 by a sputtering method, so that the first electrode 1101 which functions as an anode was formed. The thickness was 110 nm and the electrode area was 2 mm×2 mm Then, as pretreatment for forming the light-emitting element over the substrate 1100, UV ozone treatment was performed for 370 seconds after washing of a surface of the substrate with water and baking that was performed at 200° C. for 1 hour.

After that, the substrate was transferred into a vacuum evaporation apparatus where the pressure had been reduced to approximately $10^{-4}$ Pa, and was subjected to vacuum baking at 170° C. for 30 minutes in a heating chamber of the vacuum evaporation apparatus, and then the substrate 1100 was cooled down for about 30 minutes.

Next, the substrate 1100 was fixed to a holder provided in the vacuum evaporation apparatus so that a surface of the substrate 1100 over which the first electrode 1101 was formed faced downward. In this example, a case will be described in which the hole-injection layer 1111, the hole-transport layer 1112, the light-emitting layer 1113, the electron-transport layer 1114, and the electron-injection layer 1115 which are included in the EL layer 1102 are sequentially formed by a vacuum evaporation method.

After reducing the pressure of the vacuum evaporation apparatus to $10^{-4}$ Pa, 1,3,5-tri(dibenzothiophen-4-yl)benzene (abbreviation: DBT3P-II) and molybdenum(VI) oxide were co-evaporated with a mass ratio of DBT3P-II (abbreviation) to molybdenum oxide being 4:2, whereby the hole-injection layer 1111 was formed over the first electrode 1101. The thickness of the hole-injection layer 1111 was 60 nm Note that the co-evaporation is an evaporation method in which some different substances are evaporated from some different evaporation sources at the same time.

Next, 9-phenyl-9H-3-(9-phenyl-9H-carbazol-3-yl)carbazole (abbreviation: PCCP) was deposited by evaporation to a thickness of 20 nm, whereby the hole-transport layer 1112 was formed.

Next, the light-emitting layer 1113 was formed over the hole-transport layer 1112.

In the case of the light-emitting element 4, PCCP (abbreviation), 3,5-bis[3-(9H-carbazol-9-yl)phenyl]pyridine (abbreviation: 35DCzPPy), and tris{2-[5-(2-methylphenyl)-4-(2,6-diisopropylphenyl)-4H-1,2,4-triazol-3-yl-κN2]phenyl-κC}iridium(III) (abbreviation: [Ir(mpptz-diPrp)₃]) were deposited by co-evaporation to a thickness of 30 nm with a mass ratio of PCCP (abbreviation) to 35DCzPPy (abbreviation) and [Ir(mpptz-diPrp)₃] (abbreviation) being 1:0.3:0.1. After that, 35DCzPPy (abbreviation) and [Ir(mpptz-diPrp)₃] (abbreviation) were deposited by co-evaporation to a thickness of 10 nm with a mass ratio of 35DCzPPy (abbreviation) to [Ir(mpptz-diPrp)₃] (abbreviation) being 1:0.03. Thus, the light-emitting layer 1113 having a stacked layer structure was formed.

In the case of the light-emitting element 5, PCCP (abbreviation), 3,5-bis[3-(9H-carbazol-9-yl)phenyl]pyridine (abbreviation: 35DCzPPy), and [Ir(2,3dmpptz-dmp)₃] (abbreviation) were deposited by co-evaporation to a thickness of 30 nm with a mass ratio of PCCP (abbreviation) to 35DCzPPy (abbreviation) and [Ir(2,3dmpptz-dmp)₃] (abbreviation) being 1:0.3:0.1. After that, 35DCzPPy (abbreviation) and [Ir(2,3dmpptz-dmp)₃] (abbreviation) were deposited by co-evaporation to a thickness of 10 nm with a mass ratio of 35DCzPPy (abbreviation) to [Ir(2,3dmpptz-dmp)₃] (abbreviation) being 1:0.06. Thus, the light-emitting layer 1113 having a stacked layer structure was formed.

In the case of the light-emitting element 6, PCCP (abbreviation), 3,5-bis[3-(9H-carbazol-9-yl)phenyl]pyridine (abbreviation: 35DCzPPy), and [Ir(tmpptz-dmp)₃] (abbreviation) were deposited by co-evaporation to a thickness of 30 nm with a mass ratio of PCCP (abbreviation) to 35DCzPPy (abbreviation) and [Ir(tmpptz-dmp)₃] (abbreviation) being 1:0.3:0.06. After that, 35DCzPPy (abbreviation) and [Ir (tmpptz-dmp)₃] (abbreviation) were deposited by co-evaporation to a thickness of 10 nm with a mass ratio of 35DCzPPy (abbreviation) to [Ir(tmpptz-dmp)₃] (abbreviation) being 1:0.06. Thus, the light-emitting layer 1113 having a stacked layer structure was formed.

In the case of the comparative light-emitting element, PCCP (abbreviation), 3,5-bis[3-(9H-carbazol-9-yl)phenyl]pyridine (abbreviation: 35DCzPPy), and [Ir(mpptz-Me)₃] (abbreviation) were deposited by co-evaporation to a thickness of 30 nm with a mass ratio of PCCP (abbreviation) to 35DCzPPy (abbreviation) and [Ir(mpptz-Me)₃] (abbreviation) being 1:0.3:0.06. After that, 35DCzPPy (abbreviation) and [Ir(mpptz-Me)₃] (abbreviation) were deposited by co-evaporation to a thickness of 10 nm with a mass ratio of 35DCzPPy (abbreviation) to [Ir(mpptz-Me)₃] (abbreviation) being 1:0.06. Thus, the light-emitting layer 1113 having a stacked layer structure was formed.

Then, over the light-emitting layer 1113, 3,5-bis[3-(9H-carbazol-9-yl)phenyl]pyridine (abbreviation: 35DCzPPy) was deposited by evaporation (in the case of the light-emitting element 5, 2-[3-(dibenzothiophen-4-yl)phenyl]-1-phenyl-1H-benzimidazole (abbreviation: mDBTBIm-II) was deposited instead of 35DCzPPy (abbreviation)) to a thickness of 10 nm, and then bathophenanthroline (abbreviation: Bphen) was deposited by evaporation to a thickness of 15 nm, whereby the electron-transport layer 1114 was formed. Furthermore, lithium fluoride was deposited by evaporation to a thickness of 1 nm over the electron-transport layer 1114, whereby the electron-injection layer 1115 was formed.

Finally, aluminum was deposited by evaporation to a thickness of 200 nm over the electron-injection layer 1115 to form the second electrode 1103 serving as a cathode; thus, the light-emitting elements 4 to 6 and the comparative light-emitting element were obtained. Note that in all the above evaporation steps, evaporation was performed by a resistance-heating method.

Figure 48:
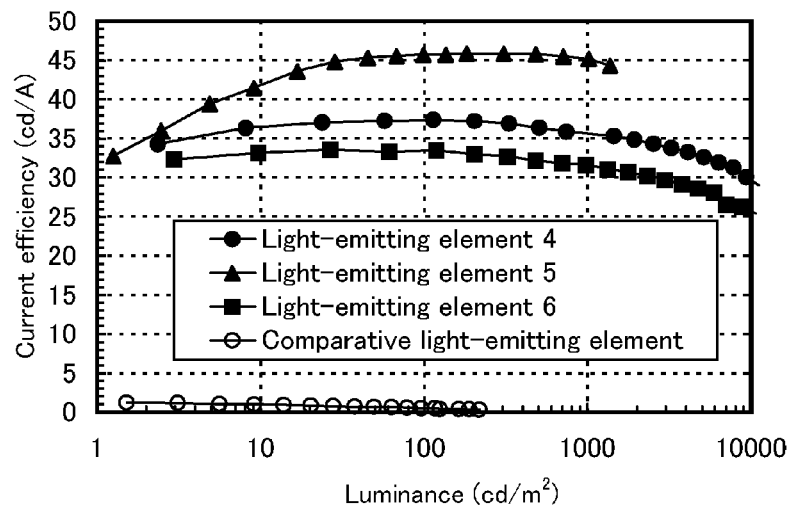
FIG. 48 shows luminance-current efficiency characteristics of light-emitting elements 4 to 6 and a comparative light-emitting element.
Figure 49:
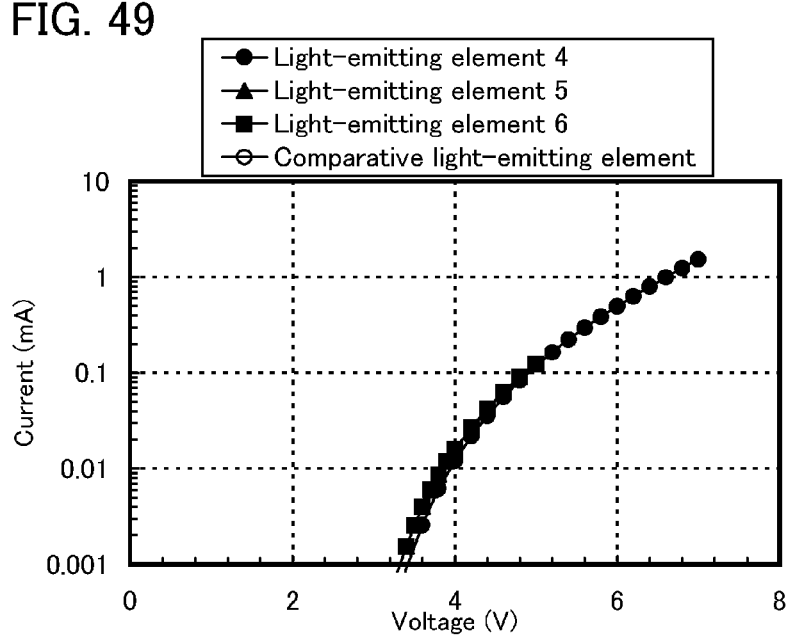
FIG. 49 shows voltage-current characteristics of light-emitting elements 4 to 6 and a comparative light-emitting element.
Figure 50:
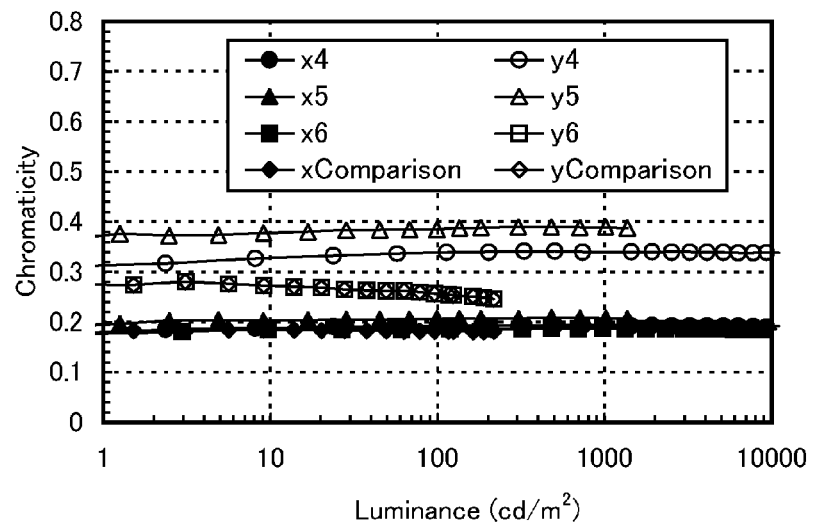
FIG. 50 shows luminance-chromaticity characteristics of light-emitting elements 4 to 6 and a comparative light-emitting element.

Element structures of the light-emitting elements 4 to 6 and the comparative light-emitting element obtained as described above are shown in Table 7.

and the comparative light-emitting element. In FIG. 48, the vertical axis represents current efficiency (cd/A) and the horizontal axis represents luminance (cd/m$^2$). FIG. 49 shows voltage-current characteristics of the light-emitting elements 4 to 6 and the comparative light-emitting element. In FIG. 49, the vertical axis represents current (mA) and the horizontal axis represents voltage (V). In addition, FIG. 50 shows lumi-

TABLE 7

| | First Electrode | Hole-injection Layer | Hole-transport Layer | Light-emitting Layer | | Electron-transport Layer | | Electron-injection Layer | Second Electrode |
|---|---|---|---|---|---|---|---|---|---|
| Light-emitting Element 4 | ITSO (110 nm) | DBT3P-II:MoO$_x$ (4:2 60 nm) | PCCP (20 nm) | *1 | *2 | 35DCzPPy (10 nm) | Bphen (15 nm) | LiF (1 nm) | Al (200 nm) |
| Light-emitting Element 5 | ITSO (110 nm) | DBT3P-II:MoO$_x$ (4:2 60 nm) | PCCP (20 nm) | *3 | *4 | mDBTBIm-II (10 nm) | Bphen (15 nm) | LiF (1 nm) | Al (200 nm) |
| Light-emitting Element 6 | ITSO (110 nm) | DBT3P-II:MoO$_x$ (4:2 60 nm) | PCCP (20 nm) | *5 | *6 | 35DCzPPy (10 nm) | Bphen (15 nm) | LiF (1 nm) | Al (200 nm) |
| Comparative Light-emitting Element | ITSO (110 nm) | DBT3P-II:MoO$_x$ (4:2 60 nm) | PCCP (20 nm) | *7 | *8 | 35DCzPPy (10 nm) | Bphen (15 nm) | LiF (1 nm) | Al (200 nm) |

*1 PCCP:35DCzPPy:[Ir(mpptz-diPrp)$_3$] (1:0.3:0.1 30 nm)
*2 35DCzPPy:[Ir(mpptz-diPrp)$_3$] (1:0.03 10 nm)
*3 PCCP:35DCzPPy:[Ir(2,3dmpptz-dmp)$_3$] (1:0.3:0.1 30 nm)
*4 35DCzPPy:[Ir(2,3dmpptz-dmp)$_3$] (1:0.06 10 nm)
*5 PCCP:35DCzPPy:[Ir(tmpptz-dmp)$_3$] (1:0.3:0.06 30 nm)
*6 35DCzPPy:[Ir(tmpptz-dmp)$_3$] (1:0.06 10 nm)
*7 PCCP:35DCzPPy:[Ir(mpptz-Me)$_3$] (1:0.3:0.06 30 nm)
*8 35DCzPPy:[Ir(mpptz-Me)$_3$] (1:0.06 10 nm)

Further, the fabricated light-emitting elements 4 to 6 and the comparative light-emitting element were sealed in a glove box containing a nitrogen atmosphere so as not to be exposed to the air (specifically, a sealant was applied onto an outer edge of the element and heat treatment was performed at 80° C. for 1 hour at the time of sealing).

<<Operation Characteristics of Light-emitting Elements 4 to 6 and Comparative Light-emitting Element>>

Operation characteristics of the fabricated light-emitting elements 4 to 6 and the comparative light-emitting element were measured. Note that the measurement was carried out at room temperature (under an atmosphere in which the temperature was kept at 25° C.).

Figure 46:
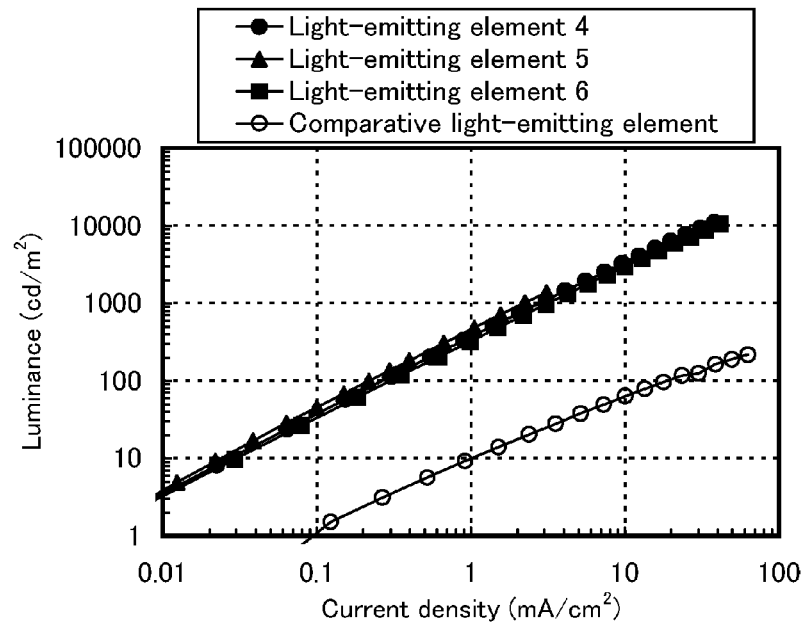
FIG. 46 shows current density-luminance characteristics of light-emitting elements 4 to 6 and a comparative light-emitting element.
Figure 47:
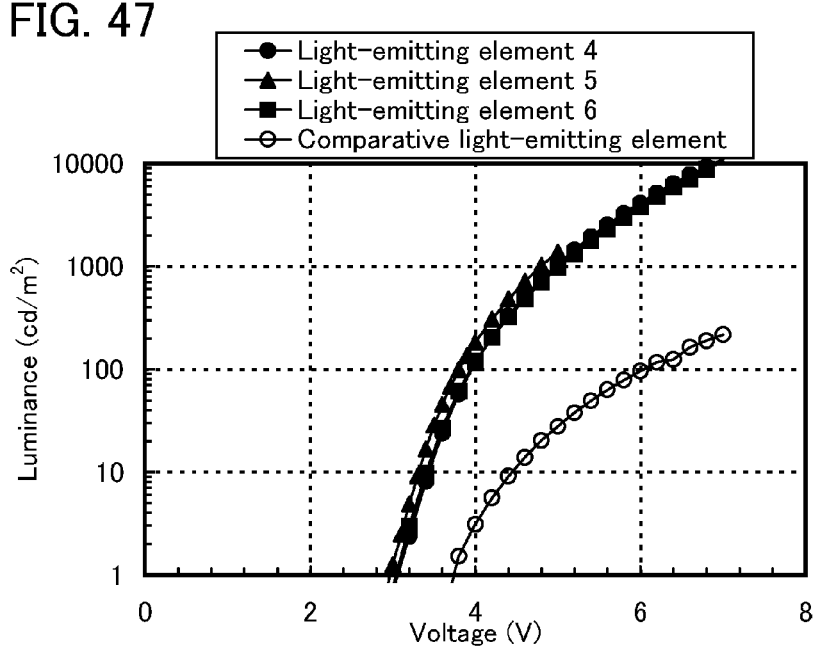
FIG. 47 shows voltage-luminance characteristics of light-emitting elements 4 to 6 and a comparative light-emitting element.

FIG. 46 shows current density-luminance characteristics of the light-emitting elements 4 to 6 and the comparative light-emitting element. In FIG. 46, the vertical axis represents luminance (cd/m$^2$) and the horizontal axis represents current density (mA/cm$^2$). FIG. 47 shows voltage-luminance characteristics of the light-emitting elements 4 to 6 and the comparative light-emitting element. In FIG. 47, the vertical axis represents luminance (cd/m$^2$) and the horizontal axis represents voltage (V). Further, FIG. 48 shows luminance-current efficiency characteristics of the light-emitting elements 4 to 6 nance-chromaticity characteristics of the light-emitting elements 4 to 6 and the comparative light-emitting element. In FIG. 50, the vertical axis represents chromaticity coordinate and the horizontal axis represents luminance (cd/m$^2$).

FIG. 48 reveals high efficiency of the light-emitting elements 4 to 6 respectively including, in part of their light-emitting layers, [Ir(mpptz-diPrp)$_3$] (abbreviation) represented by Structural Formula (105), [Ir(2,3dmpptz-dmp)$_3$] (abbreviation) represented by Structural Formula (112), and [Ir(tmpptz-dmp)$_3$] (abbreviation) represented by Structural Formula (121), which are the phosphorescent organometallic iridium complexes that are embodiments of the present invention. Table 8 shows initial values of main characteristics of the light-emitting elements 4 to 6 and the comparative light-emitting element at a luminance of about 1000 cd/m$^2$.

TABLE 8

| | Voltage (V) | Current (mA) | Current Density (mA/cm$^2$) | Chromaticity (x, y) | Luminance (cd/m$^2$) | Current Efficiency (cd/A) | Power Efficiency (lm/W) | Quantum Efficiency (%) |
|---|---|---|---|---|---|---|---|---|
| Light-emitting Element 4 | 4.8 | 0.08 | 2.1 | (0.19, 0.34) | 740 | 36 | 23 | 16 |
| Light-emitting Element 5 | 4.8 | 0.09 | 2.3 | (0.21, 0.39) | 1000 | 45 | 30 | 20 |
| Light-emitting Element 6 | 5.0 | 0.12 | 3.1 | (0.19, 0.31) | 980 | 32 | 20 | 15 |
| Comparative Light-emitting Element | 8.0 | 9.5 | 240 | (0.18, 0.23) | 390 | 0.17 | 0.065 | 0.090 |

The above results show that the light-emitting elements 4 to 6 fabricated in this example are high-luminance light-emitting elements having high current efficiency. In the case of the comparative light-emitting element, while the voltage-current characteristics show that recombination occurred in the light-emitting layer, the luminance-current efficiency characteristics show low current efficiency. This proved that a phosphorescent organometallic iridium complex whose ligand is a 4H-1,2,4-triazole compound having a substituted or unsubstituted phenyl group at the 4-position, which is one embodiment of the present invention, has higher light-emitting characteristics and is more preferable than a phosphorescent organometallic iridium complex whose ligand is a 4H-1,2,4-triazole compound having a methyl group at the 4-position. Moreover, it can be found that the light-emitting elements exhibit blue green light emission.

Figure 51:
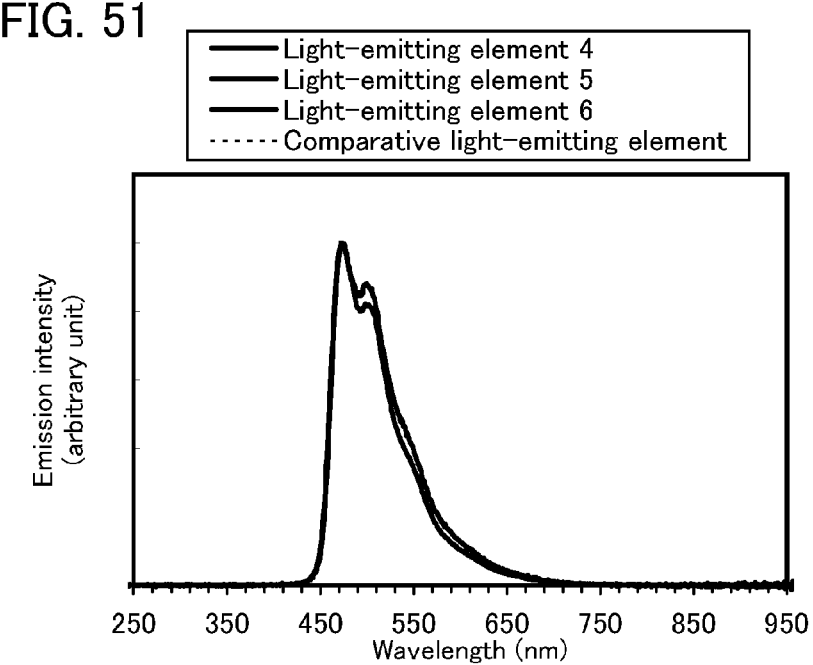
FIG. 51 shows emission spectra of light-emitting elements 4 to 6 and a comparative light-emitting element.

FIG. 51 shows emission spectra when a current at a current density of 0.1 mA/cm² was supplied to the light-emitting elements 4 to 6 and the comparative light-emitting element. As shown in FIG. 51, the emission spectrum of the light-emitting element 4 has a maximum peak at 473 nm; the emission spectrum of the light-emitting element 5 has a maximum peak at 472 nm; and the emission spectrum of the light-emitting element 6 has a maximum peak at 470 nm. It is thus suggested that the peaks are derived from emission of the phosphorescent organometallic iridium complexes included in the light-emitting elements.

Comparisons between the light-emitting element 4 and the light-emitting element 5 show that the emission spectra peak at substantially the same wavelength but the blue chromaticity is better in the light-emitting element 4. The reason for this is that the half width of the spectrum of the light-emitting element 5 is 74 nm, whereas the half width of the spectrum of the light-emitting element 4 is as small as 67 nm. Thus, from the points of view of narrowing an emission spectrum and of improving color purity, at least one of $R^6$ and $R^{10}$ in General Formula (G1) is preferably an alkyl group having 2 or more carbon atoms, more preferably an isopropyl group.

Also in the light-emitting element 6, the half width of the spectrum is as small as 65 nm and the chromaticity is excellent. Thus, from the points of view of narrowing an emission spectrum and of improving color purity, each of $R^1$ and $R^5$ in General Formula (G1) is preferably an alkyl group having 1 to 6 carbon atoms, more preferably a methyl group.

REFERENCE SYNTHESIS EXAMPLE

In this reference synthesis example, a synthesis example of tris{2-[5-(2-methylphenyl)-4-methyl-4H-1,2,4-triazol-3-yl-κN2]phenyl-κC}iridium(III) (abbreviation: [Ir(mpptz-Me)₃]), the phosphorescent organometallic iridium complex represented by the following structural formula and used in the comparative light-emitting element in Example 9, is specifically described.

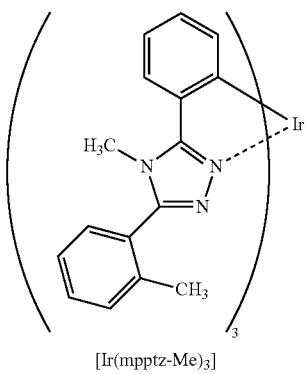

[Ir(mpptz-Me)₃]

Step 1: Synthesis of N-Methyl-o-toluoylamide

First, 12.5 g (185.1 mmol) of methylamine hydrochloride, 150 mL of THF, and 60 mL of triethylamine were put into a 500-mL three-neck flask and stirred at room temperature for 30 minutes. Then, 26.0 g (187.6 mmol) of o-toluoyl chloride was added dropwise and the mixture was stirred at room temperature for 24 hours under nitrogen flow. After reaction for the predetermined time, a precipitated sediment was removed by suction filtration. The obtained filtrate was washed with pure water and then dried with magnesium sulfate. The magnesium sulfate was removed by gravity filtration, and the filtrate was concentrated to give a yellow liquid. This yellow liquid was purified by silica gel chromatography: first, dichloromethane was used as a developing solvent and by-product was removed; then, the developing solvent was replaced with ethyl acetate and an objective substance was collected. The obtained fraction was concentrated to give 16.7 g of a white solid of N-methyl-o-toluoylamide in a yield of 61%. A synthesis scheme of Step 1 is shown in (f-1).

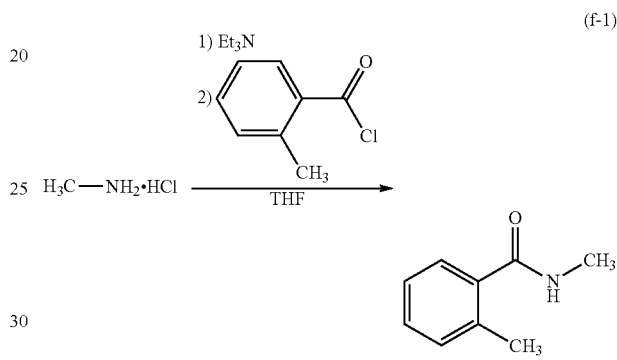

(f-1)

Step 2: Synthesis of N-Methyl-o-toluoylthioamide

Next, 16.1 g (108.0 mmol) of N-methyl-o-toluoylamide obtained in Step 1, 25.0 g (61.8 mmol) of Lawesson's reagent, and 150 mL of toluene were put into a 500-mL three-neck flask and heated and stirred at 120° C. for 6 hours. The reacted solution was concentrated to give an oily substance. This oily substance was purified by silica gel chromatography. Dichloromethane was used as a developing solvent. The obtained fraction was concentrated to give 16.0 g of a white solid of N-methyl-o-toluoylthioamide in a yield of 90%. A synthesis scheme of Step 2 is shown in (f-2).

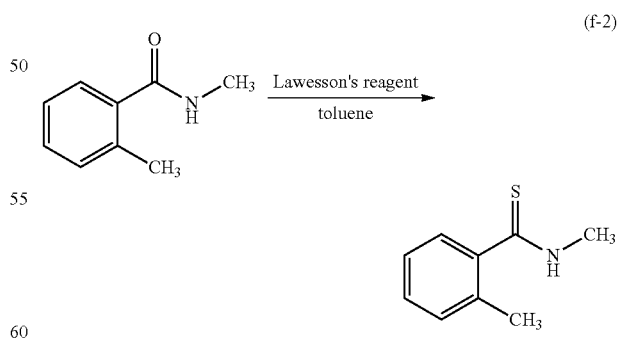

(f-2)

Step 3: Synthesis of N-[(Ethylsulfanyl)(2-methylphenyl)methylidene]methylamine

Into a 200-mL three-neck flask were put 8.0 g (48.4 mmol) of N-methyl-o-toluoylthioamide obtained in Step 2, 3.6 g (53.3 mmol) of sodium ethoxide, and 100 mL of ethanol (EtOH), and the mixture was stirred at room temperature for 1 hour. To this mixed solution, 8.0 g (51.2 mmol) of iodoethane was added and the mixture was heated and stirred at 60° C. for 15 hours. The reacted solution was concentrated to give an oily substance. This oily substance was dissolved in dichloromethane, and washed with water and then a saturated aqueous solution of sodium hydrogen carbonate. After the washing, the organic layer was dried with magnesium sulfate. The obtained mixture was subjected to gravity filtration and the filtrate was concentrated; thus, a crude product of N-[(ethylsulfanyl)(2-methylphenyl)methylidene]methylamine was obtained as a yellow liquid. In the following step, this yellow liquid was used as it was. A synthesis scheme of Step 3 is shown in (f-3).

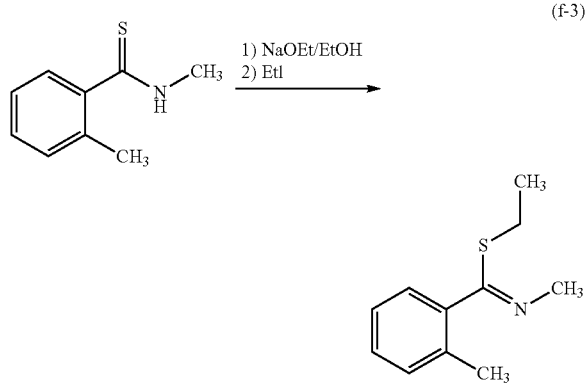

(f-3)

Step 4: Synthesis of 3-(2-Methylphenyl)-4-methyl-5-phenyl-4H-1,2,4-triazole (abbreviation: Hmpptz-Me)

Into a 100-mL three-neck flask were put the total amount of N-[(ethylsulfanyl)(2-methylphenyl)methylidene]methylamine obtained in Step 3, 7.0 g (51.4 mmol) of benzoylhydrazine, and 30 mL of 1-butanol (1-BuOH), and the mixture was heated and stirred at 120° C. for 15 hours. After reaction for the predetermined time, the solvent was distilled off to give a yellow liquid. This liquid was purified by silica gel chromatography. Ethyl acetate was used as a developing solvent. The obtained fraction was concentrated to give a white solid. This solid was recrystallized with ethyl acetate, so that 7.0 g of a white solid of Hmpptz-Me (abbreviation), an objective 4H-triazole derivative, was obtained in a yield of 58%. A synthesis scheme of Step 4 is shown in (f-4).

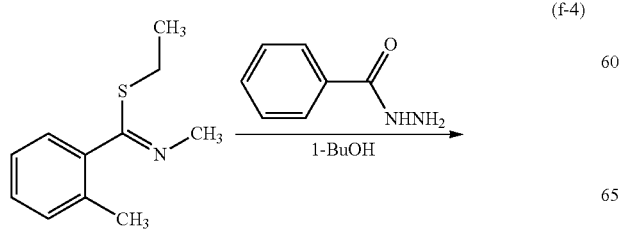

(f-4)

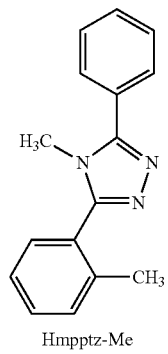

Hmpptz-Me

Step 5: Synthesis of Tris{2-[5-(2-methylphenyl)-4-methyl-4H-1,2,4-triazol-3-yl-κN2]phenyl-κC}iridium(III) (abbreviation: [Ir(mpptz-Me)₃])

Into a container for high-temperature heating were put 3.0 g (12.0 mmol) of Hmpptz-Me (abbreviation), which was the ligand obtained in Step 4, and 1.2 g (2.4 mmol) of tris(acetylacetonato)iridium(III), and degasification was carried out. The mixture in the reaction container was heated and stirred at 250° C. for 48 hours under Ar flow. The reacted mixture was purified by amine-modified silica gel chromatography. As a developing solvent, a mixed solvent of hexane and ethyl acetate in a ratio of 1:2 was used. The obtained fraction was concentrated to give a yellow oily substance. This oily substance was recrystallized with a mixed solvent of ethyl acetate and hexane, so that 65.0 mg of a yellow solid of [Ir(mpptz-Me)₃] (abbreviation), the organometallic complex that is one embodiment of the present invention, was obtained in a yield of 3%. A synthesis scheme of Step 5 is shown in (f-5).

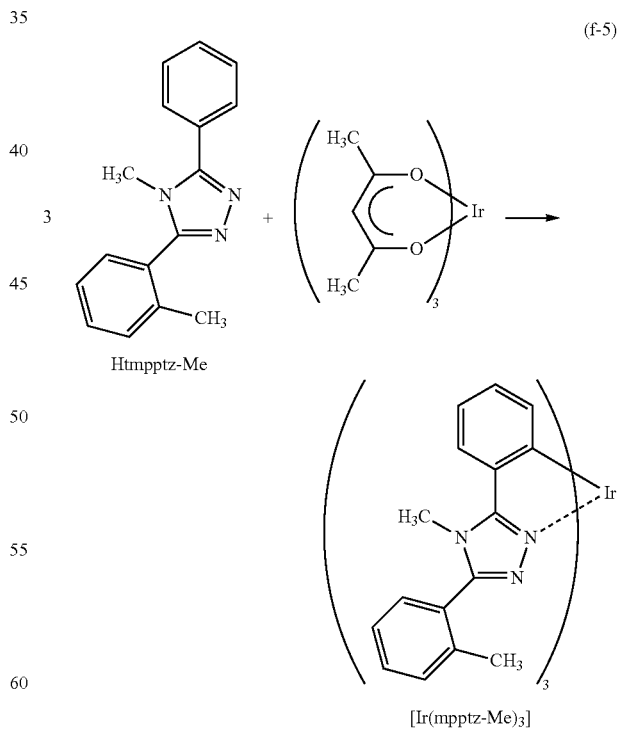

(f-5)

This application is based on Japanese Patent Application serial no. 2012-038535 filed with Japan Patent Office on Feb. 24, 2012, the entire contents of which are hereby incorporated by reference.

What is claimed is:

1. A complex comprising a structure represented by Formula (G1),

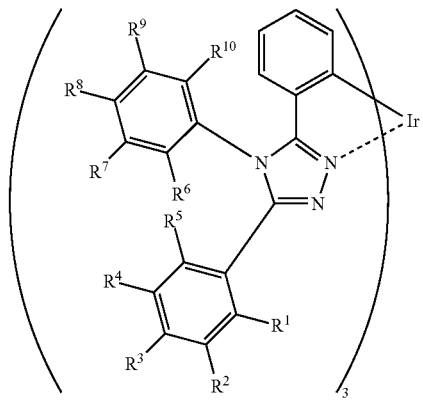 (G1)

wherein:

$R^1$ represents an alkyl group having 1 to 6 carbon atoms; and $R^2$ to $R^{10}$ independently represent hydrogen or an alkyl group having 1 to 6 carbon atoms.

2. The complex according to claim 1, wherein the complex is represented by Formula (G2):

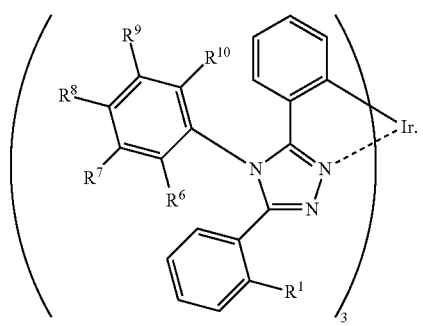 (G2)

3. The complex according to claim 1, wherein the complex is represented by any one of Formulae (100), (101), (105), (112), and (121):

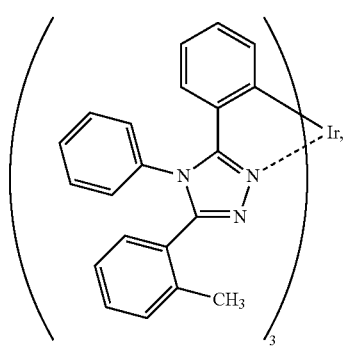 (100)

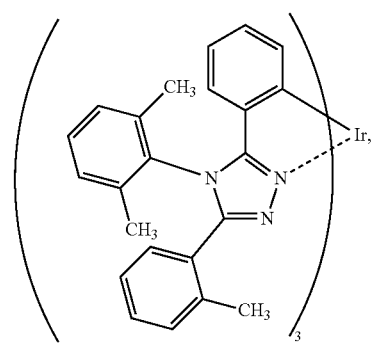 (101)

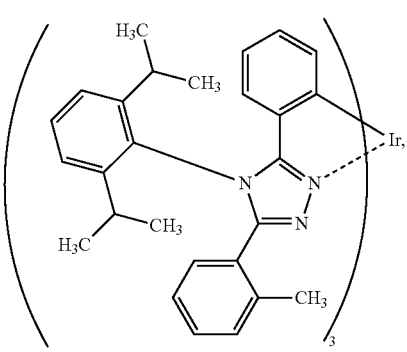 (105)

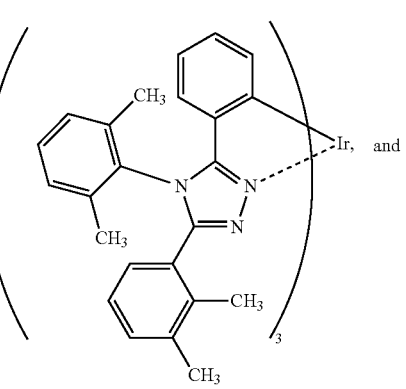 (112) and

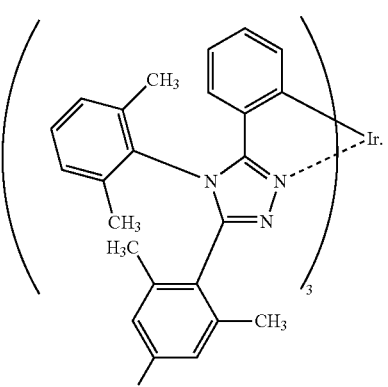 (121)

4. A light-emitting device comprising a complex, wherein:

the complex is represented by Formula (G1);

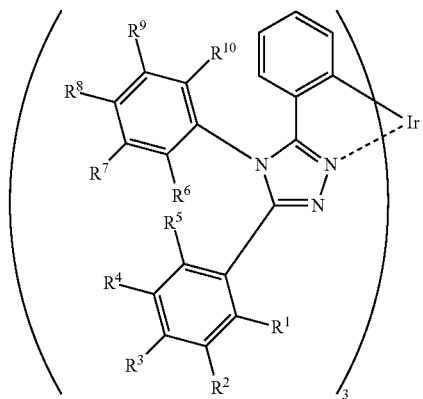

$R^1$ represents an alkyl group having 1 to 6 carbon atoms; and $R^2$ to $R^{10}$ independently represent hydrogen or an alkyl group having 1 to 6 carbon atoms.

5. The light-emitting device according to claim 4, wherein the complex is represented by Formula (G2):

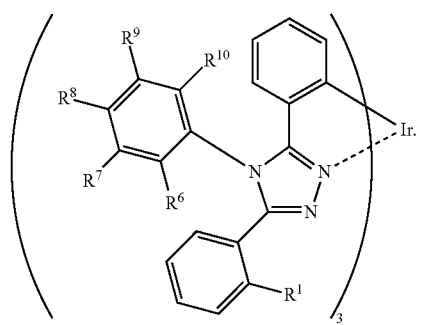

6. The light-emitting device according to claim 4, wherein the complex is represented by any one of Formulae (100), (101), (105), (112), and (121):

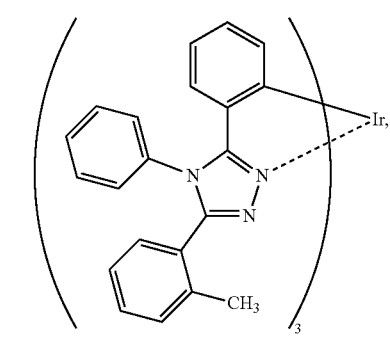

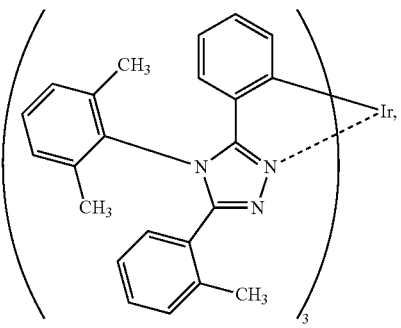

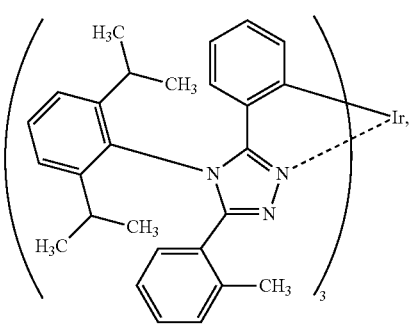

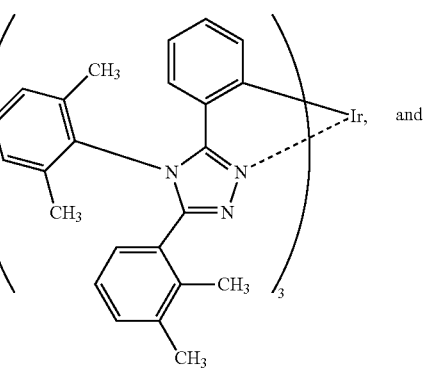

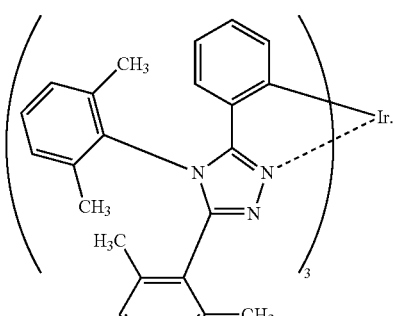

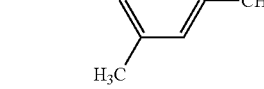

7. An electronic device comprising the light-emitting device according to claim 4.

8. A lighting device comprising the light-emitting device according to claim 4.

9. A light-emitting device comprising a light-emitting layer, wherein:

the light-emitting layer comprises a complex represented by Formula (G1) and a first organic compound;

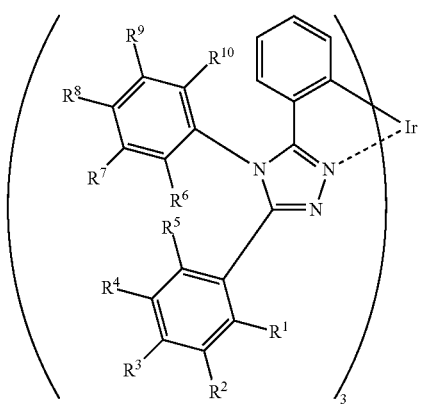

(G1)

R[1] represents an alkyl group having 1 to 6 carbon atoms; and

R[2] to R[10] independently represent hydrogen or an alkyl group having 1 to 6 carbon atoms.

10. The light-emitting device according to claim 9, wherein the complex is represented by Formula (G2):

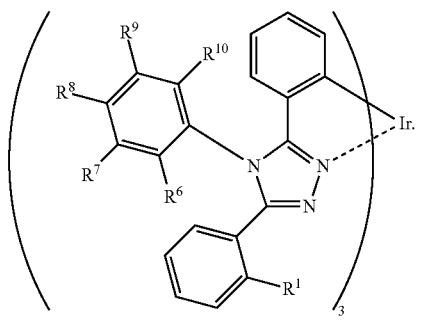

(G2)

11. The light-emitting device according to claim 9, wherein the complex is represented by any one of Formulae (100), (101), (105), (112), and (121):

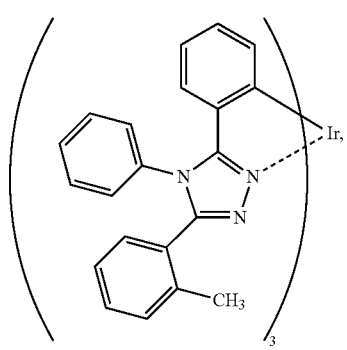

(100)

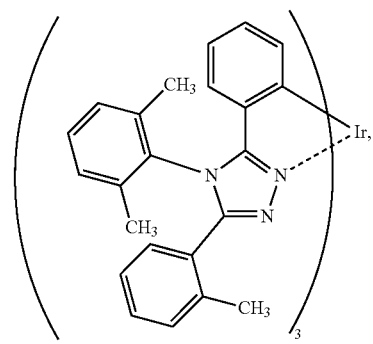

(101)

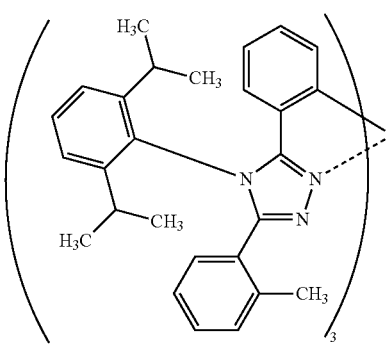

(105)

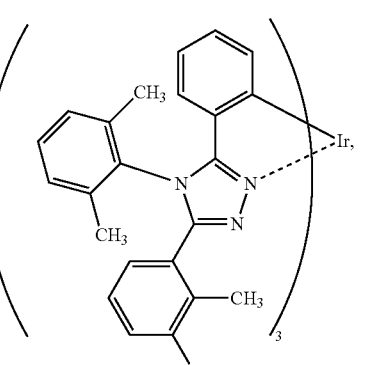

(112)

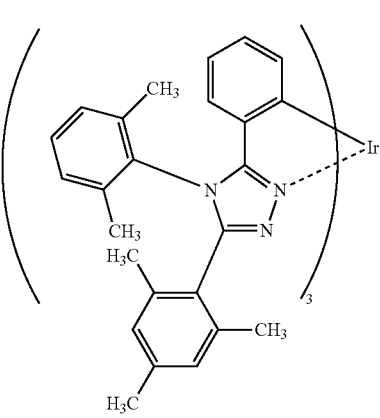

(121)

12. The light-emitting device according to claim 9, wherein the first organic compound is selected from an aromatic amine, a carbazole derivative, a nitrogen-containing heterocyclic compound, and a metal complex.

13. The light-emitting device according to claim 9, further comprising a second organic compound in the light-emitting layer, wherein:
the first organic compound is a nitrogen-containing heteroaromatic compound; and
the second organic compound is selected from a carbazole derivative, an indole derivative and an aromatic amine.

14. An electronic device comprising the light-emitting device according to claim 9.

15. A lighting device comprising the light-emitting device according to claim 9.

16. A light-emitting device comprising a first light-emitting layer and a second light-emitting layer over the first light-emitting layer,
wherein:
the first light-emitting layer comprises a first complex, a first compound, and a second compound;
the second light-emitting layer comprises a second complex and the first compound;
each of the first complex and the second complex is represented by Formula (G1);

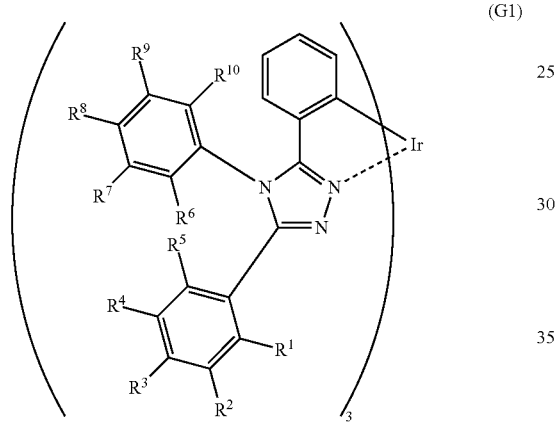

(G1)

$R^1$ represents an alkyl group having 1 to 6 carbon atoms; and
$R^2$ to $R^{10}$ independently represent hydrogen or an alkyl group having 1 to 6 carbon atoms.

17. The light-emitting device according to claim 16, wherein each of the first complex and the second complex is represented by Formula (G2):

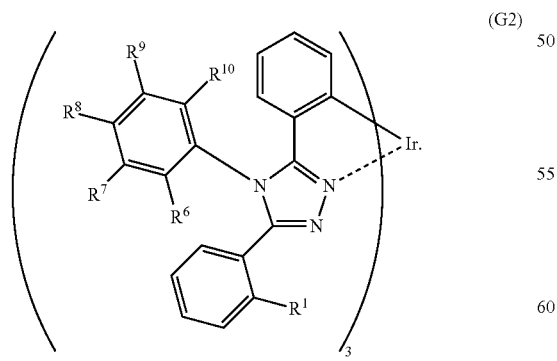

(G2)

18. The light-emitting device according to claim 16, wherein each of the first complex and the second complex is represented by any one of Formulae (100), (101), (105), (112), and (121):

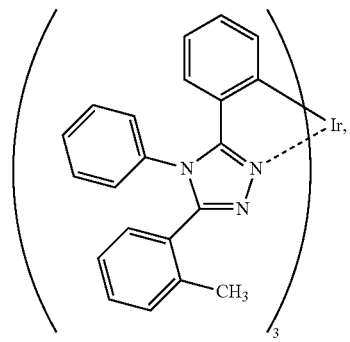

(100)

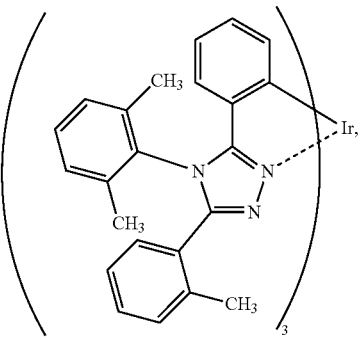

(101)

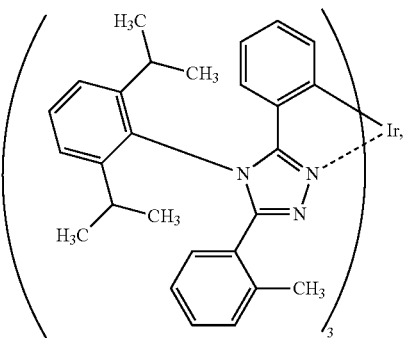

(105)

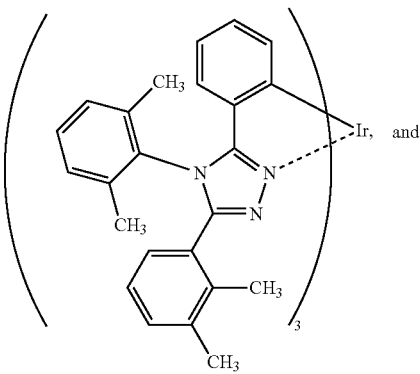

(112)

-continued

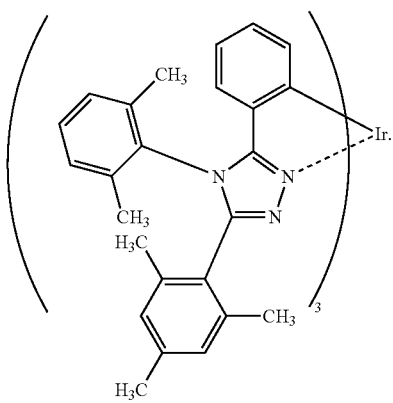
(121)

19. The light-emitting device according to claim 16, wherein:
the first compound is a nitrogen-containing heteroaromatic compound; and
the second compound is selected from a carbazole derivative, an indole derivative, and an aromatic amine.

20. The light-emitting device according to claim 16, wherein the first complex is different from the second complex.

21. An electronic device comprising the light-emitting device according to claim 16.

22. A lighting device comprising the light-emitting device according to claim 16.

23. The light-emitting device according to claim 16, comprising a charge generation layer between the first light-emitting layer and the second light-emitting layer.

24. The light-emitting device according to claim 9, wherein the first organic compound is 2-[3-(dibenzothiophen-4-yl)phenyl]dibenzo[f,h]quinoxaline.

* * * * *